(12) United States Patent
Ito et al.

(10) Patent No.: US 11,911,480 B2
(45) Date of Patent: *Feb. 27, 2024

(54) SELF-EMULSIFYING COMPOSITION OF ω-3 FATTY ACID

(71) Applicant: MOCHIDA PHARMACEUTICAL CO., LTD., Tokyo (JP)

(72) Inventors: Hiromitsu Ito, Tokyo (JP); Hirosato Fujii, Tokyo (JP); Motoo Yamagata, Tokyo (JP)

(73) Assignee: MOCHIDA PHARMACEUTICAL CO., LTD., Tokyo (JP)

( * ) Notice: Subject to any disclaimer, the term of this patent is extended or adjusted under 35 U.S.C. 154(b) by 301 days.

This patent is subject to a terminal disclaimer.

(21) Appl. No.: 16/931,592

(22) Filed: Jul. 17, 2020

(65) Prior Publication Data
US 2020/0345852 A1 Nov. 5, 2020

Related U.S. Application Data

(63) Continuation of application No. 15/545,197, filed as application No. PCT/JP2015/051558 on Jan. 21, 2015, now Pat. No. 10,758,622.

(51) Int. Cl.

| | | |
|---|---|---|
| A61K 47/44 | (2017.01) | |
| A23L 33/12 | (2016.01) | |
| A61K 9/00 | (2006.01) | |
| A61K 9/107 | (2006.01) | |
| A61K 9/48 | (2006.01) | |
| A61K 31/202 | (2006.01) | |
| A61K 31/232 | (2006.01) | |
| A61K 47/24 | (2006.01) | |
| A61K 47/26 | (2006.01) | |

(52) U.S. Cl.
CPC .............. *A61K 47/44* (2013.01); *A23L 33/12* (2016.08); *A61K 9/0053* (2013.01); *A61K 9/107* (2013.01); *A61K 9/1075* (2013.01); *A61K 9/48* (2013.01); *A61K 9/4858* (2013.01); *A61K 9/4866* (2013.01); *A61K 9/4875* (2013.01); *A61K 31/202* (2013.01); *A61K 31/232* (2013.01); *A61K 47/24* (2013.01); *A61K 47/26* (2013.01); *A23V 2002/00* (2013.01)

(58) Field of Classification Search
None
See application file for complete search history.

(56) References Cited

U.S. PATENT DOCUMENTS

| | | | | |
|---|---|---|---|---|
| 8,618,168 B2 * | 12/2013 | Fujii | ............... | A61K 47/44 |
| | | | | 514/975 |
| 9,889,108 B2 | 2/2018 | Harada et al. | | |
| 10,758,622 B2 * | 9/2020 | Ito | ............... | A61P 9/10 |
| 2009/0149533 A1 | 6/2009 | Almarsson et al. | | |
| 2012/0065264 A1 | 3/2012 | Fujii et al. | | |
| 2012/0207800 A1 | 8/2012 | Abu-Baker et al. | | |
| 2012/0232141 A1 | 9/2012 | Hustvedt et al. | | |
| 2014/0141076 A1 | 5/2014 | Haraguchi et al. | | |
| 2016/0151319 A1 | 6/2016 | Kimura et al. | | |
| 2016/0158184 A1 | 6/2016 | Ito et al. | | |

FOREIGN PATENT DOCUMENTS

| | | |
|---|---|---|
| JP | 2008-516890 A | 5/2008 |
| JP | 2012-180337 A | 1/2011 |
| JP | 2012-519728 A | 8/2012 |
| JP | 2013-508296 A | 3/2013 |
| JP | 2016/008849 A1 | 4/2013 |
| WO | WO2010/119319 A1 | 10/2010 |
| WO | 2011-12003 A | 11/2010 |
| WO | WO 2010/134614 A1 | 11/2010 |
| WO | WO 2013/148136 A1 | 10/2013 |
| WO | WO 2014/142364 A2 | 9/2014 |
| WO | WO 2015/008848 A1 | 1/2015 |
| WO | WO 2015/008849 A1 | 1/2015 |

OTHER PUBLICATIONS

Extended European Search Report, dated Jul. 5, 2018, for European Application No. 15878752.3.
Fujii et al., CAS SciFinder English language abstract of WO 2010/134614 A1 (Nov. 25, 2010) (CAPLUS Acc. No. 2010:1468036).
International Search Report for PCT/JP2015/051558 dated Mar. 10, 2015.
Machine English translation of WO 2010/134614 A1 (Nov. 25, 2010).
Ratanabanangkoon et al., "A high-throughput approach towards a novel formulation of fenofibrate in omega-3 oil", European Journal of Pharmaceutical Sciences, 2008, vol. 33, pp. 351-360.
Written Opinion of the International Searching Authority for PCT/JP2015/051558 (PCT/ISA/237) dated Mar. 10, 2015.
U.S. Appl. No. 15/545,178, filed Jul. 20, 2017.
Japanese Office Action for corresponding Japanese Application No. 2020-176384, dated Mar. 15, 2022.
Rowe et al., "Polyoxyethylene Sorbitan Fatty Acid Esters," Handbook of Pharmaceutical Excipients, 5th Ed., 2006, pp. 580-584 (8 pages total).

* cited by examiner

*Primary Examiner* — Brian J Davis
(74) *Attorney, Agent, or Firm* — Birch, Stewart, Kolasch & Birch, LLP

(57) ABSTRACT

A self-emulsifying composition contains: 70 to 90% by weight of at least one compound selected from the group consisting of ω3 polyunsaturated fatty acids and their pharmaceutically acceptable salts and esters; 0.5 to 6% by weight of water; 1 to 29% by weight of a polyoxyethylene sorbitan fatty acid ester as an emulsifier (optionally including a polyoxyl castor oil, and not including lecithin); and lecithin in an amount of 3 to 40 parts by weight in relation to 100 parts by weight of ω3 polyunsaturated fatty acids and the like. The self-emulsifying composition is excellent in self-emulsifying property, composition dispersibility, emulsion stability, and absorbability, is free from ethanol and polyhydric alcohols or only has such an alcohol added thereto at a reduced concentration, and is useful for foods and pharmaceuticals.

12 Claims, No Drawings

SELF-EMULSIFYING COMPOSITION OF ω-3 FATTY ACID

CROSS-REFERENCE TO RELATED APPLICATIONS

The present application is a 37 C.F.R. § 1.53(b) continuation of U.S. application Ser. No. 15/545,197 filed Jul. 20, 2017, which is the National Phase of PCT International Application No. PCT/JP2015/051558 filed Jan. 21, 2015. The entire contents of each application is hereby incorporated by reference.

TECHNICAL FIELD

This invention provides a self-emulsifying composition containing at least one member selected from the group consisting of ω3 polyunsaturated fatty acids and their pharmaceutically acceptable salts and esters. This invention also provides its pharmaceutical product, its production method, a therapeutic method using such pharmaceutical product, and a method for using the same.

BACKGROUND ART

Known ω3 polyunsaturated fatty acids (hereinafter abbreviated as ω3 PUFA) include α-linolenic acid, eicosapentaenoic acid (hereinafter abbreviated as EPA), and docosahexaenoic acid (hereinafter abbreviated as DHA). Since the ω3 PUFA and pharmaceutically acceptable salts and esters thereof (hereinafter abbreviated as ω3 PUFA) have actions such as anti-arteriosclerosis action, platelet aggregation suppressive action, blood lipid lowering action, anti-inflammatory action, carcinostatic action, and central action, they are blended in various food products, and commercially sold in the form of health food and medical and pharmaceutical products.

Ethyl eicosapentaenoate ester (hereinafter abbreviated as EPA-E) is commercially sold in Japan as an oral therapeutic agent for ameliorating ulcer, pain, and coldness associated with arteriosclerosis obliterans (hereinafter abbreviated as ASO) as well as hyperlipidemia (product name Epadel, Mochida Pharmaceutical Co., Ltd.). When EPA-E is orally administered under fasting, increase in plasma EPA concentration is smaller than the case of the oral administration after the meal conceivably because absorption of the EPA-E requires secretion of bile acid and food components as a carrier. Accordingly, Epadel is instructed to be orally administered after the meal (see Non-Patent Literature 1).

However, dosage method or drug compliance has become a problem for those people not taking breakfast with the recent change in the life style, patients who can only take meals at a reduced amount, patients who can only take a fluid diet (milk, rice broth, starch gruel, egg, soup, juice, or oral nutritional supplement), patients with reduced absorption ability of the intestinal tract (for example, elderly, patients of intestinal disease, patients after intestinal surgery, terminal cancer patients, and patients taking a lipase inhibitor), or patients who are unable to take meals such as those after the cerebral infarction.

Attention is also being given to the relation between the hypertriglyceridemia in non-fasting conditions wherein serum triglyceride (hereinafter abbreviated as TG) that had been normal in fasting conditions exhibits abnormal increase after the meal and such condition is retained for a while and coronary artery diseases, and accordingly, there is a demand for an ω3PUFA preparation which is rapidly absorbed by pre-meal administration to suppress the increase of the post-meal increase of the serum TG.

A self-emulsifying preparation which does not contain water in the preparation and which is readily dispersible and self-emulsifying when brought in contact with water has been reported (see Patent Literature 1 and Non-Patent Literature 4). This preparation contains an ω3 PUFA and fenofibrate as its effective components, ethanol, and a surfactant.

These compositions contain ethanol as a component added for improving the dissolution of the fenofibrate. However, volatilization of the ethanol is associated with the risk of capsule deformation and bubble inclusion in the capsule, damages in the quality such as capsule deformation and cracks, as well as denaturing of the content in the capsule such as cloudiness and separation. In addition, use of a preparation containing such composition should be impossible or difficult if not impossible for patients intolerable for the alcohol (ethanol).

A self-emulsifying composition containing ethanol and polyhydric alcohols in addition to the ω3 PUFA and a surfactant which is capable of forming a dispersion having a small or very small average particle size when brought in contact with water is also reported (Patent Literature 2).

With regard to self-emulsifying compositions having a low ethanol content, a self-emulsifying composition comprising an ω3 PUFA, an emulsifier having a hydrophile lipophile balance (hereinafter abbreviated as HLB) of at least 10, lecithin, and a polyhydric alcohol such as propylene glycol or glycerin which has high self-emulsifying property, oral fasting absorbability and absorption speed has been reported (Patent Literature 3).

A self-emulsifying composition containing an ω3PUFA ester and a surfactant but not containing ω3PUFA free acid, which is not affected by meal has been reported (Patent Literature 4). However, the composition in which EPA-E is mainly contained as the ω3PUFA ester is not examined.

When a composition containing a co-solvent such as a polyhydric alcohol is encapsulated in a capsule, the co-solvent moves to the capsule film to cause denaturing of the composition as well as capsule deformation due to the softening of the capsule (Patent Literature 5).

Self-emulsifying compositions, as generally containing larger amounts of emulsifiers and, accordingly, being increased in total amount, are liable to cause inflammation of the gastrointestinal tract or have a reduced content per capsule of the biologically active component dissolved in oil component (Patent Literature 6). Accordingly, the emulsifier used in the self-emulsifying composition is preferably the one which is non-toxic or less-toxic even in the case of continuous administration, and the emulsifier is preferably used at a low content.

In view of compliance, amount of the emulsifier and alcohols incorporated should be minimized also in consideration of reducing the size of the preparation because amount of the preparation that has to be taken per administration increases with the increase in the amount of the components other than the ω3 PUFA in the self-emulsifying composition since predetermined amount of the ω3 PUFA should be taken per administration.

CITATION LIST

Patent Literatures

[Patent Literature 1] JP 2008-516890 A
[Patent Literature 2] JP 2012-519728 A

[Patent Literature 3] WO 2010/134614
[Patent Literature 4] WO 2013/148136
[Patent Literature 5] JP 2011-12003 A
[Patent Literature 6] JP 2012-180337 A Non-Patent Literatures

[Non-Patent Literature 1] Epadel S (Drug Interview Form), Mochida Pharmaceutical Co., Ltd., June, 2012
[Non-Patent Literature 2] "Guideline for Diagnosis and Prevention of Atherosclerotic Cardiovascular Diseases, 2007 Edition" edited by Japan Atherosclerosis Society and published by Kyowa Kikaku Ltd., Apr. 25, 2007
[Non-Patent Literature 3] Diabetes, vol. 57, no. 9, 2382-2392, 2008
[Non-Patent Literature 4] European Journal of Pharmaceutical Sciences, vol. 33, 351-360, 2008
[Non-Patent Literature 5] "2007 Dictionary of Drug Additives" edited by International Pharmaceutical Excipients Council Japan and published by Yakuji Nippo Ltd., Jul. 25, 2007

SUMMARY OF INVENTION

Technical Problems

There is a demand for a preparation wherein amount of the ethanol and polyhydric alcohol in the self-emulsifying composition has been reduced.

There is also a demand for a preparation wherein amount of the emulsifier in the self-emulsifying composition has been reduced.

There is also a demand for a preparation wherein amount of the ω3PUFA in the self-emulsifying composition has been increased.

There is also a demand for a self-emulsifying composition with excellent compliance.

There is also a demand for a self-emulsifying composition which can retain its good appearance without exhibiting denaturing such as cloudiness or separation even if stored in low or high temperature conditions in addition to the room temperature since the self-emulsifying composition may be stored in cold area in its use as a drug.

There is also a demand for a self-emulsifying composition wherein the composition has stable quality.

There is also a demand for a preparation wherein the composition has been encapsulated.

There is also a demand for a preparation wherein softening of the capsule film in the encapsulation of the composition has been suppressed so that the preparation is not deformed.

There is also a demand for a self-emulsifying composition with improved absorption of the ω3PUFA.

There is also a demand for a self-emulsifying composition which exhibits the same pharmacokinetics as the conventional pharmacokinetics immediately after the post-meal administration of the ω3PUFA preparation even if administered at a smaller dose of the ω3PUFA.

There is also a demand for a method for increasing the ω3PUFA concentration in blood (the term "in blood" means "in whole blood, plasma, or serum" and this also applies to the following description) after the administration of the self-emulsifying composition.

There is also a demand for a self-emulsifying composition with reduced side effects (side effects of lower gastrointestinal tract, nausea, abdominal discomfort, diarrhea, abdominal pain, heartburn, vomiting, anorexia, constipation, stomatitis, thirst, bloating, flatulence, etc.) as well as a method for such reduction.

There is also a demand for a self-emulsifying composition wherein absorption of the ω3PUFA is not or little affected by the meal as well as a method thereof.

There is also a demand for a self-emulsifying composition which can be absorbed even when administered at a high dose at the level that the absorption of the ω3PUFA would be saturated with no further absorption in blood if the ω3PUFA were solely administered.

There is also a demand for an emulsion with improved absorption of the ω3PUFA, a self-emulsifying composition for enabling quick production of the emulsion, and a method for producing the emulsion.

Accordingly, an object of the present invention is to provide a self-emulsifying composition which is capable of solving at least one of the problems as described above, a preparation encapsulating such composition, a therapeutic method using such preparation, and a method for using such preparation.

Solution to Problems

In view of the situation as described above, the inventors of the present invention conducted an intensive investigation on components which can substitute the ethanol and polyhydric alcohol and found that a predetermined amount of water is useful for improving compatibility of the self-emulsifying composition.

The inventors also found that since the content of water in the composition can be reduced to 0.5 to 6% by weight which is lower than the case of ethanol and polyhydric alcohol, and the content of the emulsifier can be further reduced by the improvement in compatibility caused by this small amount of water, production of a self-emulsifying composition having high content the ω3PUFA is thereby enabled.

The inventors also found that a self-emulsifying composition which is excellent in at least one of the objects as described above can be produced, and the present invention was thereby completed.

The inventors also found that content of the emulsifier can be further reduced and the present invention of the self-emulsifying composition having a high content of ω3PUFA was thereby completed.

The inventors also found that incorporation of the particular emulsifier enables production of a self-emulsifying composition which is favorable in at least one of higher blood concentration of the ω3PUFA, reduced side effects, absorption of the ω3PUFA not or least affected by the meal, unsaturation in the amount of the ω3PUFA absorption, and the like, and the present invention was thereby completed.

The composition of the present invention is a composition which is excellent in at least one of the aspects as described above.

The first aspect of the present invention is the self-emulsifying composition as described below.

(1-1) A self-emulsifying composition characterized in that, when the total amount of the self-emulsifying composition is 100% by weight, it comprises
    a) 70 to 90% by weight of at least one compound selected from the group consisting of ω3PUFA and their pharmaceutically acceptable salts and esters, b) 0.5 to 6% by weight of water,
c) 1 to 29% by weight of an emulsifier (not including lecithin), which is preferably polyoxyethylene sorbitan fatty acid ester, and
d) lecithin at an amount of 3 to 40 parts by weight, or 1 to 25 parts by weight in relation to 100 parts by weight of ω3 polyunsaturated fatty acids or their pharmaceutically acceptable salts and esters, wherein
e) content of ethanol and/or polyhydric alcohol is up to 4% by weight of the total composition.

(1-2) A self-emulsifying composition characterized in that, when the total amount of the self-emulsifying composition is 100% by weight, it comprises
a) 70 to 90% by weight of at least one compound selected from the group consisting of ω3 PUFA and their pharmaceutically acceptable salts and esters,
b) 0.5 to 6% by weight of water,
c) 1 to 29% by weight of an emulsifier which is preferably polyoxyethylene sorbitan fatty acid ester, and
d) lecithin at an amount of 3 to 40 parts by weight, or 1 to 25 parts by weight in relation to 100 parts by weight of at least one compound selected from the group consisting of ω3 polyunsaturated fatty acids and their pharmaceutically acceptable salts and esters, and
e) content of ethanol is up to 4% by weight of the total composition, and
f) content of polyhydric alcohol is up to 4% by weight of the total composition.

(1-3) A self-emulsifying composition according to the above (1-1) or (1-2) wherein the polyoxyethylene sorbitan fatty acid ester is at least one member selected from the group consisting of polyoxyethylene (20) sorbitan monolaurate, polyoxyethylene (20) sorbitan monopalmitate, polyoxyethylene (20) sorbitan monostearate, polyoxyethylene (20) sorbitan tristearate, polyoxyethylene (20) sorbitan monoisostearate, polyoxyethylene (20) sorbitan monooleate, and polyoxyethylene (20) sorbitan trioleate.

(1-4) A self-emulsifying composition according to any one of the above (1-1) to (1-3) wherein the emulsifier further comprises polyoxyethylene hydrogenated castor oil and/or polyoxyethylene castor oil.

(1-5) A self-emulsifying composition according to any one of the above (1-1) to (1-4) wherein the emulsifier further comprises polyoxyethylene castor oil.

(1-6) A self-emulsifying composition according to any one of the above (1-1) to (1-5) wherein the polyhydric alcohol is propylene glycol or glycerin.

(1-7) A self-emulsifying composition according to any one of the above (1-1) to (1-6) wherein the polyhydric alcohol content in the composition is 0 to 4% by weight.

(1-8) A self-emulsifying composition according to any one of the above (1-1) to (1-6) wherein the polyhydric alcohol content in the composition is not in excess of 4% by weight.

(1-9) A self-emulsifying composition according to any one of the above (1-1) to (1-8) wherein the polyhydric alcohol content in the composition is up to 1% by weight.

(1-10) A self-emulsifying composition according to any one of the above (1-1) to (1-9) wherein the polyhydric alcohol content in the composition is 0 to 1% by weight, (1-11) A self-emulsifying composition according to any one of the above (1-1) to (1-8) wherein the polyhydric alcohol content in the composition is not in excess of 1% by weight.

(1-12) A self-emulsifying composition according to any one of the above (1-1) to (1-11) wherein the composition is substantially free from the polyhydric alcohol.

(1-13) A self-emulsifying composition according to any one of the above (1-1) to (1-12) wherein the ethanol content in the composition is up to 4% by weight.

(1-14) A self-emulsifying composition according to any one of the above (1-1) to (1-12) wherein the ethanol content in the composition is 0 to 4% by weight.

(1-15) A self-emulsifying composition according to any one of the above (1-1) to (1-12) wherein the ethanol content in the composition is not in excess of 4% by weight.

(1-16) A self-emulsifying composition according to any one of the above (1-1) to (1-15) wherein the composition is substantially free from the ethanol.

(1-17) A self-emulsifying composition according to any one of the above (1-1) to (1-16) wherein the ω3PUFA and their pharmaceutically acceptable salts and esters are at least one member selected from the group consisting of EPA, DHA, and their pharmaceutically acceptable salts and esters.

(1-18) A self-emulsifying composition according to any one of the above (1-1) to (1-17) wherein the ω3PUFA ester is ethyl ester or triglyceride ester.

(1-19) A self-emulsifying composition according to any one of the above (1-1) to (1-18) wherein the ω3PUFA and their pharmaceutically acceptable salts and esters are EPA-E or ethyl ester of DHA (hereinafter referred to as DHA-E).

(1-20) A self-emulsifying composition according to any one of the above (1-1) to (1-19) wherein the composition contains the at least one member selected from the group consisting of EPA, DHA, and their pharmaceutically acceptable salts and esters as its effective component.

(1-21) A self-emulsifying composition according to any one of the above (1-1) to (1-20) wherein the composition contains EPA-E and/or DHA-E as its effective component.

(1-22) A self-emulsifying composition according to any one of the above (1-1) to (1-21) containing EPA-E as its effective component.

(1-23) A self-emulsifying composition according to any one of the above (1-1) to (1-22) wherein the lecithin is at least one member selected from the group consisting of soybean lecithin, zymolytic soybean lecithin, hydrogenated soybean lecithin, and egg yolk lecithin.

(1-24) A self-emulsifying composition according to any one of the above (1-1) to (1-23) wherein content of at least one emulsifier selected from the group consisting of polyoxyethylene hydrogenated castor oil, polyethylene glycol fatty acid ester, and polyoxyethylene polyoxypropylene glycol is less than 5% by weight of total amount of the composition. And also, the self-emulsifying composition according to any one of the above (1-1) to (1-23) wherein content of each of the emulsifiers, namely, polyoxyethylene hydrogenated castor oil, polyoxyethylene glycol fatty acid ester, and polyoxyethylene polyoxypropylene glycol is less than 5% by weight of total amount of the composition.

(1-25) A self-emulsifying composition according to any one of the above (1-1) to (1-24) characterized in that a) to d) are mixed in any order.

(1-26) A self-emulsifying composition according to any one of the above (1-1) to (1-25) wherein the composition has transparent appearance when it is allowed to stand.

(1-27) A self-emulsifying composition according to any one of the above (1-1) to (1-25) wherein the composition has an appearance without separation or cloudiness when it is allowed to stand.

(1-28) A self-emulsifying composition according to any one of the above (1-1) to (1-27) wherein the composition has transparent appearance when it is stored in the environment of 5° C. or 40° C. for 12 hours.

(1-29) A self-emulsifying composition according to any one of the above (1-1) to (1-28) wherein the composition has an appearance without separation or cloudiness when it is stored in the environment of 5° C. or 40° C. for 12 hours.
(1-30) A self-emulsifying composition according to any one of the above (1-1) to (1-29) wherein the composition is excellent in at least one of self-emulsifying property, dispersibility of the composition, and emulsion stability.
(1-31) A self-emulsifying composition according to any one of the above (1-1) to (1-30) wherein the composition emulsifies by itself when 10 μL of the composition is added dropwise to 5 ml of purified water or first solution of the dissolution test of Japanese Pharmacopeia at 37° C.
(1-32) A self-emulsifying composition according to any one of the above (1-1) to (1-31) wherein the composition disperses by stirring when 10 μL of the composition is added dropwise to 5 ml of purified water or first solution of the dissolution test of Japanese Pharmacopeia at 37° C.
(1-33) A self-emulsifying composition according to any one of the above (1-1) to (1-32) wherein the composition does not experience separation of oil when 10 μL of the composition is added dropwise to 5 ml of purified water or first solution of the dissolution test of Japanese Pharmacopeia at 37° C.
(1-34) A self-emulsifying composition according to any one of the above (1-1) to (1-33) wherein, when the self-emulsifying composition according to any one of the above (1-1) to (1-33) at an amount in terms of the at least one compound selected from the group consisting of ω3PUFA and their pharmaceutically acceptable salts and esters of 600 mg is orally administered to each male beagle under the condition of at least 18 hours of fasting, and the plasma ω3PUFA concentration is calculated by conducting the correction by subtracting ω3PUFA concentration in plasma before the administration, the maximum plasma ω3PUFA concentration (also referred to as the maximum blood concentration) is at least 50 μg/ml, and/or the area under the curve of the plasma ω3PUFA concentration at 0 to 2 hours after the administration is at least 30 μg·hr/mL; the maximum plasma ω3PUFA concentration is at least 50 μg/ml, and/or the area under the curve of the plasma ω3PUFA concentration at 0 to 2 hours after the administration is at least 50 μg·hr/mL; the maximum plasma ω3PUFA concentration is at least 60 μg/ml, and/or the area under the curve of the plasma ω3PUFA concentration at 0 to 2 hours after the administration is at least 60 μg·hr/mL; or the maximum plasma ω3PUFA concentration is at least 70 μg/ml, and/or the area under the curve of the plasma ω3PUFA concentration at 0 to 2 hours after the administration is at least 70 μg·hr/mL.
(1-35) A self-emulsifying composition according to any one of the above (1-1) to (1-33) wherein, when the self-emulsifying composition at an amount in terms of the at least one compound selected from the group consisting of ω3PUFA and their pharmaceutically acceptable salts and esters of 45 mg/kg body weight is orally administered to each male cynomolgus monkey under the condition of at least 12 hours of fasting, and the plasma ω3PUFA concentration is calculated by conducting the correction by subtracting ω3PUFA concentration in plasma before the administration, the maximum plasma ω3PUFA concentration is at least 50 μg/ml, and/or the area under the curve of the plasma ω3PUFA concentration at 0 to 12 hours after the administration is at least 400 μg·hr/mL; or the maximum plasma ω3PUFA concentration is at least 70 μg/ml, and/or the area under the curve of the plasma ω3PUFA concentration at 0 to 12 hours after the administration is at least 500 μg·hr/mL.

(1-36) Use of the self-emulsifying composition according to any one of the above (1-1) to (1-33) wherein, when self-emulsifying composition according to any one of the above (1-1) to (1-33) is orally administered at an amount in terms of the at least one compound selected from the group consisting of ω3PUFA and their pharmaceutically acceptable salts and esters of one selected from the group consisting of 500 mg, 1000 mg, 1800 mg, 2000 mg, 3600 mg, 4000 mg, 6000 mg, and 8000 mg to each human before the meal, the maximum plasma ω3PUFA concentration calculated by conducting the correction by subtracting the plasma ω3PUFA concentration before the administration is at least 50 μg/mL and/or the plasma ω3PUFA concentration 2 hours after the administration is at least 10 μg/mL.
(1-37) A self-emulsifying composition according to any one of the above (1-1) to (1-33) wherein, when self-emulsifying composition according to any one of the above (1-1) to (1-33) is orally administered at an amount in terms of the at least one compound selected from the group consisting of ω3PUFA and their pharmaceutically acceptable salts and esters of one selected from the group consisting of 500 mg, 1000 mg, 1800 mg, 2000 mg, 3600 mg, 4000 mg, 6000 mg, and 8000 mg to each human before the meal, and the plasma ω3PUFA concentration is calculated by conducting the correction by subtracting ω3PUFA concentration in plasma before the administration, the maximum plasma ω3PUFA concentration is at least 10 μg/mL and/or the area under the curve of the plasma ω3PUFA concentration at 0 to 72 hours after the administration is at least 250 μg·hr/mL.
(1-38) A self-emulsifying composition according to (1-1) to (1-37) wherein the polyoxyethylene castor oil is up to 120 parts by weight in relation to 100 parts by weight of the polyoxyethylene sorbitan fatty acid ester in the composition.
(1-39) A self-emulsifying composition characterized in that, when the total amount of the self-emulsifying composition is 100% by weight, it comprises
  a) 70 to 90% by weight of EPA-E,
  b) 0.5 to 6% by weight of water,
  c) 1 to 29% by weight of an emulsifier which is polyoxyethylene sorbitan fatty acid ester, and
  d) lecithin at an amount of 3 to 40 parts by weight, or 1 to 25 parts by weight in relation to 100 part by weight of the EPA-E, and
  e) content of ethanol and/or polyhydric alcohol is up to 4% by weight of the total composition.
(1-40) A self-emulsifying composition characterized in that, when the total amount of the self-emulsifying composition is 100% by weight, it comprises
  a) 70 to 90% by weight of EPA-E,
  b) 0.5 to 6% by weight of water,
  c) 1 to 29% by weight of an emulsifier which is polyoxyethylene sorbitan fatty acid ester, and
  d) lecithin at an amount of 3 to 40 parts by weight, or 1 to 25 parts by weight in relation to 100 part by weight of the EPA-E, and
  e) content of ethanol is up to 4% by weight of the total composition, and
  f) content of polyhydric alcohol is up to 4% by weight of the total composition.

The second aspect of the present invention is the capsulated self-emulsifying preparation as described below.
(2-1) A self-emulsifying capsule preparation wherein the content is the self-emulsifying composition according to any one of the above (1-1) to (1-40) and wherein the composition is encapsulated by a hard capsule and/or a soft capsule.
(2-2) A self-emulsifying capsule preparation according to (2-1) having good hardness immediately after its production.

(2-3) A self-emulsifying capsule preparation according to (2-1) or (2-2) having a hardness of at least 18 kgf immediately after its production.

(2-4) A self-emulsifying capsule preparation according to any one of (2-1) to (2-3), wherein, when the preparation is sealed in an aluminum package and stored at 40° C. for 1 week, the preparation does not experience loss of hardness of 6 kgf or more compared with the hardness before the storage.

(2-5) A self-emulsifying capsule preparation according to any one of (2-1) to (2-4) wherein, when the preparation is sealed in an aluminum package and stored at 40° C. for 1 week, the preparation retains a hardness of at least 20 kgf.

(2-6) A self-emulsifying capsule preparation according to any one of (2-1) to (2-5) wherein, when the preparation is sealed in an aluminum package and stored at 40° C. for 1 week, the hardness after the storage is more than 60% of the hardness before the storage.

(2-7) A preparation according to any one of the above (2-1) to (2-6) which is at least one member selected from the group consisting of therapeutic agents for dyslipidemia (hypercholesterolemia, hyper-LDL cholesterolemia, hyper-non-HDL cholesterolemia, hyper-VLDL cholesterolemia, hypo-HDL cholesterolemia, hypertriglyceridemia, hyper-ApoB-emia, hypo-ApoAI-emia, increased LDL particle number-emia, small LDL particle size-emia, hyper-oxidized LDL-emia, hyper-small dense LDL-emia, hyper-remnant-like lipoprotein cholesterol (RLP-C)-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-high-sensitivity CRP (hereinafter referred to as hs-CRP)-emia, hypo-EPA-emia (the state wherein EPA value in plasma, serum, erythrocyte membrane, platelet membrane is low), hyper-free fatty acidemia), hyper-fasting glucose-emia, hyper-hemoglobin A1c (hereinafter referred to as HbA1c)-emia, hyper insulin resistance index (hereinafter referred to as HOMA-IR)-emia, hyper-intercellular adhesion molecule-1-emia, hyper-interleukin-6 (hereinafter referred to as IL-6)-emia, hyper-plasminogen activator inhibitor-1 (hereinafter referred to as PAI-1)-emia, hypercreatininemia, hyper-aspartic acid aminotransferase (herein after referred to as AST)-emia, hyper-alanineaminotranspherase (hereinafter referred to as ALT)-emia, hyper-uric acidemia, hyper-8-isoprostane-emia, hyper-thromboxane A2 (hereinafter referred to as TXA2)-emia, hyper-leukotriene B2 (hereinafter referred to as LTB2)-emia, etc.), therapeutic agent for postprandial hyperglycemia, antiarteriosclerotic agent, platelet aggregation suppressive agent, therapeutic agent for peripheral circulatory insufficiency, agent for preventing onset of cardiovascular events, therapeutic agent for inflammatory diseases (nonalcoholic fatty liver disease (hereinafter referred to as NAFLD), non-alcoholic steatohepatitis (hereinafter referred to as NASH), etc.), progression suppressant and therapeutic agent of dementia (Alzheimer-type dementia, vascular dementia, mixed-type dementia, etc.), anticancer agent, and preventive and therapeutic agents and progression suppressant for central diseases (depression, depressive state, obsessive-compulsive disorder, social phobia, panic disorder, etc.)

The third aspect of the present invention is the method for producing the self-emulsifying composition as described below.

(3-1) A method for producing a self-emulsifying composition comprising the step of, when the total amount of the self-emulsifying composition is 100% by weight, mixing the following components a) to d) in any order a) 70 to 90% by weight of at least one compound selected from the group consisting of ω3PUFA and their pharmaceutically acceptable salts and esters,
b) 0.5 to 6% by weight of water,
c) 1 to 29% by weight of an emulsifier which is polyoxyethylene sorbitan fatty acid ester, and
d) lecithin at an amount of 3 to 40 parts by weight or 1 to 25 parts by weight in relation to 100 parts by weight of at least one compound selected from the group consisting of ω3 polyunsaturated fatty acids or their pharmaceutically acceptable salts and esters, wherein
e) content of ethanol and/or polyhydric alcohol is up to 4% by weight of the total composition.

(3-2) A method for producing a self-emulsifying composition comprising the step of, when the total amount of the self-emulsifying composition is 100% by weight, mixing the following components a) to d) in any order a) 70 to 90% by weight of at least one compound selected from the group consisting of ω3 PUFA and their pharmaceutically acceptable salts and esters,
b) 0.5 to 6% by weight of water,
c) 1 to 29% by weight of an emulsifier which is polyoxyethylene sorbitan fatty acid ester, and
d) lecithin at an amount of 3 to 40 parts by weight in relation to 100 parts by weight of ω3 polyunsaturated fatty acids or their pharmaceutically acceptable salts and esters, wherein
e) content of ethanol is up to 4% by weight of the total composition, and
f) content of polyhydric alcohol is up to 4% by weight of the total composition.

(3-3) A method for producing a self-emulsifying composition according to (3-1) or (3-2) wherein the method includes the step of mixing the a), b) and/or c) of the step as described above under heating to 70° C.

The fourth aspect of the present invention is a drug for administering the self-emulsifying composition by particular route.

(4-1) A preparation for orally administering the self-emulsifying composition or capsulated self-emulsifying preparation, drug or veterinary drug according to any one of the above (1-1) to (1-40) and (2-1) to (2-7) in the fasting or before going to bed.

(4-2) A preparation for orally administering the self-emulsifying composition or capsulated self-emulsifying preparation, drug or veterinary drug produced by the production method according to any one of the above (3-1) to (3-3) in the fasting or before going to bed.

(4-3) A preparation according to the above (4-1) or (4-2) wherein the drug is at least one member selected from the group consisting of therapeutic agent for dyslipidemia (hypercholesterolemia, hyper-LDL cholesterolemia, hyper-non-HDL cholesterolemia, hyper-VLDL cholesterolemia, hypo-HDL cholesterolemia, hypertriglyceridemia, hyper-ApoB-emia, hypo-ApoAI-emia, increased LDL particle number-emia, small LDL particle size-emia, hyper-oxidized LDL-emia, hyper-small dense LDL-emia, hyper-RLP-C-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-hs-CRP-emia, hypo-EPA-emia (the state wherein EPA value in plasma, serum, erythrocyte membrane, platelet membrane is low), hyper-free fatty acidemia), hyper-fasting glucose-emia, hyper-HbA1c-emia, hyper-HOMA-IR-emia, hyper-intercellular adhesion molecule-1-emia, hyper-IL-6-emia, hyper-PAI-1-emia, hypercreatininemia, hyper-AST-emia, hyper-ALT-emia, hyper-uric acidemia, hyper-8-isoprostaneemia, hyper-TXA2-emia, hyper-LTB2-emia, etc.), therapeutic agent for postprandial hyperglycemia, antiarteriosclerotic agent, platelet aggregation suppressive agent, therapeutic agent for peripheral circulatory insufficiency, agent for preventing onset of cardiovascular events, therapeutic agent for inflammatory diseases (NAFLD, NASH, etc.), anticancer agent, and preventive and therapeutic agents and progression suppressant for central diseases (depression, depressive state, obsessive-compulsive disorder, social phobia, panic disorder, etc.).

(4-4) A preparation according to any one of the above (4-1) to (4-3) which is administered once a day.

(4-5) Method for administering and/or using the preparation according to any one of the above (4-1) to (4-4).

(4-6) A method for increasing the ω3PUFA concentration in plasma by oral administration according to any one of the (4-1) to (4-4).

The fifth aspect of the present invention is a preventive, progression suppressing, or therapeutic method for at least one disease selected from the following group.

(5-1) A preventive, progression suppressing, or therapeutic method for at least one disease selected from dyslipidemia (hypercholesterolemia, hyper-LDL cholesterolemia, hyper-non-HDL cholesterolemia, hyper-VLDL cholesterolemia, hypo-HDL cholesterolemia, hypertriglyceridemia, hyper-ApoB-emia, hypo-ApoAI-emia, increased LDL particle number-emia, small LDL particle size-emia, hyper-oxidized LDL-emia, hyper-small dense LDL-emia, hyper-RLP-C-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-hs-CRP-emia, hypo-EPA-emia (the state wherein EPA value in plasma, serum, erythrocyte membrane, platelet membrane is low), hyper-free fatty acidemia), hyper-fasting glucose-emia, hyper-HbA1c-emia, hyper-HOMA-IR-emia, hyper-intercellular adhesion molecule-1-emia, hyper-IL-6-emia, hyper-PAI-1-emia, hypercreatininemia, hyper-AST-emia, hyper-ALT-emia, hyper-uric acidemia, hyper-8-isoprostane-emia, hyper-TXA2-emia, hyper-LTB2-emia, etc.), postprandial hyperglycemia, arteriosclerosis, increase of platelet aggregation, peripheral circulatory insufficiency, cardiovascular events, inflammatory diseases (NAFLD. NASH, etc.), dementia (Alzheimer-type dementia, vascular dementia, mixed-type dementia, etc.), cancer, and central diseases (depression, depressive state, obsessive-compulsive disorder, social phobia, panic disorder, etc.), wherein at least one self-emulsifying composition or capsulated self-emulsifying preparation, drug or veterinary drug selected from those according to the above (1-1) to (1-40) and (2-1) to (2-7) is orally administered to a patient.

(5-2) A method according to the above (5-1) wherein the self-emulsifying composition or capsulated self-emulsifying preparation, drug or veterinary drug is orally administered in the fasting or before going to bed.

(5-3) A method according to the above (5-1) or (5-2) wherein the self-emulsifying composition or capsulated self-emulsifying preparation, drug or veterinary drug is administered once a day.

The sixth aspect of the present invention is the self-emulsifying composition as described below.

(6-1) A self-emulsifying composition wherein the maximum plasma ω3PUFA concentration determined by orally administering the self-emulsifying composition selected from any one of the above (1-1) to (1-40) and (2-1) to (2-7) at an amount corresponding to 600 mg of the at least one compound selected from the group consisting of ω3PUFA and their pharmaceutically acceptable salts and esters to male beagles under the condition of at least 18 hours of fasting, and conducting the correction by subtracting plasma ω3PUFA concentration before the administration is at least 50 µg/mL and/or the area under the curve of the plasma ω3PUFA concentration at 0 to 2 hours after the administration is at least 30 µg·hr/mL; the maximum plasma ω3PUFA concentration is at least 50 µg/mL and/or the area under the curve of the plasma ω3PUFA concentration at 0 to 2 hours after the administration is at least 50 µg·hr/mL; the maximum plasma ω3PUFA concentration is at least 60 µg/mL and/or the area under the curve of the plasma ω3PUFA concentration at 0 to 2 hours after the administration is at least 60 µg·hr/mL; or the maximum plasma ω3PUFA concentration is at least 70 µg/mL and/or the area under the curve of the plasma ω3PUFA concentration at 0 to 2 hours after the administration is at least 70 µg·hr/mL.

(6-2) A self-emulsifying composition wherein the maximum plasma ω3PUFA concentration determined by orally administering the self-emulsifying composition selected from any one of the above (1-1) to (1-40) and (2-1) to (2-7) at an amount corresponding to 45 mg/kg of body weight of at least one compound selected from the group consisting of ω3PUFA and their pharmaceutically acceptable salts and esters to male cynomolgus monkeys under the condition of at least 12 hours of fasting, and conducting the correction by subtracting plasma ω3PUFA concentration before the administration is at least 50 µg/mL and/or the area under the curve of the plasma ω3PUFA concentration at 0 to 12 hours after the administration is at least 400 µg·hr/mL; or the maximum plasma ω3PUFA concentration is at least 70 µg/mL and/or the area under the curve of the plasma ω3PUFA concentration at 0 to 12 hours after the administration is at least 500 µg·hr/mL.

(6-3) A self-emulsifying composition wherein the maximum plasma ω3PUFA concentration determined by orally administering the self-emulsifying composition selected from any one of the above (1-1) to (1-40) and (2-1) to (2-7) at an amount corresponding to 1800 mg of at least one compound selected from the group consisting of ω3PUFA and their pharmaceutically acceptable salts and esters to human before the meal, and conducting the correction by subtracting plasma ω3PUFA concentration before the administration is at least 50 µg/mL and/or the area under the curve of the plasma ω3PUFA concentration 2 hours after the administration is at least 10 µg/mL.

(6-4) A self-emulsifying composition wherein the maximum plasma ω3PUFA concentration determined by orally administering the self-emulsifying composition selected from any one of the above (1-1) to (1-40) and (2-1) to (2-7) at an amount corresponding to 1800 mg of at least one compound selected from the group consisting of ω3PUFA and their pharmaceutically acceptable salts and esters to human before the meal, and conducting the correction by subtracting plasma ω3PUFA concentration before the administration is at least 10 µg/mL and/or the area under the curve of the plasma ω3PUFA concentration at 0 to 72 hours after the administration is at least 250 µg·hr/mL.

The seventh aspect of the present invention is the self-emulsifying composition as described below.

(7-1) A self-emulsifying composition comprising at least one compound selected from the group consisting of ω3PUFA and their pharmaceutically acceptable salts and esters as well as lecithin and/or a polyoxyethylene sorbitan fatty acid ester as the emulsifier, which upon administration to a human satisfies at least one of the following (a) to (e) calculated by conducting the correction by subtracting the plasma ω3PUFA concentration before the administration:

(a) the maximum plasma ω3PUFA concentration is at least 50 μg/mL,
(b) the plasma ω3PUFA concentration 2 hours after the administration is at least 20 μg/mL,
(c) the time required to reach the maximum plasma ω3PUFA concentration (Tmax) is up to 6 hours,
(d) the area under the curve of the plasma ω3PUFA concentration at 0 to 72 hours after the administration is at least 500 μg·hr/mL, and
(e) the plasma ω3PUFA concentration 24 hours after the administration is 5 to 100 μg/mL.

(7-2) A self-emulsifying composition according to the above (7-1) wherein content of the at least one compound selected from the group consisting of ω3PUFA and their pharmaceutically acceptable salts and esters in the composition administered to human is 500 mg to 10000 mg.

(7-3) A self-emulsifying composition according to the above (7-1) or (7-2) wherein content of the at least one compound selected from the group consisting of ω3PUFA and their pharmaceutically acceptable salts and esters in the composition administered to human is at least one of 500 mg, 1000 mg, 1800 mg, 2000 mg, 3600 mg, 4000 mg, 6000 mg, and 8000 mg.

(7-4) A self-emulsifying composition according to any one of the above (7-1) to (7-3) wherein content of the at least one compound selected from the group consisting of ω3PUFA and their pharmaceutically acceptable salts and esters in the composition administered to human is selected from 1800 mg, 2000 mg, 3600 mg, and 4000 mg.

(7-5) A self-emulsifying composition according to any one of the above (7-1) to (7-4) wherein the ω3PUFA and their pharmaceutically acceptable salts and esters in the composition administered to human are at least one compound selected from the group consisting of EPA and its pharmaceutically acceptable salts and esters.

(7-6) A self-emulsifying composition according to the above (7-5) wherein the EPA and its pharmaceutically acceptable salts and esters are ethyl ester of EPA.

(7-7) A self-emulsifying composition according to any one of the above (7-1) to (7-6) wherein, when the composition is administered, the maximum plasma ω3PUFA concentration calculated by conducting the correction by subtracting the plasma ω3PUFA concentration before the administration is at least 50 μg/mL, and the area under the curve of the plasma ω3PUFA concentration at 0 to 72 hours after the administration is at least 500 μg·hr/mL.

(7-8) A self-emulsifying composition according to any one of the above (7-1) to (7-7) wherein, when the composition is administered, the maximum plasma ω3PUFA concentration calculated by conducting the correction by subtracting the plasma ω3PUFA concentration before the administration is at least 50 μg/mL, and the plasma ω3PUFA concentration 24 hours after the administration is 5 to 100 μg/mL.

(7-9) A self-emulsifying composition according to any one of the above (7-1) to (7-8) wherein, when the composition is administered, the maximum plasma ω3PUFA concentration calculated by conducting the correction by subtracting the plasma ω3PUFA concentration before the administration is at least 50 μg/mL, and the time required to reach the maximum plasma ω3PUFA concentration (Tmax) is up to 6 hours.

(7-10) A self-emulsifying composition according to any one of the above (7-1) to (7-9) wherein, when the composition is administered, the area under the curve of the plasma ω3PUFA concentration at 0 to 72 hours after the administration calculated by conducting the correction by subtracting the plasma ω3PUFA concentration before the administration is at least 500 μg·hr/mL, and the time required to reach the maximum plasma ω3PUFA concentration (Tmax) is up to 6 hours.

(7-11) A self-emulsifying composition according to any one of the above (7-1) to (7-10) wherein, when the composition is administered under fasting, the maximum plasma ω3PUFA concentration calculated by conducting the correction by subtracting the plasma ω3PUFA concentration before the administration is at three times as high as the maximum plasma ω3PUFA concentration immediately after the meal, or the area under the curve of the plasma ω3PUFA concentration at 0 to 72 hours after the administration is at least twice as large as the area under the curve of the plasma ω3PUFA concentration immediately after the meal.

(7-12) A self-emulsifying composition according to any one of the above (7-1) to (7-11) wherein the composition contains lecithin and a polyoxyethylene sorbitan fatty acid ester as the emulsifier.

(7-13) A self-emulsifying composition according to any one of the above (7-1) to (7-12) wherein the composition further contains polyoxyethylene castor oil as the emulsifier.

(7-14) A self-emulsifying composition according to any one of (7-1) to (7-13) wherein content of the emulsifier is 1 to 29% by weight when the total amount of the self-emulsifying composition is 100% by weight.

(7-15) A self-emulsifying composition according to any one of (7-1) to (7-14) wherein content of the lecithin is 3 to 40 parts by weight or 1 to 25 parts by weight in relation to 100 parts by weight of the at least one compound selected from the group consisting of ω3PUFA and their pharmaceutically acceptable salts and esters.

(7-16) A self-emulsifying composition according to any one of the above (7-1) to (7-15) wherein content of the polyoxyethylene castor oil is up to 120 parts by weight in relation to 100 parts by weight of the polyoxyethylene sorbitan fatty acid ester in the composition.

(7-17) A self-emulsifying composition according to any one of the above (7-1) to (7-14) wherein the composition is at least one member selected from the group consisting of therapeutic agent for dyslipidemia (hypercholesterolemia, hyper-LDL cholesterolemia, hyper-non-HDL cholesterolemia, hyper-VLDL cholesterolemia, hypo-HDL cholesterolemia, hypertriglyceridemia, hyper-ApoB-emia, hypo-ApoAI-emia, increased LDL particle number-emia, small LDL particle size-emia, hyper-oxidized LDL-emia, hyper-small dense LDL-emia, hyper-RLP-C-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-hs-CRP-emia, hypo-EPA-emia (the state wherein EPA value in plasma, serum, erythrocyte membrane, platelet membrane is low), hyper-free fatty acidemia), hyper-fasting glucose-emia, hyper-HbA1c-emia, hyper-HOMA-IR-emia, hyper-intercellular adhesion molecule-1-emia, hyper-IL-6-emia, hyper-PAI-1-emia, hypercreatininemia, hyper-AST-emia, hyper-ALT-emia, hyper-uric acidemia, hyper-8-isoprostane-emia, hyper-TXA2-emia, hyper-LTB2-emia, etc.), therapeutic agent for postprandial hyperglycemia, antiarteriosclerotic agent, platelet aggregation suppressive agent, therapeutic agent for peripheral circulatory insufficiency, agent for preventing onset of cardiovascular events, therapeutic agent for inflammatory diseases (NAFLD, NASH, etc.), anticancer agent, and preventive and therapeutic agents and progression suppressant for central diseases (depression, depressive state, obsessive-compulsive disorder, social phobia, panic disorder, etc.).

(7-18) A self-emulsifying composition according to any one of the above (7-1) to (7-17) wherein the composition containing 500 mg to 10000 mg of at least one compound selected from the group consisting of ω3PUFA and their pharmaceutically acceptable salts and esters is administered once a day.

(7-19) A self-emulsifying composition according to any one of the above (7-1) to (7-18) wherein the composition is administered under fasting, before the meal, immediately after the meal, or after the meal.

(7-20) A self-emulsifying composition according to any one of the above (7-1) to (7-19) comprising at least one compound selected from the group consisting of ω3PUFA and their pharmaceutically acceptable salts and esters, lecithin, and a polyoxyethylene sorbitan fatty acid ester and polyoxyethylene castor oil as emulsifiers, wherein content of the polyoxyethylene castor oil is up to 120 parts by weight in relation to 100 parts by weight of the polyoxyethylene sorbitan fatty acid ester in the composition, and wherein, when the composition is administered to a human at an amount in terms of the at least one compound selected from the group consisting of ω3PUFA and their pharmaceutically acceptable salts and esters of 500 mg to 10000 mg, the maximum plasma ω3PUFA concentration calculated by correcting the value by subtracting the plasma ω3PUFA concentration before the administration is at least 50 μg/mL, and the area under the curve of the plasma ω3PUFA concentration at 0 to 72 hours after the administration is at least 500 μg·hr/mL.

(7-21) A self-emulsifying composition according to any one of (7-1) to (7-20) wherein content of the at least one compound selected from the group consisting of ω3PUFA and their pharmaceutically acceptable salts and esters is 70 to 90% by weight when total amount of the self-emulsifying composition is 100% by weight.

(7-22) A self-emulsifying composition according to any one of (7-1) to (7-21) wherein content of the at least one compound selected from the group consisting of EPA and its pharmaceutically acceptable salts and esters is 70 to 90% by weight when total amount of the self-emulsifying composition is 100% by weight.

(7-23) A self-emulsifying composition according to any one of (7-1) to (7-22) wherein content of the lecithin is 3 to 40 parts by weight or 1 to 25 parts by weight in relation to 100 parts by weight of the at least one compound selected from the group consisting of ω3PUFA and their pharmaceutically acceptable salts and esters.

(7-24) A self-emulsifying composition according to any one of the above (7-1) to (7-23) wherein the composition contains water.

(7-25) A self-emulsifying composition according to any one of (7-1) to (7-24) wherein content of the water in the composition is 0.5 to 6% by weight of the total weight of the composition.

(7-26) A self-emulsifying composition according to any one of the above (7-1) to (7-25) wherein content of the ethanol in the composition is up to 4% by weight of the total weight of the composition.

f) the polyhydric alcohol is up to 4% by weight of the total weight of the composition.

(7-27) A self-emulsifying composition according to any one of the above (7-1) to (7-26) comprising, when total amount of the composition is 100% by weight,
  a) 70 to 90% by weight of EPA-E,
  b) 0.5 to 6% by weight of water,
  c) 1 to 29% by weight of a polyoxyethylene sorbitan fatty acid ester as the emulsifier, and
  d) 3 to 40 parts by weight, or 1 to 25 parts by weight of lecithin in relation to 100 parts by weight of the lecithin, wherein
  e) the ethanol and/or the polyhydric alcohol is up to 4% by weight of the total amount of the composition.

(7-28) A self-emulsifying composition according to any one of the above (7-1) to (7-27) wherein the composition is orally administered.

(7-29) A self-emulsifying composition according to any one of the above (7-1) to (7-28) wherein the composition is a composition for oral administration.

(7-30) A self-emulsifying composition according to any one of the above (7-1) to (7-29) wherein the composition is a capsule.

(7-31) A method for administrating at least one self-emulsifying composition selected from any one of the above (7-1) to (7-30) to human or a method for using such composition in human.

(7-32) A self-emulsifying composition comprising at least one compound selected from the group consisting of ω3PUFA and their pharmaceutically acceptable salts and esters, lecithin, or an emulsifier which, when administered to human, satisfies at least one of the (a) to (i) calculated by conducting the correction by subtracting the plasma ω3PUFA concentration before the administration:
  (a) the maximum plasma ω3PUFA concentration is at least 50 μg/mL,
  (b) the plasma ω3PUFA concentration 2 hours after the administration is at least 20 μg/mL,
  (c) the time required to reach the maximum plasma ω3PUFA concentration (Tmax) is up to 6 hours,
  (d) the area under the curve of the plasma ω3PUFA concentration at 0 to 72 hours after the administration is at least 500 μg·hr/mL,
  (e) the plasma ω3PUFA concentration 24 hours after the administration is 5 to 100 μg/mL,
  (f) the area under the curve of the plasma ω3PUFA concentration at 0 to 24 hours after the administration is at least 100 μg·hr/mL,
  (g) the maximum plasma ω3PUFA concentration in steady state is at least 50 μg/mL,
  (h) the minimum plasma ω3PUFA concentration in steady state is at least 10 μg/mL, and
  (i) the average ω3PUFA plasma concentration in steady state is at least 30 μg/mL.

(7-33) A self-emulsifying composition comprising at least one compound selected from the group consisting of ω3PUFA and their pharmaceutically acceptable salts and esters as well as lecithin and/or an emulsifier, which, when administered to human, satisfies at least one of the (a) to (i) calculated by conducting the correction by subtracting the plasma ω3PUFA concentration before the administration:
  (a) the maximum plasma ω3PUFA concentration is at least 50 μg/mL,
  (b) the plasma ω3PUFA concentration 2 hours after the administration is at least 20 μg/mL,
  (c) the time required to reach the maximum plasma ω3PUFA concentration (Tmax) is up to 6 hours,
  (d) the area under the curve of the plasma ω3PUFA concentration at 0 to 72 hours after the administration is at least 500 μg·hr/mL,
  (e) the plasma ω3PUFA concentration 24 hours after the administration is 5 to 100 μg/mL,
  (f) the area under the curve of the plasma ω3PUFA concentration at 0 to 24 hours after the administration is at least 100 μg·hr/mL, (g) the maximum plasma ω3PUFA concentration in steady state is at least 50 µg/mL,
(h) the minimum plasma ω3PUFA concentration in steady state is at least 10 µg/mL, and
(i) the average ω3PUFA plasma concentration in steady state is at least 30 µg/mL.

(7-34) A self-emulsifying composition according to the above (7-33) wherein the emulsifier is at least one member selected from cationic surfactants, anionic surfactants, amphoteric surfactants, and nonionic surfactants.

(7-35) A self-emulsifying composition according to the above (7-33) or (7-34) wherein the emulsifier or the nonionic surfactant is a polyoxyethylene sorbitan fatty acid ester.

(7-36) A self-emulsifying composition comprising at least one compound selected from the group consisting of ω3PUFA and their pharmaceutically acceptable salts and esters as well as lecithin and/or a polyoxyethylene sorbitan fatty acid ester as an emulsifier, which, when administered to human, satisfies at least one of the (a) to (i) calculated by conducting the correction by subtracting the plasma ω3PUFA concentration before the administration:
(a) the maximum plasma ω3PUFA concentration is at least 50 µg/mL,
(b) the plasma ω3PUFA concentration 2 hours after the administration is at least 20 µg/mL,
(c) the time required to reach the maximum plasma ω3PUFA concentration (Tmax) is up to 6 hours,
(d) the area under the curve of the plasma ω3PUFA concentration at 0 to 72 hours after the administration is at least 500 µg·hr/mL,
(e) the plasma ω3PUFA concentration 24 hours after the administration is 5 to 100 µg/mL,
(f) the area under the curve of the plasma ω3PUFA concentration at 0 to 24 hours after the administration is at least 100 µg·hr/mL,
(g) the maximum plasma ω3PUFA concentration in steady state is at least 50 µg/mL.
(h) the minimum plasma ω3PUFA concentration in steady state is at least 10 µg/mL, and
(i) the average ω3PUFA plasma concentration in steady state is at least 30 µg/mL.

(7-37) A self-emulsifying composition according to any one of the above (7-33) to (7-36) wherein content of the at least one compound selected from the group consisting of ω3PUFA and their pharmaceutically acceptable salts and esters contained in the composition to be administered to human is 500 mg to 10000 mg.

(7-38) A self-emulsifying composition according to any one of the above (7-33) to (7-37) wherein content of the at least one compound selected from the group consisting of ω3PUFA and their pharmaceutically acceptable salts and esters contained in the composition to be administered to human is at least one amount selected from 500 mg, 1000 mg, 1800 mg, 2000 mg, 3600 mg, 4000 mg, 6000 mg, and 8000 mg.

(7-39) A self-emulsifying composition according to any one of the above (7-33) to (7-38) wherein content of the at least one compound selected from the group consisting of ω3PUFA and their pharmaceutically acceptable salts and esters contained in the composition to be administered to human is at least one amount selected from 1800 mg, 2000 mg, 3600 mg, and 4000 mg.

(7-40) A self-emulsifying composition according to any one of the above (7-33) to (7-39) wherein the ω3PUFA and their pharmaceutically acceptable salts and esters contained in the composition to be administered to human are at least one member selected from the group consisting of EPA and its pharmaceutically acceptable salts and esters.

(7-41) A self-emulsifying composition according to the above (7-40) wherein the EPA and its pharmaceutically acceptable salts and esters are ethyl ester of EPA.

(7-42) A self-emulsifying composition according to any one of the above (7-33) to (7-41) wherein, upon administration of the composition, the maximum plasma ω3PUFA concentration calculated by conducting the correction by subtracting the plasma ω3PUFA concentration before the administration is at least 50 µg/mL and the area under the curve of the plasma ω3PUFA concentration at 0 to 72 hours after the administration is at least 500 µg·hr/mL.

(743) A self-emulsifying composition according to any one of the above (7-33) to (7-42) wherein, upon administration of the composition, the maximum plasma ω3PUFA concentration calculated by conducting the correction by subtracting the plasma ω3PUFA concentration before the administration is at least 50 µg/mL and the plasma ω3PUFA concentration 24 hours after the administration is 5 to 100 µg/mL.

(7-44) A self-emulsifying composition according to any one of the above (7-33) to (7-43) wherein, upon administration of the composition, the maximum plasma ω3PUFA concentration calculated by conducting the correction by subtracting the plasma ω3PUFA concentration before the administration is at least 50 µg/mL and the time required to reach the maximum plasma ω3PUFA concentration (Tmax) is up to 6 hours.

(7-45) A self-emulsifying composition according to any one of the above (7-33) to (7-44) wherein, upon administration of the composition, the area under the curve of the plasma ω3PUFA concentration at 0 to 72 hours after the administration calculated by conducting the correction by subtracting the plasma ω3PUFA concentration before the administration is at least 500 µg·hr/mL, and the time required to reach the maximum plasma ω3PUFA concentration (Tmax) is up to 6 hours.

(7-46) A self-emulsifying composition according to any one of the above (7-33) to (7-45) wherein, upon administration of the composition, the maximum plasma ω3PUFA concentration calculated by conducting the correction by subtracting the plasma ω3PUFA concentration before the administration is at least 50 µg/mL and the average ω3PUFA plasma concentration in steady state is at least 30 µg/mL.

(7-47) A self-emulsifying composition according to any one of the above (7-33) to (7-46) wherein, upon administration of the composition, the maximum plasma ω3PUFA concentration calculated by conducting the correction by subtracting the plasma ω3PUFA concentration before the administration is at least three times as high as the maximum plasma ω3PUFA concentration immediately after the meal, or the area under the curve of the plasma ω3PUFA concentration at 0 to 72 hours after the administration is at least twice as large as the area under the curve of the plasma ω3PUFA concentration immediately after the meal.

(7-48) A self-emulsifying composition according to any one of the above (7-33) to (7-47) wherein the composition contains lecithin and an emulsifier.

(7-49) A self-emulsifying composition according to any one of the above (7-33) to (7-48) wherein the composition contains lecithin and a nonionic surfactant as the emulsifier.

(7-50) A self-emulsifying composition according to any one of the above (7-33) to (7-49) wherein the composition contains lecithin and a polyoxyethylene sorbitan fatty acid ester as the emulsifier.

(7-51) A self-emulsifying composition according to any one of the above (7-33) to (7-50) wherein the composition contains lecithin and a polyoxyethylene sorbitan fatty acid ester as a nonionic surfactant.
(7-52) A self-emulsifying composition according to any one of the above (7-33) to (7-51) wherein the composition further contains polyoxyethylene castor oil as the emulsifier.
(7-53) A self-emulsifying composition according to any one of the above (7-33) to (7-52) wherein content of the emulsifier is 1 to 29% by weight when total amount of the self-emulsifying composition is 100% by weight.
(7-54) A self-emulsifying composition according to any one of the above (7-33) to (7-53) wherein content of the polyoxyethylene castor oil is up to 120 parts by weight in relation to 100 parts by weight of the polyoxyethylene sorbitan fatty acid ester in the composition.
(7-55) A self-emulsifying composition according to any one of the above (7-33) to (7-54) wherein the composition is at least one member selected from the group consisting of therapeutic agent for dyslipidemia (hypercholesterolemia, hyper-LDL cholesterolemia, hyper-non-HDL cholesterolemia, hyper-VLDL cholesterolemia, hypo-HDL cholesterolemia, hypertriglyceridemia, hyper-ApoB-emia, hypo-ApoAI-emia, increased LDL particle number-emia, small LDL particle size-emia, hyper-oxidized LDL-emia, hyper-small dense LDL-emia, hyper-RLP-C-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-hs-CRP-emia, hypo-EPA-emia (the state wherein EPA value in plasma, serum, erythrocyte membrane, platelet membrane is low), hyper-free fatty acidemia), hyper-fasting glucose-emia, hyper-HbA1c-emia, hyper-HOMA-IR-emia, hyper-intercellular adhesion molecule-1-emia, hyper-IL-6-emia, hyper-PAI-1-emia, hypercreatininemia, hyper-AST-emia, hyper-ALT-emia, hyper-uric acidemia, hyper-8-isoprostane-emia, hyper-TXA2-emia, hyper-LTB2-emia, etc.), therapeutic agent for postprandial hyperglycemia, antiarteriosclerotic agent, platelet aggregation suppressive agent, therapeutic agent for peripheral circulatory insufficiency, agent for preventing onset of cardiovascular events, therapeutic agent for inflammatory diseases (NAFLD, NASH, etc.), anticancer agent, and preventive and therapeutic agents and progression suppressant for central diseases (depression, depressive state, obsessive-compulsive disorder, social phobia, panic disorder, etc.).
(7-56) A self-emulsifying composition according to any one of the above (7-33) to (7-55) wherein the composition containing at least one compound selected from the group consisting of ω3PUFA and their pharmaceutically acceptable salts and esters at an amount of 500 mg to 10000 mg is administered once a day.
(7-57) A self-emulsifying composition according to any one of the above (7-33) to (7-56) comprising at least one compound selected from the group consisting of ω3PUFA and their pharmaceutically acceptable salts and esters, lecithin, and a polyoxyethylene sorbitan fatty acid ester and polyoxyethylene castor oil as emulsifiers wherein content of the polyoxyethylene castor oil is up to 120 parts by weight in relation to 100 parts by weight of the polyoxyethylene sorbitan fatty acid ester in the composition, and wherein, when the composition is administered to human at an amount in terms of the at least one compound selected from the group consisting of ω3PUFA and their pharmaceutically acceptable salts and esters of 500 mg to 10000 mg, the maximum plasma ω3PUFA concentration calculated by conducting the correction by subtracting plasma ω3PUFA concentration before the administration is at least 50 μg/mL and the area under the curve of the plasma ω3PUFA concentration at 0 to 72 hours after the administration is at least 500 μg·hr/mL.
(7-58) A self-emulsifying composition according to any one of the above (7-33) to (7-57) wherein content of the at least one compound selected from the group consisting of ω3PUFA and their pharmaceutically acceptable salts and esters is 70 to 90% by weight when total amount of the self-emulsifying composition is 100% by weight.
(7-59) A self-emulsifying composition according to any one of the above (7-33) to (7-58) wherein content of the at least one compound selected from the group consisting of EPA and its pharmaceutically acceptable salts and esters is 70 to 90% by weight when total amount of the self-emulsifying composition is 100% by weight.
(7-60) A self-emulsifying composition according to any one of the above (7-33) to (7-59) wherein content of the lecithin is 3 to 40 parts by weight or 1 to 25 parts by weight in relation to 100 parts by weight of the at least one compound selected from the group consisting of ω3PUFA and their pharmaceutically acceptable salts and esters.
(7-61) A self-emulsifying composition according to any one of the above (7-33) to (7-60) wherein the composition contains water.
(7-62) A self-emulsifying composition according to any one of the above (7-33) to (7-61) wherein content of the ethanol in the composition is up to 4% by weight of the total weight of the composition.
f) the polyhydric alcohol is up to 4% by weight in the total weight of the composition.
(7-63) A self-emulsifying composition according to any one of the above (7-33) to (7-62) wherein content of water in the composition is 0.5 to 6% by weight of the total weight of the composition.
(7-64) A self-emulsifying composition according to any one of the above (7-33) to (7-63) comprising, when the total composition is 100% by weight,
  a) 70 to 90% by weight of EPA-E,
  b) 0.5 to 6% by weight of water,
  c) 1 to 29% by weight of a polyoxyethylene sorbitan fatty acid ester as the emulsifier, and
  d) 3 to 40 parts by weight or 1 to 25 parts by weight of lecithin in relation to 100 parts by weight of the EPA-E, wherein
  e) content of ethanol and/or polyhydric alcohol is up to 4% by weight of the total composition.
(7-65) A self-emulsifying composition according to any one of the above (7-33) to (7-64) comprising, when the total composition is 100% by weight,
  a) 70 to 90% by weight of at least one compound selected from the group consisting of ω3PUFA and their pharmaceutically acceptable salts and esters,
  b) 0.5 to 6% by weight of water,
  c) 1 to 29% by weight of a polyoxyethylene sorbitan fatty acid ester and polyoxyethylene castor oil as emulsifiers, and
  d) 1 to 25 parts by weight of lecithin in relation to 100 parts by weight of the at least one compound selected from the group consisting of ω3PUFA and their pharmaceutically acceptable salts and esters, wherein
  e) content of ethanol and/or polyhydric alcohol is up to 4% by weight of the total amount of the composition, and f) content of polyoxyethylene castor oil is up to 120 parts by weight in relation to 100 parts by weight of the polyoxyethylene sorbitan fatty acid ester in the composition;

the composition satisfying at least one of the (a) to (i) as described below calculated by conducting the correction by subtracting ω3PUFA concentration in plasma before the administration, when the self-emulsifying composition is administered once a day at an amount in terms of the at least one compound selected from the group consisting of ω3PUFA and their pharmaceutically acceptable salts and esters of one selected from 1800 mg, 2000 mg, 3600 mg, and 4000 mg:

(a) the maximum plasma ω3PUFA concentration is at least 50 μg/mL,
(b) the plasma ω3PUFA concentration 2 hours after the administration is at least 20 μg/mL,
(c) the time required to reach the maximum plasma ω3PUFA concentration (Tmax) is up to 6 hours,
(d) the area under the curve of the plasma ω3PUFA concentration at 0 to 72 hours after the administration is at least 500 μg·hr/mL,
(e) the plasma ω3PUFA concentration 24 hours after the administration is 5 to 100 μg/mL,
(f) the area under the curve of the plasma ω3PUFA concentration at 0 to 24 hours after the administration is at least 100 μg·hr/mL,
(g) the maximum plasma ω3PUFA concentration in steady state is at least 50 μg/mL,
(h) the minimum plasma ω3PUFA concentration in steady state is at least 10 μg/mL, and
(i) the average ω3PUFA plasma concentration in steady state is at least 30 μg/mL.

(7-66) A self-emulsifying composition according to the above (7-65) wherein the at least one compound selected from the group consisting of ω3PUFA and their pharmaceutically acceptable salts and esters is the EPA-E.

(7-67) A self-emulsifying composition according to any one of the above (6-1) to (7-66) which is substantially free from at least one compound selected from the group consisting of DHA and its pharmaceutically acceptable salts and esters.

(7-68) A self-emulsifying composition according to any one of the above (7-1) to (7-67) wherein content of the at least one compound selected from the group consisting of DHA and its pharmaceutically acceptable salts and esters is up to 1% by weight of the total amount of the composition.

(7-69) A method for administering at least one self-emulsifying composition selected from the above (7-33) to (7-68) to human or using such composition in human.

(7-70) A method for administering a self-emulsifying composition comprising at least one compound selected from the group consisting of ω3PUFA and their pharmaceutically acceptable salts and esters as well as lecithin and/or a polyoxyethylene sorbitan fatty acid ester as the emulsifier, wherein the method satisfies at least one of the (a) to (i) as described below calculated by conducting the correction by subtracting ω3PUFA concentration in plasma before the administration, when the self-emulsifying composition is administered to human:

(a) the maximum plasma ω3PUFA concentration is at least 50 μg/mL,
(b) the plasma ω3PUFA concentration 2 hours after the administration is at least 20 μg/mL,
(c) the time required to reach the maximum plasma ω3PUFA concentration (Tmax) is up to 6 hours, and
(d) the area under the curve of the plasma ω3PUFA concentration at 0 to 72 hours after the administration is at least 500 μg·hr/mL,
(e) the plasma ω3PUFA concentration 24 hours after the administration is 5 to 500 μg/mL,
(f) the area under the curve of the plasma ω3PUFA concentration at 0 to 24 hours after the administration is at least 100 μg·hr/mL,
(g) the maximum plasma ω3PUFA concentration in steady state is at least 50 μg/mL,
(h) the minimum plasma ω3PUFA concentration in steady state is at least 10 μg/mL, and
(i) the average ω3PUFA plasma concentration in steady state is at least 30 μg/mL.

(7-71) A method for administering the self-emulsifying composition according to any one of the above (7-33) to (7-67) comprising, when the total composition is 100% by weight,
a) 70 to 90° % by weight of at least one compound selected from the group consisting of ω3PUFA and their pharmaceutically acceptable salts and esters,
b) 0.5 to 6% by weight of water,
c) 1 to 29% by weight of a polyoxyethylene sorbitan fatty acid ester as the emulsifier, and
d) 3 to 40 parts by weight or 1 to 25 parts by weight of lecithin in relation to 100 parts by weight of the at least one compound selected from the group consisting of ω3PUFA and their pharmaceutically acceptable salts and esters, wherein
e) content of ethanol and/or polyhydric alcohol is up to 4% by weight of the total composition,
the method satisfying at least one of the (a) to (i) as described below calculated by conducting the correction by subtracting ω3PUFA concentration in plasma before the administration, when the self-emulsifying composition is administered once a day at an amount in terms of the at least one compound selected from the group consisting of ω3PUFA and their pharmaceutically acceptable salts and esters of one selected from 1800 mg, 2000 mg, 3600 mg, and 4000 mg:

(a) the maximum plasma ω3PUFA concentration is at least 50 μg/mL,
(b) the plasma ω3PUFA concentration 2 hours after the administration is at least 20 μg/mL,
(c) the time required to reach the maximum plasma ω3PUFA concentration (Tmax) is up to 6 hours,
(d) the area under the curve of the plasma ω3PUFA concentration at 0 to 72 hours after the administration is at least 500 μg·hr/mL,
(e) the plasma ω3PUFA concentration 24 hours after the administration is 5 to 100 μg/mL,
(f) the area under the curve of the plasma ω3PUFA concentration at 0 to 24 hours after the administration is at least 100 μg·hr/mL,
(g) the maximum plasma ω3PUFA concentration in steady state is at least 50 μg/mL,
(h) the minimum plasma ω3PUFA concentration in steady state is at least 10 μg/mL, and
(i) the average ω3PUFA plasma concentration in steady state is at least 30 μg/mL.

The eighth aspect of the present invention is the self-emulsifying composition as described below.

(8-1) A self-emulsifying composition comprising at least one compound selected from the group consisting of ω3PUFA and their pharmaceutically acceptable salts and esters as well as lecithin and/or a polyoxyethylene sorbitan fatty acid ester as the emulsifier, wherein when the self-emulsifying composition is administered at an amount in terms of ω3PUFA of 500 to 2500 mg (for example, 1800 mg, 2000 mg) to each individual, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is substantially the same as the corresponding value obtained by administering 1800 mg/day of the ω3PUFA immediately after the meal.

(8-2) A self-emulsifying composition comprising at least one compound selected from the group consisting of ω3PUFA and their pharmaceutically acceptable salts and esters as well as lecithin and/or a polyoxyethylene sorbitan fatty acid ester as the emulsifier, wherein when the self-emulsifying composition is administered at an amount in terms of ω3PUFA of 500 to 2500 mg (for example, 1800 mg, 2000 mg) to each individual, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is 70 to 130% of the corresponding value obtained by administering 1800 mg/day of the ω3PUFA (for example, Epadel containing the EPA-E) immediately after the meal.

(8-3) A self-emulsifying composition comprising at least one compound selected from the group consisting of ω3PUFA and their pharmaceutically acceptable salts and esters as well as lecithin and/or an emulsifier, wherein when the self-emulsifying composition is administered at an amount in terms of ω3PUFA of 500 to 2500 mg to each individual, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum ω3PUFA plasma concentration in steady state, minimum ω3PUFA plasma concentration in steady state, and average ω3PUFA plasma concentration in steady state is substantially the same as the corresponding value obtained by administering 1800 mg/day of the ω3PUFA immediately after the meal.

(8-4) A self-emulsifying composition comprising at least one compound selected from the group consisting of ω3PUFA and their pharmaceutically acceptable salts and esters as well as lecithin and/or an emulsifier, wherein when the self-emulsifying composition is administered at an amount in terms of ω3PUFA of 500 to 10000 mg to each individual, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum ω3PUFA plasma concentration in steady state, minimum ω3PUFA plasma concentration in steady state, and average ω3PUFA plasma concentration in steady state is 70 to 130% of the corresponding value obtained by administering 1800 mg/day of the ω3PUFA (for example, Epadel containing the EPA-E) immediately after the meal.

(8-5) A self-emulsifying composition according to the above (8-3) or (8-4) wherein the emulsifier is at least one member selected from cationic surfactant, anionic surfactant, amphoteric surfactant, and nonionic surfactant.

(8-6) A self-emulsifying composition according to the above (8-5) wherein the nonionic surfactant is a polyoxyethylene sorbitan fatty acid ester.

(8-7) A self-emulsifying composition according to any one of the above (8-1) to (8-6) wherein the maximum plasma ω3PUFA concentration is at least 50 μg/mL.

(8-8) A self-emulsifying composition according to any one of the above (8-1) to (8-7) wherein the plasma ω3PUFA concentration 2 hours after the administration is at least 20 μg/mL.

(8-9) A self-emulsifying composition according to any one of the above (8-1) to (8-8) wherein the time required to reach the maximum plasma ω3PUFA concentration is up to 6 hours.

(8-10) A self-emulsifying composition according to any one of the above (8-1) to (8-9) wherein the area under the curve of the plasma ω3PUFA concentration at 0 to 72 hours after the administration is at least 500 μg·hr/mL.

(8-11) A self-emulsifying composition according to any one of the above (8-3) to (8-10) wherein the area under the curve of the plasma ω3PUFA concentration at 0 to 24 hours after the administration is at least 100 μg·hr/mL.

(8-12) A self-emulsifying composition according to any one of the above (8-3) to (8-11) wherein the maximum plasma ω3PUFA concentration in steady state is at least 50 μg·hr/mL.

(8-13) A self-emulsifying composition according to any one of the above (8-3) to (8-12) wherein the minimum plasma ω3PUFA concentration in steady state is at least 10 μg·hr/mL.

(8-14) A self-emulsifying composition according to any one of the above (8-3) to (8-13) wherein the average ω3PUFA plasma concentration in steady state is at least 30 μg·hr/mL.

(8-15) A self-emulsifying composition according to any one of the above (8-1) to (8-14) wherein the ω3PUFA and their pharmaceutically acceptable salts and esters administered are at least one member selected from the group consisting of EPA and its pharmaceutically acceptable salts and esters.

(8-16) A self-emulsifying composition according to any one of the above (8-1) to (8-15) wherein content of the at least one compound selected from the group consisting of ω3PUFA and their pharmaceutically acceptable salts and esters is 70 to 90% by weight when total amount of the self-emulsifying composition is 100% by weight.

(8-17) A self-emulsifying composition according to the above (8-15) wherein the EPA and its pharmaceutically acceptable salts and esters are ethyl ester of EPA.

(8-18) A self-emulsifying composition according to any one of the above (8-1) to (8-17) wherein content of the at least one compound selected from the group consisting of EPA and its pharmaceutically acceptable salts and esters is 70 to 90% by weight when total amount of the self-emulsifying composition is 100% by weight.

(8-19) A self-emulsifying composition according to any one of the above (8-1) to (8-18) wherein the composition contains lecithin and a nonionic surfactant as the emulsifier.

(8-20) A self-emulsifying composition according to any one of the above (8-1) to (8-19) wherein the composition contains lecithin and a polyoxyethylene sorbitan fatty acid ester as the emulsifier.
(8-21) A self-emulsifying composition according to any one of the above (8-1) to (8-20) wherein the composition contains lecithin and a polyoxyethylene sorbitan fatty acid ester as a nonionic surfactant.
(8-22) A self-emulsifying composition according to any one of the above (8-1) to (8-21) wherein the composition further contains polyoxyethylene castor oil as the emulsifier.
(8-23) A self-emulsifying composition according to any one of the above (8-1) to (8-22) wherein content of the emulsifier is 1 to 29% by weight when total amount of the self-emulsifying composition is 100% by weight.
(8-24) A self-emulsifying composition according to any one of the above (8-1) to (8-23) wherein content of the polyoxyethylene castor oil is up to 120 parts by weight in relation to 100 parts by weight of the polyoxyethylene sorbitan fatty acid ester in the composition.
(8-25) A self-emulsifying composition according to any one of the above (8-1) to (8-24) wherein the composition is administered once a day.
(8-26) A self-emulsifying composition according to any one of the above (8-1) to (8-25) wherein the composition is administered under fasting, before the meal, immediately after the meal, or after the meal.
(8-27) A self-emulsifying composition according to any one of the above (8-1) to (8-26) comprising EPA-E, lecithin, and a polyoxyethylene sorbitan fatty acid ester and polyoxyethylene castor oil as emulsifiers, wherein, when the self-emulsifying composition is administered at an amount in terms of the ω3PUFA of 1800 mg of 2000 mg to each individual once a day under fasting, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is substantially the same as the corresponding value obtained when the self-emulsifying composition is administered at a daily dose in terms of the ω3PUFA of 1800 mg immediately after the meal.
(8-28) A self-emulsifying composition according to any one of the above (8-1) to (8-27) comprising EPA-E, lecithin, and a polyoxyethylene sorbitan fatty acid ester and polyoxyethylene castor oil as emulsifiers, wherein, when the self-emulsifying composition is administered at an amount in terms of the ω3PUFA of 1800 mg or 2000 mg to each individual once a day under fasting, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is 70 to 130% of the corresponding value obtained when the self-emulsifying composition is administered at a daily dose in terms of the ω3PUFA of 1800 mg immediately after the meal.
(8-29) A self-emulsifying composition according to any one of the above (8-1) to (8-28) comprising EPA-E, lecithin, and a polyoxyethylene sorbitan fatty acid ester and polyoxyethylene castor oil as emulsifiers, wherein, when the self-emulsifying composition is administered at an amount in terms of the ω3PUFA of 500 mg to 1500 mg to each individual once a day under fasting, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is substantially the same as the corresponding value obtained when the self-emulsifying composition is administered at a daily dose in terms of the ω3PUFA of 1800 mg immediately after the meal.
(8-30) A self-emulsifying composition according to any one of the above (8-1) to (8-29) comprising EPA-E, lecithin, and a polyoxyethylene sorbitan fatty acid ester and polyoxyethylene castor oil as emulsifiers, wherein, when the self-emulsifying composition is administered at an amount in terms of the ω3PUFA of 500 to 1500 mg to each individual once a day under fasting, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is 70 to 130% of the corresponding value obtained when the self-emulsifying composition is administered at a daily dose in terms of the ω3PUFA of 1800 mg immediately after the meal.

The ninth aspect of the present invention is the method as described below.
(9-1) A method for increasing the blood ω3PUFA concentration wherein at least one compound selected from the group consisting of ω3PUFA and their pharmaceutically acceptable salts and esters is administered in combination with lecithin.
(9-2) A method for increasing the blood concentration according to the above (9-1) wherein the ω3PUFA is administered at least 500 mg/day.
(9-3) A method for increasing the blood concentration according to the above (9-1) or (9-2) wherein polyoxyethylene sorbitan fatty acid ester is administered in combination.
(9-4) A method for increasing the blood concentration according to any one of the above (9-1) to (9-3) wherein polyoxyethylene castor oil is administered in combination.
(9-5) A method for increasing the blood concentration according to any one of the above (9-1) to (9-4) wherein the emulsifier is administered in combination at an amount of 5 to 45 parts by weight in relation to 100 parts by weight of the ω3PUFA.
(9-6) A method for increasing the blood concentration according to the above (9-4) or (9-5) wherein the polyoxyethylene castor oil is administered at an amount of up to 120 parts by weight in relation to 100 parts by weight of polyoxyethylene sorbitan fatty acid ester.
(9-7) A method for increasing the blood concentration according to any one of the above (9-1) to (9-6) wherein the lecithin is administered in combination at an amount of 1 to 25 parts by weight in relation to 100 parts by weight of the ω3PUFA.
(9-8) A method for increasing the blood concentration according to any one of the above (9-1) to (9-7) wherein the ω3PUFA is administered once day.

(9-9) A method for increasing the blood concentration according to any one of the above (9-1) to (9-8) wherein the ω3PUFA is administered under fasting, before the meal, immediately after the meal, or after the meal.

(9-10) A method for increasing the blood concentration according to any one of the above (9-1) to (9-9) wherein, when the composition is administered at an amount in terms of the ω3PUFA of 500 to 10000 mg (for example, 1800 mg, 2000 mg) to each individual once a day under fasting, before the meal, immediately after the meal, or after the meal, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is substantially the same as the corresponding value obtained by administering 1800 mg/day of the ω3PUFA immediately after the meal.

(9-11) A method for increasing the blood concentration according to any one of the above (9-1) to (9-10) wherein, when the composition is administered at an amount in terms of the ω3PUFA of 500 to 10000 mg (for example, 1800 mg, 2000 mg) to each individual once a day under fasting, before the meal, immediately after the meal, or after the meal, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is 70 to 130% of the corresponding value obtained by administering 1800 mg/day of the ω3PUFA (for example, Epadel containing the EPA-E) immediately after the meal.

(9-12) A method for increasing the blood concentration according to any one of the above (9-1) to (9-9) wherein, when the composition is administered at an amount in terms of the ω3PUFA of 500 to 10000 mg (for example, 1800 mg, 2000 mg) to each individual once a day under fasting, before the meal, immediately after the meal, or after the meal, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum plasma concentration in steady state, minimum plasma concentration in steady state, and average plasma concentration in steady state is substantially the same as the corresponding value obtained by administering 1800 mg/day of the ω3PUFA immediately after the meal.

(9-13) A method for increasing the blood concentration according to any one of the above (9-1) to (9-9) wherein, when the composition is administered at an amount in terms of the ω3PUFA of 500 to 10000 mg (for example, 1800 mg, 2000 mg) to each individual once a day under fasting, before the meal, immediately after the meal, or after the meal, at least one value selected from the maximum plasma ω3PUFA concentration calculated by correcting the value by subtracting the blood ω3 concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum plasma concentration in steady state, minimum plasma concentration in steady state, and average plasma concentration in steady state is 70 to 130% of the corresponding value obtained by administering 1800 mg/day of the ω3PUFA (for example. Epadel containing the EPA-E) immediately after the meal.

(9-14) A method for increasing the blood concentration according to the above (9-1) to (9-13) wherein the maximum plasma ω3PUFA concentration is at least 50 g/mL.

(9-15) A method for increasing the blood concentration according to any one of the above (9-1) to (9-14) wherein the plasma ω3PUFA concentration 2 hours after the administration is at least 20 μg/mL.

(9-16) A method for increasing the blood concentration according to the above (9-1) to (9-15) wherein the time required to reach the maximum plasma concentration is up to 6 hours.

(9-17) A method for increasing the blood concentration according to any one of the above (9-1) to (9-16) wherein the area under the curve of the plasma ω3PUFA concentration at 0 to 72 hours after the administration is at least 500 μg·hr/mL.

(9-18) A method for increasing the blood concentration according to any one of the above (9-1) to (9-17) wherein the area under the curve of the plasma ω3PUFA concentration at 0 to 24 hours after the administration is at least 100 μg·hr/mL.

(9-19) A method for increasing the blood concentration according to any one of the above (9-1) to (9-18) wherein the maximum plasma ω3PUFA concentration in steady state is at least 50 μg·hr/mL.

(9-20) A method for increasing the blood concentration according to any one of the above (9-1) to (9-19) wherein the minimum plasma ω3PUFA concentration in steady state is at least 10 μg·hr/mL.

(9-21) A method for increasing the blood concentration according to any one of the above (9-1) to (9-20) wherein the average ω3PUFA plasma concentration in steady state is at least 30 μg·hr/mL.

The tenth aspect of the present invention is the method as described below.

(10-1) A method for reducing the side effects of ω3PUFA wherein at least one compound selected from the group consisting of ω3PUFA and their pharmaceutically acceptable salts and esters and lecithin are administered in combination.

(10-2) A method for reducing the side effects according to the above (10-1) wherein the ω3PUFA is administered at an individual daily dose of 1800 mg or 2000 mg.

(10-3) A method for reducing the side effects according to the above (10-1) or (10-2) wherein the ω3PUFA is administered at an individual daily dose of 3600 mg or 4000 mg.

(10-4) A method for reducing the side effects according to the above (10-1) wherein the ω3PUFA is administered at an individual daily dose of at least 4000 mg.

(10-5) A method for reducing the side effects according to any one of the above (10-1) to (10-4) wherein a polyoxyethylene sorbitan fatty acid ester is further administered in combination.

(10-6) A method for reducing the side effects according to any one of the above (10-1) to (10-5) wherein polyoxyethylene castor oil is further administered in combination.

(10-7) A method for reducing the side effects according to any one of the above (10-1) to (10-6) wherein 5 to 45 parts by weight of the emulsifier is administered in combination in relation to 100 parts by weight of the ω3PUFA.

(10-8) A method for reducing the side effects according to the above (10-7) wherein up to 120 parts by weight of the polyoxyethylene castor oil is administered in combination in relation to 100 parts by weight of the polyoxyethylene sorbitan fatty acid ester.

(10-9) A method for reducing the side effects according to any one of the above (10-1) to (10-8) wherein 1 to 25 parts by weight of lecithin is administered in combination with 100 parts by weight of the ω3PUFA.

(10-10) A method for reducing the side effects according to any one of the above (10-1) to (10-9) wherein the ω3PUFA is administered once a day.

(10-11) A method for reducing the side effects according to any one of the above (10-1) to (10-10) wherein the ω3PUFA is administered under fasting, before the meal, immediately after the meal, or after the meal.

(10-12) A method for reducing the side effects according to any one of the above (10-1) to (10-11) wherein, when the ω3PUFA is administered at an individual dose of 500 to 10000 mg (for example, 1800 mg, 2000 mg) once a day under fasting, before the meal, immediately after the meal, or after the meal, at least one member selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is substantially the same as the corresponding value obtained by administering 1800 mg/day of the ω3PUFA immediately after the meal.

(10-13) A method for reducing the side effects according to any one of the above (10-1) to (10-12) wherein, when the ω3PUFA is administered at an individual dose of 500 to 10000 mg (for example, 1800 mg, 2000 mg) under fasting, before the meal, immediately after the meal, or after the meal, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, and the area under the curve of the plasma ω3PUFA concentration at 0 to 72 hours after the administration is 70 to 130% of the corresponding value obtained by administering 1800 mg/day of the ω3PUFA (for example, Epadel containing the EPA-E) immediately after the meal.

(10-14) A method for reducing the side effects according to any one of the above (10-1) to (10-13) wherein, when the ω3PUFA is administered at an individual dose of 500 to 10000 mg (for example, 1800 mg, 2000 mg) once a day under fasting, before the meal, immediately after the meal, or after the meal, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum ω3PUFA plasma concentration in steady state, minimum ω3PUFA plasma concentration in steady state, and average ω3PUFA plasma concentration in steady state is substantially the same as the corresponding value obtained by administering 1800 mg/day of the ω3PUFA immediately after the meal.

(10-15) A method for reducing the side effects according to any one of the above (10-1) to (10-14) wherein, when the ω3PUFA is administered at an individual dose of 500 to 10000 mg (for example, 1800 mg, 2000 mg) under fasting, before the meal, immediately after the meal, or after the meal, at least one value selected from the maximum plasma ω3PUFA concentration calculated by correcting the value by subtracting the plasma ω3PUFA concentration before the administration, the plasma ω3PUFA concentration 2 hours after the administration, the time required to reach the maximum plasma ω3PUFA concentration, the area under the curve of the plasma ω3PUFA concentration at 0 to 72 hours after the administration, the area under the curve of the plasma ω3PUFA concentration at 0 to 24 hours after the administration, maximum ω3PUFA plasma concentration in steady state, minimum ω3PUFA plasma concentration in steady state, and average ω3PUFA plasma concentration in steady state is 70 to 130% of the corresponding value obtained by administering 1800 mg/day of the ω3PUFA (for example, Epadel containing the EPA-E) immediately after the meal.

(10-16) A method for reducing the side effects according to the above (10-1) to (10-15) wherein the maximum plasma ω3PUFA concentration is at least 50 μg/mL.

(10-17) A method for reducing the side effects according to any one of the above (10-1) to (10-16) wherein the plasma ω3PUFA concentration 2 hours after the administration is at least 20 g/mL.

(10-18) A method for reducing the side effects according to the above (10-1) to (10-17) wherein the time required to reach the maximum plasma ω3PUFA concentration is up to 6 hours.

(10-19) A method for reducing the side effects according to any one of the above (10-1) to (10-18) wherein the area under the curve of the plasma ω3PUFA concentration at 0 to 72 hours after the administration is at least 500 μg·hr/mL.

(10-20) A method for reducing the side effects according to any one of the above (10-1) to (10-19) wherein the area under the curve of the plasma ω3PUFA concentration at 0 to 24 hours after the administration is at least 100 μg·hr/mL.

(10-21) A method for reducing the side effects according to any one of the above (10-1) to (10-20) wherein the maximum plasma ω3PUFA concentration in steady state is at least 50 μg·hr/mL.

(10-22) A method for reducing the side effects according to any one of the above (10-1) to (10-21) wherein the minimum plasma ω3PUFA concentration in steady state is at least 10 μg·hr/mL.

(10-23) A method for reducing the side effects according to any one of the above (10-1) to (10-22) wherein the average ω3PUFA plasma concentration in steady state is at least 30 μg·hr/mL.

The eleventh aspect of the present invention is the self-emulsifying composition or the method as described below.

(11-1) A self-emulsifying composition or its administration method wherein, when the composition comprising at least one compound selected from the group consisting of ω3PUFA and their pharmaceutically acceptable salts and esters, as well as lecithin and/or a polyoxyethylene sorbitan fatty acid ester as the emulsifier, is administered at an individual dose of 500 to 10000 mg in terms of the ω3PUFA, the maximum plasma ω3PUFA concentration under fasting calculated by correcting the value by subtracting the plasma ω3PUFA concentration before the administration is 70 to 130% of the maximum plasma ω3PUFA concentration immediately after the meal.

(11-2) A self-emulsifying composition or its administration method wherein, when the composition comprising at least one compound selected from the group consisting of ω3PUFA and their pharmaceutically acceptable salts and esters, as well as lecithin and/or an emulsifier, is administered at an individual dose of 500 to 10000 mg in terms of the ω3PUFA, the maximum plasma ω3PUFA concentration under fasting calculated by correcting the value by subtracting the plasma ω3PUFA concentration before the administration is 70 to 130% of the maximum plasma ω3PUFA concentration immediately after the meal.

(11-3) A self-emulsifying composition or its administration method according to the above (11-1) or (11-2) wherein the emulsifier is at least one member selected from cationic surfactant, anionic surfactant, amphoteric surfactant, and nonionic surfactant.

(11-4) A self-emulsifying composition or its administration method according to the above (11-3) wherein the nonionic surfactant is a polyoxyethylene sorbitan fatty acid ester.

(11-5) A self-emulsifying composition or its administration method according to any one of the above (11-1) to (11-4) wherein the composition is administered once a day.

(11-6) A self-emulsifying composition or its administration method according to any one of the above (11-1) to (11-5) wherein the composition is administered under fasting, before the meal, immediately after the meal, or after the meal.

(11-7) A self-emulsifying composition or its administration method according to the above (11-1) to (11-6) wherein the maximum plasma ω3PUFA concentration is at least 50 μg/mL.

(11-8) A self-emulsifying composition or its administration method according to any one of the above (11-1) to (11-7) wherein the plasma ω3PUFA concentration 2 hours after the administration is at least 20 μg/mL.

(11-9) A self-emulsifying composition or its administration method according to the above (11-1) to (11-8) wherein the time required to reach the maximum plasma ω3PUFA concentration is up to 6 hours.

(11-10) A self-emulsifying composition or its administration method according to any one of the above (11-1) to (11-9) wherein the area under the curve of the plasma ω3PUFA concentration at 0 to 72 hours after the administration is at least 500 μg·hr/mL.

(11-11) A self-emulsifying composition or its administration method according to any one of the above (11-1) to (11-10) wherein the area under the curve of the plasma ω3PUFA concentration at 0 to 24 hours after the administration is at least 100 μg·hr/mL.

(11-12) A self-emulsifying composition or its administration method according to any one of the above (11-1) to (11-11) wherein the maximum plasma ω3PUFA concentration in steady state is at least 50 μg·hr/mL.

(11-13) A self-emulsifying composition or its administration method according to any one of the above (11-1) to (11-12) wherein the minimum plasma ω3PUFA concentration in steady state is at least 10 μg·hr/mL.

(11-14) A self-emulsifying composition or its administration method according to any one of the above (11-1) to (11-13) wherein the average ω3PUFA plasma concentration in steady state is at least 30 μg·hr/mL.

(11-15) A self-emulsifying composition or its administration method according to any one of the above (11-1) to (11-14) wherein the ω3PUFA and their pharmaceutically acceptable salts and esters administered are at least one member selected from the group consisting of EPA and its pharmaceutically acceptable salts and esters.

(11-16) A self-emulsifying composition or its administration method according to any one of the above (11-1) to (11-15) wherein content of the at least one compound selected from the group consisting of ω3PUFA and their pharmaceutically acceptable salts and esters is 70 to 90% by weight when total amount of the self-emulsifying composition is 100% by weight.

(11-17) A self-emulsifying composition or its administration method according to the above (11-15) wherein the EPA and its pharmaceutically acceptable salts and esters are ethyl ester of EPA.

(11-18) A self-emulsifying composition or its administration method according to any one of the above (11-1) to (11-17) wherein content of the at least one compound selected from the group consisting of EPA and its pharmaceutically acceptable salts and esters is 70 to 90% by weight wen total amount of the self-emulsifying composition is 100% by weight.

(11-19) A self-emulsifying composition or its administration method according to any one of the above (11-1) to (11-18) wherein the composition contains lecithin and a nonionic surfactant as the emulsifier.

(11-20) A self-emulsifying composition or its administration method according to any one of the above (11-1) to (11-19) wherein the composition contains lecithin and a polyoxyethylene sorbitan fatty acid ester as the emulsifier.

(11-21) A self-emulsifying composition or its administration method according to any one of the above (11-1) to (11-20) wherein the composition contains lecithin and a polyoxyethylene sorbitan fatty acid ester as the nonionic surfactant.

(11-22) A self-emulsifying composition or its administration method according to any one of the above (11-1) to (11-21) wherein the composition further contains polyoxyethylene castor oil as the emulsifier.

(11-23) A self-emulsifying composition or its administration method according to any one of the above (11-1) to (11-22) wherein content of the emulsifier is 1 to 29% by weight when total amount of the self-emulsifying composition is 100% by weight.

(11-24) A self-emulsifying composition or its administration method according to any one of the above (11-1) to (11-23) wherein content of the polyoxyethylene castor oil is up to 120 parts by weight in relation to 100 parts by weight of the polyoxyethylene sorbitan fatty acid ester in the composition.

The twelfth aspect of the present invention is the self-emulsifying composition as described below.

(12-1) A self-emulsifying composition containing at least one compound selected from the group consisting of ω3PUFA and their pharmaceutically acceptable salts and esters as well as lecithin and/or a polyoxyethylene sorbitan fatty acid ester as an emulsifier, wherein maximum plasma ω3PUFA concentration determined by administering the composition containing 3600 mg/individual of ω3PUFA and conducting the correction by subtracting the plasma ω3PUFA concentration before the administration is at least 1.2 times as high as the maximum plasma ω3PUFA concentration determined by administering the composition containing 1800 mg/individual of ω3PUFA.

(12-2) A self-emulsifying composition containing at least one compound selected from the group consisting of ω3PUFA and their pharmaceutically acceptable salts and esters as well as lecithin and/or a polyoxyethylene sorbitan fatty acid ester as an emulsifier, wherein maximum plasma ω3PUFA concentration determined by administering the composition containing 4000 mg of ω3PUFA and conducting the correction by subtracting the plasma ω3PUFA concentration before the administration is at least 1.2 times as high as the maximum plasma ω3PUFA concentration determined by administering the composition containing 2000 mg of ω3PUFA.

(12-3) A self-emulsifying composition according to the above (12-1) or (12-2) wherein the maximum plasma ω3PUFA concentration is at least 50 µg/mL.

(124) A self-emulsifying composition according to the above (12-1) to (12-3) wherein the plasma ω3PUFA concentration 2 hours after the administration is at least 20 g/mL.

(12-5) self-emulsifying composition according to any one of the above (12-1) to (12-4) wherein the time required to reach the maximum plasma ω3PUFA concentration is up to 6 hours.

(12-6) A self-emulsifying composition according to any one of to the above (12-1) to (12-5) wherein the area under the curve of the plasma ω3PUFA concentration at 0 to 72 hours after the administration is at least 500 µg·hr/mL.

(12-7) A self-emulsifying composition according to any one of the above (12-1) to (12-6) wherein the ω3PUFA and their pharmaceutically acceptable salts and esters administered are at least one member selected from the group consisting of EPA and its pharmaceutically acceptable salts and esters.

(12-8) A self-emulsifying composition according to any one of to the above (12-1) to (12-7) wherein content of the at least one compound selected from the group consisting of ω3PUFA and their pharmaceutically acceptable salts and esters is 70 to 90% by weight when total amount of the self-emulsifying composition is 100% by weight.

(12-9) A self-emulsifying composition according to the above (12-8) wherein EPA and its pharmaceutically acceptable salts and esters are ethyl ester of EPA.

(12-10) A self-emulsifying composition according to any one of the above (12-1) to (12-9) wherein content of the at least one compound selected from the group consisting of EPA and its pharmaceutically acceptable salts and esters is 70 to 90% by weight when total amount of the self-emulsifying composition is 100% by weight.

(12-11) A self-emulsifying composition according to any one of the above (12-1) to (12-10) wherein the composition contains lecithin and polyoxyethylene sorbitan fatty acid ester as the emulsifier.

(12-12) A self-emulsifying composition according to the above (12-1) to (12-11) wherein the composition further contains polyoxyethylene castor oil as the emulsifier.

(12-13) A self-emulsifying composition according to the above (12-1) to (12-12) wherein content of the polyoxyethylene castor oil is up to 120 parts by weight in relation to 100 parts by weight of the polyoxyethylene sorbitan fatty acid ester in the composition.

(12-14) A self-emulsifying composition according to any one of the above (12-1) to (12-13) wherein the content of the emulsifier is 1 to 29% by weight when total amount of the self-emulsifying composition is 100% by weight.

(12-15) A self-emulsifying composition according to any one of the above (12-1) to (12-14) wherein content of the lecithin is 3 to 40 parts by weight or 1 to 25 parts by weight in relation to 100 parts by weight of the at least one compound selected from the group consisting of ω3PUFA and their pharmaceutically acceptable salts and esters.

The thirteenth aspect of the present invention is an emulsion preparation prepared by dispersing the self-emulsifying composition in an aqueous solution as described below.

(13-1) An emulsion preparation containing at least one compound selected from the group consisting of ω3PUFA and their pharmaceutically acceptable salts and esters, as well as lecithin and/or a polyoxyethylene sorbitan fatty acid ester as an emulsifier Advantageous Effects of Invention The self-emulsifying composition of the present invention contains a small amount of water instead of the ethanol and the polyhydric alcohol in its composition. Compatibility of the composition improves by such composition, and amount of the emulsifier used can also be reduced, and accordingly, safety for animals (including human) is thereby improved. In addition, the ω3 PUFA will be included at a higher content, and this enables reduction in the amount of emulsifier used, and compliance is thereby improved.

Inclusion of the water in the composition also enables a composition without or with minimized use of the ethanol or the polyhydric alcohols, and hence, prevention of the softening of the capsule film, and deformation of the capsule.

The self-emulsifying composition of the present invention is excellent at least in one of compatibility (appearance), self-emulsifying property, dispersibility of the composition, emulsion stability, and absorbability, and it will be rapidly absorbed even if it is administered before the meal or after the low-fat meal to thereby suppress increase in the serum TG after the meal or administered before going to bed to thereby prevent essential fatty acid deficiency upon administration of the lipase inhibitor.

The self-emulsifying composition enables not only the storage at room temperature but also the storage under the conditions of low temperature (for example, 5° C.) and high temperature (for example, 40° C.) without causing separation or cloudiness of the composition, namely, with good appearance.

The self-emulsifying composition exhibits good absorption of the ω3PUFA irrespective of timing of the administration whether the administration is carried out in the fasting, before the meal, or after the low-fat meal, and the limitation for the administration timing is reduced compared to conventional ω3PUFA preparations (for example, Epadel and Lotriga) that requires the administration immediately after the meal, and absorption efficiency was not affected by the meal.

The self-emulsifying composition exhibits high absorption, and therefore, it has high therapeutic effects, and the amount of the ω3PUFA required for the treatment can be reduced.

When the ω3PUFA is administered at a high dose (for example, 4000 mg/day/individual) to gain high therapeutic effects, the excessive ω3PUFA that is not absorbed by human remains in the intestinal tract, and side effects of lower gastrointestinal tract and the like were thereby induced. In contrast, since the self-emulsifying composition of the present invention is highly absorbable, and remaining ω3PUFA staying in the intestinal tract can be reduced or eliminated, the side effects will be reduced. In addition, since the self-emulsifying composition of the present invention is absorbable even in the administration of the dose at which sole administration of the ω3PUFA would result in the saturation of the blood concentration, the blood concentration can be increased beyond the blood concentration in the sole administration of the ω3PUFA.

By administration, the self-emulsifying composition of the present invention is capable of improving (reducing) at least one parameter selected from TG, T-cho, LDL-C, non- HDL-C, VLDL-C, VLDL-TG, oxidized LDL, small dense LDL, RLP-C, ApoB, ApoCIII, lipoprotein (a), Lp-PLA2, CETP activity, hs-CRP, plasma phospholipid, free fatty acid, fasting blood glucose, HbA1c, HOMA-IR, intercellular adhesion molecule-, IL-6, PAI-1, creatinine, AST, ALT, uric acid, 8-isoprostane, TXA2 and LTB2 and the metabolites thereof (hydroxy eicosatetraenoic acid, HETE), and the like. The self-emulsifying composition of the present invention is also capable of improving (increasing) at least one parameter selected from HDL-C, apoA-I, apoA-I/ApoB ratio, EPA in the plasma, serum, erythrocyte membrane or platelet membrane. The self-emulsifying composition of the present invention is also capable of reducing the number of LDL particles, increasing LDL particle size, and improving at least one parameter selected from ApoE genotype abnormality, hemoglobin abnormality, hematocrit abnormality, thrombocyte abnormality, and the like.

The self-emulsifying composition of the present invention has at least one, preferably at least two, and more preferably all of the preferable features as described above.

DESCRIPTION OF EMBODIMENTS

Next, the present invention is described in detail.

The present invention relates to a self-emulsifying composition comprising 70 to 90% by weight in total of at least one compound selected from the group consisting of ω3 polyunsaturated fatty acid, its pharmaceutically acceptable salts, and its esters, 1 to 29% by weight of a particular emulsifying agent, and 3 to 40 parts by weight or 1 to 25 parts by weight of lecithin in relation to 100 parts by weight of the ω3 polyunsaturated fatty acid, its pharmaceutically acceptable salt, or ester, wherein the composition has low or no content of ethanol or polyhydric alcohol. The present invention also relates to a self-emulsifying preparation having such self-emulsifying composition encapsulated therein, and a pharmaceutical product, a production method, and a method of use thereof.

In the present invention, "ω3 PUFA" is a fatty acid having a plurality of carbon-carbon double bonds in the molecule, and the first double bond is at 3rd position from the end on the side of the methyl group. Typical examples include α-linolenic acid, EPA, DHA, eicosatrienoic acid, stearidonic acid, eicosatetraenoic acid, clupanodonic acid, tetracosapentaenoic acid, and nisinic acid. Unless otherwise noted, the terms "ω3 PUFA", "EPAs", "DHAs", and "fatty acids" as used in the present invention mean not only an ω3 PUFA, an EPA, a DHA, and a fatty acid but also pharmaceutically acceptable salts and esters thereof.

The ω3 PUFA used in the present invention may be a synthetic, semi-synthetic, natural ω3 PUFA, or a natural oil containing such ω3 PUFA. Examples of the natural ω3 PUFA include an extract from a natural oil containing an ω3 PUFA, a crudely purified natural oil containing an ω3 PUFA, and a highly purified natural oil containing an ω3 PUFA produced by a method known in the art. Exemplary semi-synthetic ω3 PUFAs include ω3 PUFAs produced by a microorganism or the like and the ω3 PUFAs or the natural ω3 PUFAs which have been subjected to a chemical treatment such as esterification or ester exchange. In the present invention, the ω3 PUFAs may be used alone or in combination of two or more.

In the present invention, EPAs and DHAs are the preferable examples of the ω3 PUFAs, and EPAs are more preferable. Examples of the pharmaceutically acceptable salts of the ω3 PUFA include inorganic salts such as sodium salts and potassium salts, organic salts such as benzylamine salts and diethylamine salts, salts with basic amino acids such as arginine salts and lysine salts, and exemplary esters include alkyl esters such as ethyl ester, and esters such as monoglyceride (MG), diglyceride (DG) and triglyceride (TG). Preferable examples include ethyl ester and TG ester, and the more preferred is ethyl ester. More specifically, preferable examples include EPA-E, TG ester of EPA, DHA-E, and TG ester of DHA, and among these, the more preferred are EPA-E and DHA-E, and the most preferred is EPA-E.

The ω3 PUFA used for the starting material of the self-emulsifying composition of the present invention is not particularly limited for its purity. The purity is typically such that content of the ω3 PUFAs in the total fatty acids of the composition of the present invention could be preferably at least 50% by weight, more preferably at least 70% by weight, still more preferably at least 80% by weight, still more preferably at least 90% by weight, still more preferably at least 96.5% by weight, and most preferably at least 98% by weight. The ω3 PUFAs containing the EPAs at a high purity, for example, the one with the EPAs content of at least 50% by weight in relation to the ω3 PUFAs is preferable, and the content is more preferably at least 60% by weight, still more preferably at least 70% by weight, still more preferably at least 80% by weight, still more preferably at least 90% by weight, and most preferably at least 98% by weight. In other words, the composition of the present invention preferably has a high purity of ω3 PUFAs in the total fatty acid, more preferably, a high purity of EPAs and DHAs which are ω3 PUFAs, and most preferably an EPA purity with substantially no DHA or with the DHA of, for example less than 1.0% by weight, preferably less than 0.5% by weight, and more preferably less than 0.2% by weight For example, when EPA-E and DHA-E are used, compositional ratio of EPA-E/DHA-E and content of (EPA-E+DHA-E) in relation to total fatty acid are not particularly limited as long as the purity of EPA-E in the composition of the present invention is in the range as described above. However, the compositional ratio of the EPA-E/DHA-E is preferably at least 0.8, more preferably at least 1.0, and most preferably at least 1.2.

The composition of the present invention may also contain a polyunsaturated fatty acid other than the ω3 PUFA such as linoleic acid, γ linolenic acid, or dihomo-γ-linolenic acid or the pharmaceutically acceptable salt or ester thereof. However, content of arachidonic acid or the pharmaceutically acceptable salt or ester thereof is preferably low, more preferably less than 2% by weight, still more preferably less than 1% by weight, and most preferably, the composition is substantially free from the arachidonic acid or the pharmaceutically acceptable salt or ester thereof.

In the self-emulsifying composition of the present invention, content of the ω3 PUFA is 50 to 95% by weight, 60 to 92% by weight, 70 to 90% by weight, and preferably 70 to 86% by weight, more preferably 72 to 85% by weight, and still more preferably 74 to 84% by weight. The ω3PUFAs used may comprise a single compound or a mixture of two or more compounds. In the case of the mixture of two or more compounds, total content of the mixture is 70 to 90% by weight of the self-emulsifying composition.

The ω3 PUFA used may be a soft capsule containing the EPA-E at a high purity (at least 96.5% by weight) (product name, Epadel; manufactured by Mochida Pharmaceutical Co., Ltd.) commercially available in Japan as a therapeutic agent for ASO and hyperlipidemia or a high purity EPA-E containing capsule (product name, VASCEPA; Amarin) commercially available in the U.S. as a therapeutic agent for hypertriglyceridemia. The ω3 PUFA used may also be a mixture of EPA-E and DHA-E, for example, Lovaza (Registered Trademark) (a soft capsule containing about 46.5% by weight of EPA-E and about 37.5% by weight of DHA-E from GlaxoSmithKline) commercially available in the U.S. as a therapeutic agent for hypertriglyceridemia or LOTRIGA (Registered Trademark) (a soft capsule containing about 46.5% by weight of EPA-E and about 37.5% by weight of DHA-E from Takeda Pharmaceutical Co., Ltd.) commercially available in Japan. The mixture of EPA and DHA used may be, for example, EPANOVA (Registered Trademark) (a soft capsule containing about 50 to 60% by weight of EPA free acid and about 15 to 25% by weight of DHA free acid from AstraZeneca) commercially available in the U.S. as a therapeutic agent for hypertriglyceridemia.

Purified fish oils may also be used for the ω3 PUFA, and uses of monoglyceride (MG), diglyceride (DG), and TG derivatives and combinations thereof as the ω3 PUFA are also preferable embodiments. Various products containing the ω3 PUFA are commercially available, for example, Incromega F2250, F2628, E2251, F2573, TG2162, TG2779, TG2928, TG3525, and E5015 (Croda International PLC, Yorkshire, England), and EPAX6000FA, EPAX5000TG, EPAX4510TG, EPAX2050TG, EPAX7010EE, K85TG, K85EE, and K80EE (Pronova Biopharma, Lysaker, Norway). These products may be purchased and used for the composition of the present invention.

In the present invention, the "polyoxyethylene sorbitan fatty acid ester" is polyoxyethylene ether of a fatty acid ester wherein a part of the hydroxy groups of anhydrous sorbitol have been esterified with a fatty acid. Various compounds with different esterifying fatty acids are commercially available, and examples include polyoxyethylene (20) sorbitan monolaurate (NIKKOL TL-10, polysorbate 20, Tween 20), polyoxyethylene (20) sorbitan monopalmitate (NIKKOL TP-10V, Polysorbate 40, Tween 40), polyoxyethylene (20) sorbitan monostearate (NIKKOL TS-10MV, polysorbate 60, Tween 60), polyoxyethylene (20) sorbitan tristearate (NIKKOL TS-30V, polysorbate 65), polyoxyethylene (20) sorbitan monoisostearate (NIKKOL TI-10V), polyoxyethylene (20) sorbitan monooleate (NIKKOL TO-10MV, polysorbate 80, Tween 80), and polyoxyethylene (20) sorbitan trioleate (NIKKOL TO-30V, polysorbate 85), and the preferred are polyoxyethylene (20) sorbitan monooleate, polyoxyethylene (20) sorbitan monooleate, and polyoxyethylene (20) sorbitan trioleate, and the more preferred is polyoxyethylene (20) sorbitan monooleate.

These may be used alone or in combination of two or more. The term "polyoxyethylene sorbitan fatty acid ester" as used in the present invention means all of such compounds.

Content of the polyoxyethylene sorbitan fatty acid ester in the self-emulsifying composition of the present invention is not particularly limited as long as the merits of the present invention are not adversely affected. The content is generally 1 to 29% by weight, preferably 3 to 20% by weight, more preferably 5 to 15% by weight, and most preferably 5 to 9% by weight when the total amount of the self-emulsifying composition is 100% by weight.

In the present invention, the "polyoxyethylene castor oil" is a compound prepared by addition polymerization of ethylene oxide to castor oil. Various compounds with different average ethylene oxide mole numbers are commercially available, and examples include NIKKOL CO-3 (Nikko Chemicals Co., Ltd.) with an average ethylene oxide mole number of 3, NIKKOL CO-10 (Nikko Chemicals Co., Ltd.) with an average ethylene oxide mole number of 10, EMALEX C-20 (Nippon Emulsion Co., Ltd.) with an average ethylene oxide mole number of 20, EMALEX C-30 (Nippon Emulsion Co., Ltd.) with an average ethylene oxide mole number of 30, Kolliphor EL (BASF) (polyoxyl 35 castor oil) with an average ethylene oxide mole number of 35, EMALEX C-40 (Nippon Emulsion Co., Ltd.) with an average ethylene oxide mole number of 40, and EMALEX C-50 (Nippon Emulsion Co., Ltd.) with an average ethylene oxide mole number of 50, and the preferred is Kolliphor EL. These may be used alone or in combination of two or more. The term "polyoxyethylene castor oil" as used in the present invention means all of such compounds unless otherwise noted.

Content of the polyoxyethylene castor oil in the self-emulsifying composition of the present invention is not particularly limited in the present invention as long as the merits of the present invention are not adversely affected. The content is generally 1 to 20% by weight, preferably 2 to 15% by weight, more preferably 3 to 10% by weight, and most preferably 5 to 9% by weight when the total amount of the self-emulsifying composition is 100% by weight. The content of the polyoxyethylene castor oil in relation to 100 parts by weight of the polyoxyethylene sorbitan fatty acid ester in the composition is preferably up to 150 parts by weight, preferably up to 140 parts by weight, more preferably up to 130 parts by weight, still more preferably up to 120 parts by weight, particularly preferably up to 110 parts by weight, and most preferably up to 100 parts by weight. The polyoxyethylene sorbitan fatty acid ester and the polyoxyethylene castor oil are preferably incorporated so that content ratio of the polyoxyethylene sorbitan fatty acid ester to the polyoxyethylene castor oil in the composition is 100 parts by weight: 5 to 150 parts by weight, preferably 100 parts by weight: 10 to up to 140 parts by weight, more preferably 100 parts by weight: 20 to up to 130 parts by weight and still more preferably 30 to 120 parts by weight, still more preferably 100 parts by weight: 50 to 110 parts by weight, and most preferably 100 parts by weight: 80 to 120 parts by weight.

In the present invention, the "polyoxyethylene hydrogenated castor oil" is a compound prepared by hydrogenating castor oil with hydrogen, and subjecting the resulting hydrogenated castor oil to addition polymerization with ethylene oxide. Various compounds having different average degrees of polymerization of ethylene oxide are commercially available, and examples include polyoxyethylene (20) hydrogenated castor oil (NIKKOL HCO-20, Nikko Chemicals Co., Ltd.), polyoxyethylene (40) hydrogenated castor oil (NIKKOL HCO-40, Nikko Chemicals Co., Ltd.), polyoxyethylene (50) hydrogenated castor oil (NIKKOL HCO-50, Nikko Chemicals Co., Ltd.), polyoxyethylene (60) hydrogenated castor oil (NIKKOL HCO-60, Nikko Chemicals Co., Ltd.), and polyoxyethylene (100) hydrogenated castor oil (NIKKOL HCO-100, Nikko Chemicals Co., Ltd.), and the preferred is, for example, polyoxyethylene (60) hydrogenated castor oil. These may be used alone or in combination of two or more. Unless otherwise noted, the term "polyoxyethylene hydrogenated castor oil" of the present invention includes all of such compounds.

Content of the polyoxyethylene hydrogenated castor oil in the self-emulsifying composition of the present invention is not particularly limited as long as the intended merits of the present invention is realized. The content, however, is generally 1 to 20% by weight, preferably 2 to 15% by weight, more preferably 3 to 10% by weight, and most preferably 5 to 9% by weight when the total amount of the self-emulsifying composition is 100% by weight. In addition, the polyoxyethylene hydrogenated castor oil is preferably incorporated in the composition at a proportion in relation to 100 parts by weight of the polyoxyethylene sorbitan fatty acid ester of up to 150 parts by weight, preferably up to 140 parts by weight, more preferably up to 130 parts by weight, still more preferably up to 120 parts by weight, still more preferably up to 110 parts by weight, and most preferably up to 100 parts by weight. The polyoxyethylene sorbitan fatty acid ester and the polyoxyethylene castor oil are preferably incorporated so that content ratio of the polyoxyethylene sorbitan fatty acid ester to the polyoxyethylene castor oil in the composition is 100 parts by weight: 5 to 150 parts by weight, preferably 100 parts by weight: 10 to up to 140 parts by weight, more preferably 100 parts by weight: 20 to up to 130 parts by weight and still more preferably 30 to 120 parts by weight, still more preferably 100 parts by weight: 50 to 110 parts by weight, and most preferably 100 parts by weight: 80 to 120 parts by weight.

In the present invention, the term "emulsifier" includes surfactants. The surfactant may be selected from cationic surfactant, anionic surfactant, amphoteric surfactant, nonionic surfactant, and the like, and the preferred is nonionic surfactant. Exemplary known nonionic surfactants include polyoxyethylene sorbitan fatty acid ester, sorbitan fatty acid ester, glycerin fatty acid ester, sucrose fatty acid ester, polyoxyethylene castor oil, and polyoxyethylene hydrogenated castor oil.

The self-emulsifying composition of the present invention has the characteristic feature in that it contains the polyoxyethylene sorbitan fatty acid ester as the emulsifier. In one of the preferred embodiments of the present invention, the composition contains polyoxyethylene sorbitan fatty acid ester and polyoxyethylene castor oil and/or polyoxyethylene hydrogenated castor oil as the emulsifiers. In another preferred embodiment of the present invention, the composition contains polyoxyethylene sorbitan fatty acid ester and polyoxyethylene castor oil as the emulsifiers. The self-emulsifying composition of the present invention may contain an emulsifier other than polyoxyethylene sorbitan fatty acid ester and polyoxyethylene castor oil for the emulsifier, and the content is up to 20 parts by weight, more preferably up to 10 parts by weight, still more preferably less than 5 parts by weight, and most preferably substantially zero when total content of the emulsifier used in the composition is 100 parts by weight. The emulsifier which may be additionally incorporated is not particularly limited as long as at least one of the problems as described above can be solved, and examples include sorbitan fatty acid ester, glycerin fatty acid ester, polyoxyethylene hydrogenated castor oil, propylene glycol fatty acid ester, saturated polyglycolated glyceride, polyoxyethylene polyoxypropylene glycol, sucrose fatty ester, polyethylene glycol fatty acid ester, tocopherol-polyethylene glycol-succinic acid ester (TPGS), and the like.

The total content of the emulsifier in the self-emulsifying composition of the present invention is not particularly limited as long as the intended effects of the present invention are realized. However, when the total amount of the self-emulsifying composition is 100% by weight, the total content of the emulsifier is 1 to 29% by weight, preferably 3 to 27% by weight, more preferably 5 to 27% by weight, still more preferably 5 to 24% by weight, and most preferably 10 to 20% by weight. Alternatively, the total content is preferably 8 to 27% by weight, and more preferably 10 to 27% by weight. In addition, the total content in relation to 100 parts by weight of the ω3PUFA is 5 to 45 parts by weight, preferably 10 to 45 parts by weight, more preferably 15 to 35 parts by weight, and most preferably 15 to 20 parts by weight.

The composition and the pharmaceutical preparation of the present invention contain a small amount of water. Addition of water to a composition containing a hydrophobic lipid is generally conceived as a loss of compatibility. Presence of water in the composition results in the improved compatibility of the composition, and the use of the polyhydric alcohol and the ethanol becomes unnecessary. In other words, a product having transparent appearance which is free from the problem of separation or cloudiness of the composition is produced without using the polyhydric alcohol or the ethanol.

The small amount of water may be added during the preparation of the self-emulsifying composition, and the water in the gelatin capsule film may transfer to the self-emulsifying composition after the encapsulation of the self-emulsifying composition in the gelatin capsule.

In addition, the composition free from the polyhydric alcohol and the ethanol neither causes the capsule to be softened or deformed after the encapsulation, nor has side effects of the ethanol on alcohol intolerance patients taking the composition.

The water is preferably used at an amount of 0.5 to 6% by weight, more preferably at 0.5 to 4% by weight, more preferably at 0.5 to 3% by weight, and most preferably at 1 to 3% by weight when the total amount of the self-emulsifying composition is 100% by weight. Alternatively, the water is preferably used at an amount of at least 0.5% by weight and less than 3% by weight, and more preferably at least 0.5% by weight and less than 1.5% by weight.

In the present invention, the "lecithin" is one type of glycerophospholipid, and examples include soybean lecithin, zymolytic soybean lecithin, hydrogenated soybean lecithin, soybean phospholipid, purified soybean phospholipid, hydrogenated soybean phospholipid, egg yolk lecithin, egg yolk phospholipid, hydrogenated phospholipid, phospholipid from milk, high purity synthetic phospholipid, unsaturated phospholipid, lysolecithin, phospholipid premix, phosphatidic acid, phosphatidylethanolamine, phosphatidylcholine (purified phosphatidylcholine, purified egg yolk phosphatidylcholine, hydrogenated phosphatidylcholine, polyenephosphatidylcholine, and hydrogenated purified egg yolk phosphatidylcholine), phosphatidylserine, phosphatidylglycerol (purified phosphatidylglycerol, purified egg yolk phosphatidylglycerol, hydrogenated phosphatidylglycerol), phosphatidylinositol, cardiolipin, α-glycerophosphocholine, and purified egg yolk sphingomyelin. The preferred are soybean lecithin, zymolytic soybean lecithin, hydrogenated soybean lecithin, and egg yolk lecithin, and the more preferred is soybean lecithin. These may be used alone or in combination of two or more. The term "lecithin" as used in the present invention means all of such glycerophospholipids unless otherwise noted. In the present invention, lecithin is not included in the emulsifier (namely, not in the "emulsifier" as the constituent of the invention, and not taken into account in the calculation of the content of the emulsifier in the composition).

Various products of lecithins are commercially available, and exemplary such products include purified soybean lecithin (Nisshin Oilio), purified egg yolk lecithin (Asahi Kasei Pharma Corporation), and egg yolk lecithin PL-100M (Kewpie Corporation). Exemplary soybean lecithins include BASIS LP-20B (Nisshin Oil Mills, Ltd.) and Lipoid S45 and S20 (Lipoid), and exemplary zymolytic lecithins include BASIS LP-20E (Nisshin Oil Mills, Ltd.) and Phospholipon RLPC20 (Lipoid). Various such commercially available products may be used in the composition.

The content of the lecithin added in the self-emulsifying composition of the present invention is not particularly limited. The content in relation to 100 parts by weight of the ω3PUFAs is, however, preferably 0.5 to 40 parts by weight, more preferably 1 to 40 parts by weight, still more preferably 2 to 40 parts by weight, still more preferably 3 to 40 parts by weight, still more preferably 3 to 30 parts by weight, still more preferably 3 to 25 parts by weight, still more preferably 3 to 20 parts by weight, still more preferably 3.2 to 17 parts by weight, still more preferably 3.5 to 15 parts by weight, and still more preferably 3.7 to 17 parts by weight. Alternatively, the content is preferably 3 to 15 parts by weight, more preferably 3 to 12 parts by weight, and still more preferably 3 to 10 parts by weight. Most preferably, the content is 5 to 10 parts by weight.

The content of the lecithin is preferably 2.1 to 36% by weight, more preferably 2.1 to 20% by weight, and still more preferably 2.1 to 15% by weight when the total amount of the self-emulsifying composition is 100% by weight. Alternatively, the content is preferably 0.5 to 30% by weight, more preferably 1 to 25% by weight, still more preferably 1 to 20% by weight, and still more preferably 2 to 15% by weight. Most preferably, the content is 2.1 to 10% by weight.

The content of the lecithin is preferably 10 to 75 parts by weight, more preferably 11 to 60 parts by weight, still more preferably 20 to 55 parts by weight, and most preferably 25 to 35 parts by weight when the total content of the emulsifier in the self-emulsifying composition is 100 parts by weight.

The content of the lecithin is preferably 10 to 150 parts by weight, more preferably 20 to 120 parts by weight, and still more preferably 40 to 90 parts by weight when the total content of the polyoxyethylene sorbitan fatty acid ester in the self-emulsifying composition is 100 parts by weight. Most preferably, the content is 50 to 70 parts by weight.

In the present invention, the "polyhydric alcohol" is a polyol compound having the structure of a straight chain or cyclic aliphatic hydrocarbon wherein two or more carbon atoms are each substituted with one hydroxy group. Exemplary such polyhydric alcohols include divalent alcohols such as ethylene glycol, propylene glycol, trimethylene glycol, 1,2-butylene glycol, tetramethylene glycol, 1,3-butylene glycol, 2,3-butylene glycol, and pentamethylene glycol; trivalent alcohols such as glycerin, trimethylolpropane, and 1,2,6-hexane triol; and polyhydric alcohol polymers such as diethylene glycol, dipropylene glycol triethylene glycol, polyethylene glycol, polypropylene glycol, and polyglycerin, and the preferred is propylene glycol or glycerin. The glycerin also includes concentrated glycerin. The term "polyhydric alcohol" as used in the present invention means all of such polyol compounds unless otherwise noted.

Content of the polyhydric alcohol added in the self-emulsifying composition of the present invention is such an amount that the capsule is not deformed when the composition is filled in the capsule. For example, the content of the polyhydric alcohol in the composition is preferably not more than 4% by weight when the total composition is 100% by weight. Content of the polyhydric alcohol in the composition is preferably up to 4% by weight, more preferably up to 3% by weight, even more preferably up to 2% by weight, still more preferably up to 1% by weight, and most preferably 0% by weight.

Content of the ethanol in the self-emulsifying composition of the present invention is preferably such an amount that change in the quality is not induced during the encapsulation, distribution, or storage, and denaturing of the capsule content is not induced. Also, the ethanol content is preferably not exceed the daily experientially allowable medical dose. For example, the content of the ethanol in the composition is preferably not more the 4% by weight when the total composition is 100% by weight. Content of the ethanol in the composition is preferably up to 4% by weight, more preferably up to 3% by weight, even more preferably up to 2% by weight, still more preferably up to 1% by weight, and most preferably 0% by weight.

When the ethanol and the polyhydric alcohol are contained in the self-emulsifying composition, the total content of the ethanol and the polyhydric alcohol in the composition is preferably not more than 4% by weight when the total amount of the composition is 100% by weight. In the preferred embodiment, the composition contains substantially no ethanol and no polyhydric alcohol. Total content of the ethanol and the polyhydric alcohol in the composition is preferably up to 4% by weight, more preferably up to 3% by weight, even more preferably up to 2% by weight, still more preferably up to 1% by weight, and most preferably 0% by weight.

Preferable ethanol concentration may be determined based on the ω3 PUFA concentration of the self-emulsifying composition and the daily dose of the self-emulsifying composition. When the self-emulsifying composition of the present invention is orally administered to each individual at a daily dose of 1800 mg in terms of ω3 PUFA, and a preparation containing the ω3 PUFA, for example, at an amount of 75% by weight is prepared, the ethanol dose will not exceed 3.26 mg which is daily maximum dose described in the "Dictionary of Pharmaceutical Additives" when the ethanol concentration is up to 0.135% by weight.

For the self-emulsifying composition of the present invention containing such ω3 PUFA and emulsifier as described above, a preferred embodiment is the combination containing 1) EPA-E and/or DHA-E, 2) water, 3) a polyoxyethylene sorbitan fatty acid ester as an emulsifier, and 4) lecithin. When the total amount of the self-emulsifying composition is 100% by weight, the EPA-E and/or DHA-E 1) is 70 to 90% by weight, the water 2) is 0.5 to 6% by weight, the emulsifier including the polyoxyethylene sorbitan 3) is 1 to 29% by weight (excluding the lecithin), and the lecithin 4) is 3 to 40 parts by weight in relation to 100 parts by weight of the EPA-E and/or DHA-E. Another preferred embodiment is the combination containing 1) EPA-E and/or DHA-E, 2) water, 3) a polyoxyethylene sorbitan fatty acid ester as the emulsifier, 4) polyoxyl castor oil, and 5) lecithin. When the total amount of the self-emulsifying composition is 100% by weight, the EPA-E and/or DHA-E 1) is 70 to 90% by weight, the water 2) is 0.5 to 6% by weight the emulsifier including the polyoxyethylene sorbitan 3) and the polyoxyl castor oil (excluding the lecithin) is 1 to 29% by weight, and the lecithin 4) is 3 to 40 parts by weight in relation to 100 parts by weight of the EPA-E and/or DHA-E. Another preferred embodiment is the combination containing 1) at least one compound selected from ω3PUFAs and their pharmaceutically acceptable salts and esters, 2) water, 3) a polyoxyethylene sorbitan fatty acid ester and polyoxyethylene castor oil as the emulsifier, and 4) lecithin. When the total amount of the self-emulsifying composition is 100% by weight, the at least one compound selected from ω3PUFAs and their pharmaceutically acceptable salts and esters 1) is 70 to 90% by weight, the water 2) is 0.5 to 6% by weight, the emulsifier including the polyoxyethylene sorbitan fatty acid ester and polyoxyethylene castor oil 3) is 5 to 24% by weight, with the polyoxyethylene castor oil being up to 120 parts by weight in relation to 100 parts by weight of the polyoxyethylene sorbitan fatty acid ester, and the lecithin 4) is 3 to 40 parts by weight in relation to 100 parts by weight of the at least one compound selected from ω3PUFAs and their pharmaceutically acceptable salts and esters.

The self-emulsifying composition of the present invention may be encapsulated in a capsule. The capsule selected may be a hard capsule or a soft capsule, and preferably, the capsule used is a soft capsule. The soft capsule is not particularly limited in shape, and preferably, the soft capsule is a rotary die type soft capsule or a seamless capsule.

In the soft capsule of the present invention, the capsule film is not necessarily limited for its composition, and exemplary main ingredients include gelatin, carageenan, pectin, pullulan, sodium arginate, starch, hypromellose, hydroxy propyl cellulose, and other known ingredients. The preferred is gelatin, and the type of gelatin used is not particularly limited. Exemplary gelatins include acid-treated gelatin, alkali-treated gelatin, amphoteric gelatin, chemically modified gelatin, and other known gelatins, which may be used alone or in combination of two or more. The gelatin used is preferably an acid-treated gelatin or alkali-treated gelatin. The source of the gelatin is not necessarily limited, and the gelatin used may be the one from cattle bone, cattle skin, pig bone, pig skin, fish scale, or fish skin, and preferably, the one from cattle bone, cattle skin, pig bone, or pig skin.

The "gelatin" used may be the one normally used in the production of a soft capsule, for example, medical gelatin (gelatin and purified gelatin) defined in The Japanese Pharmacopoeia 16th edition. The gelatin may also be a combination of two or more types, and the capsule film may also contain other components such as a plasticizing agent.

The "plasticizing agent" added to the capsule film may be the one normally used in the production of a soft capsule, with preferred examples including a polyhydric alcohol such as glycerin (for example, concentrated glycerin), ethylene glycol, polyethylene glycol, propylene glycol, or polypropylene glycol, and a sugar alcohol such as sorbitol, mannitol, or xylitol. These plasticizing agents may be used in combination of two or more. Particularly preferred are glycerin and sorbitol. Also preferred is a combination of glycerin and sorbitol, and in this case, the glycerin and the sorbitol may be used at a weight ratio in the range of 1:5 to 5:1, and more preferably 1:3 to 3:1.

In the soft capsule preparation, and in particular, in the seamless capsule of the present invention, the capsule film solution preferably contains the gelatin and the plasticizing agent at a weight ratio in the range of 10:1 to 1:10, and more preferably of 10:1 to 1:1.

The weight ratio between the capsule film solution and the capsule content is typically 10:1 to 1:10, and preferably 3:1 to 1:10.

If desired, the capsule film may also contain various additives commonly used in the capsule film. Exemplary such additives include amino acids, citric acid, glycerin, sorbitol, trehalose, and other plasticizing agents, antiseptic, dye, titanium oxide, and other colorants, and organic acids.

The composition for the capsule film may be prepared by dissolving gelatin, the plasticizing agent, and the optional additives in water at room temperature or at an elevated temperature.

A capsulated self-emulsifying preparation having the self-emulsifying composition of the present invention as its liquid content preferably has high hardness immediately after the production, and this hardness is preferably maintained during the storage. Loss of the hardness is unfavorable in view of the quality because the loss of the hardness does not only result in the deformation but also fragileness and breakage of the capsule and bleeding of the content. Softening of the capsule can be detected by measuring the hardness with a common hardness tester.

The capsulated self-emulsifying preparation of the present invention has the hardness immediately after the production of at least 18 kgf, preferably at least 20 kgf, and more preferably at least 22 kgf. It is desirable that the hardness of the preparation does not substantially decrease, or not decrease by 6 kgf or more when the preparation is stored in a tightly sealed aluminum package at 40° C. for 1 week compared with the hardness immediately after the production. Preferably, the inventive preparation has a hardness of at least 10 kgf, more preferably of at least 15 kgf, and even more preferably of at least 20 kgf after the storage at 40° C. for 1 week.

With the hardness immediately after the production being assumed to be 100%, at least 60%, preferably at least 70%, more preferably at least 80%, even more preferably at least 85%, and most preferably at least 90% thereof is maintained after the storage in a tightly sealed aluminum package at 40° C. for 1 week.

The dose and dosage period of the ω3 PUFA used in the self-emulsifying composition of the present invention are made sufficient for realizing the intended action, and can be adequately adjusted depending on the administration route, frequency of administration per day, seriousness of the symptoms, body weight, age, and other factors.

In the case of oral administration, the composition is administered one to three times a day at an EPA-E dose, for instance, per individual of 10 to 12000 mg/day, 50 to 10000 mg/day, preferably 50 to 8000 mg, 100 to 5000 mg/day, 100 to 4000 mg/day, more preferably 200 to 3000 mg/day, 300 to 3000 mg/day, and still more preferably 500 to 3000 mg/day; or administered one to three times a day at an EPA-E dose per individual of 500 to 10000 mg/day, 500 to 4500 mg/day, 1500 to 4200 mg/day, and preferably 1500 to 2400 mg/day, 3300 to 4200 mg/day, 7000 to 8100 mg/day. The administration may be conducted one time at the entire dose or several times at divided doses as required. The composition may be administered one to three times a day at an EPA-E dose per individual of 1800 mg, 2000 mg, 2700 mg, 3000 mg, 3600 mg, 4000 mg, 6000 mg, 800 mg or 10000 mg, with the administration being conducted one time at the entire dose or several times at divided doses as required. Tolerance of the daily dose or one divided dose as described above is ±5%. The frequency of administration per day is preferably one time a day or two or three times a day. In the case of one time administration per day, one to ten capsules, preferably one to eight capsules, more preferably one to six capsules, still more preferably one to four capsules, and even more preferably one to three capsules as soft capsules each containing 1000 mg of EPA-E, for instance, can be administered. Soft capsules each containing 100 mg of EPA-E may be combined with soft capsules each containing 500 mg of the ester so as to administer the composition at an EPA-E dose of 500 mg, 1500 mg, 2500 mg, 3500 mg, 4500 mg or 5500 mg/administration. While administration of EPA-E during to after meals is deemed preferable, and administration immediately after meals (within 30 minutes after meals) more preferable, because the absorption of EPA-E is influenced by diet, the self-emulsifying composition of the present invention has an excellent absorbability under fasting, and therefore, it exerts the intended effects even when administered at a timing other than during, after or immediately after meals, for example, under fasting (at least 8 hours, and preferably at least 10 hours after the last meal), before or immediately before meals, between meals, or at bedtime; when administered to patients with reduced absorption ability of the intestinal tract (for example, elderly, patients of intestinal disease, patients after intestinal surgery, terminal cancer patients, or patients taking a lipase inhibitor); or when administered at a reduced dose.

The self-emulsifying composition of the present invention is preferably characterized in that the time until the maximum plasma ω3 PUFA concentration is attained after the oral administration is comparable to or shorter than that found for the ω3 PUFA stock solution. Otherwise, the inventive composition is preferably characterized in that the maximum plasma ω3 PUFA concentration is higher than that found for the ω3 PUFA stock solution (a composition containing the ω3 PUFA in the same amount as the self-emulsifying composition of the present invention but not containing the emulsifier and the like). In addition, the inventive composition is preferably characterized in that the plasma ω3 PUFA concentration two hours after the administration, the area under the plasma ω3 PUFA concentration vs time curve from zero to two hours after the administration, and/or the area under the plasma ω3 PUFA concentration vs time curve from zero to 72 hours after the administration is comparable to or higher than that found for the ω3 PUFA stock solution. More preferably, the self-emulsifying composition of the present invention is characterized in that the time until the maximum plasma ω3 PUFA concentration is attained is short, such maximum concentration is high, and both the plasma concentration two hours after the administration and the area under the plasma ω3 PUFA concentration vs time curve from zero to two hours and/or from zero to 72 hours after the administration are high as compared with those for the ω3 PUFA stock solution, respectively. Most preferably, the above parameters of the self-emulsifying composition of the present invention are higher than those obtained in the case when the ω3 PUFA stock solution is administered immediately after meals.

Such pharmacokinetics as above can be confirmed with dogs, monkeys or other animals, and preferably by examination on humans.

In a pharmacokinetic study conducted by orally administering the self-emulsifying composition to male beagles as fasted for at least 18 hours at an ω3 PUFA dose per individual of 600 mg, the maximum plasma ω3 PUFA concentration is, for instance, preferably at least 50 μg/mL, more preferably at least 60 μg/mL, and even more preferably at least 70 μg/mL, as calculated with correction by subtraction of the plasma ω3 PUFA concentration before the administration of the composition. The area under the plasma ωω3 PUFA concentration vs time curve from zero to two hours after the administration is preferably at least 50 μg·hr/mL, more preferably at least 60 μg·hr/mL, and even more preferably at least 70 μg·hr/mL. The combination of the ranges of the maximum plasma ω3 PUFA concentration and the area under the plasma ω3 PUFA concentration vs time curve is preferably a combination of the range of at least 50 μg/mL and the range of at least 50 μg hr/mL, more preferably a combination of the range of at least 60 μg/mL and the range of at least 60 μg·hr/mL, and even more preferably a combination of the range of at least 70 μg/mL and the range of at least 70 μg·hr/mL.

In a pharmacokinetic study conducted by orally administering the self-emulsifying composition to male crab-eating macaques as fasted for at least 12 hours at an ω3 PUFA dose of 45 mg/kg body weight, the maximum plasma ω3 PUFA concentration is preferably at least 50 μg/mL, and more preferably 70 μg/mL, as calculated with correction by subtraction of the plasma ω3 PUFA concentration before the administration of the composition. The area under the plasma ω3 PUFA concentration vs time curve from zero to 12 hours after the administration is preferably at least 400 μg·hr/mL, and more preferably 500 μg/mL. The combination of the ranges of the maximum plasma ω3 PUFA concentration and the area under the plasma ω3 PUFA concentration vs time curve as above is preferably a combination of the range of at least 50 μg/mL and the range of at least 400 μg·hr/mL, and more preferably a combination of the range of at least 70 μg/mL and the range of at least 500 μg·hr/mL.

In a pharmacokinetic study conducted by orally administering the self-emulsifying composition to humans before meals, immediately after meals or after meals at an ω3 PUFA or EPA dose per individual of 500 mg to 1800 mg, the maximum plasma ω3 PUFA concentration is preferably at least 50 μg/mL, more preferably at least 100 μg/mL, still more preferably at least 150 μg/mL, even more preferably at least 180 μg/mL, and most preferably at least 350 μg/mL, as calculated with correction by subtraction of the plasma ω3 PUFA concentration before the administration of the composition. Alternatively, the maximum plasma ω3 PUFA concentration is preferably 10 to 1000 μg/mL, more preferably 20 to 700 μg/mL, still more preferably 40 to 600 μg/mL, even more preferably 50 to 500 μg/mL, and most preferably 60 to 480 μg/mL. The plasma ω3 PUFA concentration 24 hours after the administration is preferably 5 to 100 μg/mL, more preferably 10 to 90 μg/mL, still more preferably 15 to 85 g/mL, still more preferably 20 to 80 μg/mL, and most preferably 30 to 70 μg/mL. The area under the plasma ω3 PUFA concentration vs time curve from zero to 72 hours after the administration is preferably at least 500 μg·hr/mL, more preferably at least 800 μg·hr/mL, still more preferably at least 1000 μg·hr/mL, even more preferably at least 1500 μg·hr/mL, and most preferably at least 1800 μg·hr/mL. Alternatively, the area under the plasma ω3 PUFA concentration vs time curve as above is preferably 500 to 9000 μg·hr/mL, more preferably 600 to 8000 μg·hr/mL, still more preferably 700 to 7000 μg hr/mL, even more preferably 800 to 5000 μg hr/mL, and most preferably 1500 to 4500 μg·hr/mL. The time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans before meals, immediately after meals or after meals at an ω3 PUFA or EPA dose per individual of 1500 mg to 4200 mg, the maximum plasma ω3 PUFA concentration is preferably at least 50 g/mL, more preferably at least 60 μg/mL, still more preferably at least 70 μg/mL, even more preferably at least 100 μg/mL, and most preferably at least 150 μg/mL, as calculated with correction by subtraction of the plasma ω3

PUFA concentration before the administration of the composition. Alternatively, the maximum plasma ω3 PUFA concentration is preferably 10 to 1000 μg/mL, more preferably 20 to 600 μg/mL, still more preferably 40 to 400 μg/mL, even more preferably 50 to 300 μg/mL, and most preferably 60 to 250 μg/mL. The plasma ω3 PUFA concentration 24 hours after the administration is preferably 5 to 100 g/mL, more preferably 10 to 90 g/mL, still more preferably 12 to 60 g/mL, still more preferably 15 to 50 μg/mL, and most preferably 20 to 45 μg/mL. The area under the plasma ω3 PUFA concentration vs time curve from zero to 72 hours after the administration is preferably at least 500 μg·hr/mL, more preferably at least 800 μg·hr/mL, still more preferably at least 1000 μg·hr/mL, even more preferably at least 1500 μg·hr/mL, and most preferably at least 2000 μg·hr/mL. Alternatively, the area under the plasma ω3 PUFA concentration vs time curve as above is preferably 500 to 6000 μg·hr/mL, more preferably 600 to 5000 μg·hr/mL, still more preferably 700 to 4000 μg·hr/mL, even more preferably 800 to 3500 μg·hr/mL, and most preferably 1000 to 3000 μg·hr/mL. The time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans before meals, immediately after meals or after meals at an ω3 PUFA or EPA dose per individual of 1500 mg to 2400 mg (for example, 2000 mg), the maximum plasma ω3 PUFA concentration is preferably at least 40 μg/mL, more preferably at least 50 μg/mL, still more preferably at least 60 μg/mL, even more preferably at least 65 μg/mL, and most preferably at least 100 μg/mL, as calculated with correction by subtraction of the plasma ω3 PUFA concentration before the administration of the composition. Alternatively, the maximum plasma ω3 PUFA concentration is preferably 10 to 1000 μg/mL, more preferably 20 to 500 μg/mL, still more preferably 40 to 300 μg/mL, even more preferably 50 to 150 μg/mL, and most preferably 60 to 120 μg/mL. The plasma concentration 24 hours after the administration is preferably 5 to 70 μg/mL, more preferably 10 to 60 μg/mL, still more preferably 15 to 50 μg/mL, still more preferably 18 to 40 μg/mL, and most preferably 20 to 35 μg/mL. The area under the plasma ω3 PUFA concentration vs time curve from zero to 72 hours after the administration is preferably at least 500 μg·hr/mL, more preferably at least 800 μg·hr/mL, still more preferably at least 1000 μg·hr/mL, even more preferably at least 1200 μg·hr/mL, and most preferably at least 1500 μg·hr/mL. Alternatively, the area under the plasma ω3 PUFA concentration vs time curve as above is preferably 500 to 5000 μg·hr/mL, more preferably 600 to 4000 μg·hr/mL, still more preferably 700 to 3000 μg·hr/mL, even more preferably 800 to 2500 μg hr/mL, and most preferably 1000 to 2100 μg hr/mL. The time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans before meals, immediately after meals or after meals at an ω3 PUFA or EPA dose per individual of 3300 mg to 4200 mg (for example, 4000 mg), the maximum plasma ω3 PUFA concentration is preferably at least 50 μg/mL, more preferably at least 100 μg/mL, still more preferably at least 150 μg/mL, even more preferably at least 160 μg/mL, and most preferably at least 180 μg/mL, as calculated with correction by subtraction of the plasma ω3 PUFA concentration before the administration of the composition. Alternatively, the maximum plasma ω3 PUFA concentration is preferably 10 to 1000 μg/mL, more preferably 20 to 500 μg/mL, still more preferably 50 to 400 μg/mL, even more preferably 100 to 300 μg/mL, and most preferably 150 to 200 μg/mL. The plasma ω3 PUFA concentration 24 hours after the administration is preferably 10 to 80 μg/mL, more preferably 20 to 60 μg/mL, still more preferably 25 to 55 μg/mL, still more preferably 30 to 50 μg/mL, and most preferably 35 to 45 μg/mL. The area under the plasma ω3 PUFA concentration vs time curve from zero to 72 hours after the administration is preferably at least 500 μg·hr/mL, more preferably at least 1000 μg·hr/mL, still more preferably at least 1500 μg hr/mL, even more preferably at least 2000 μg hr/mL, and most preferably at least 2500 μg·hr/mL. Alternatively, the area under the plasma ω3 PUFA concentration vs time curve as above is preferably 500 to 5000 μg·hr/mL, more preferably 1000 to 4700 μg·hr/mL, still more preferably 1500 to 4500 μg·hr/mL, even more preferably 2000 to 4000 μg·hr/mL, and most preferably 2500 to 3500 μg·hr/mL. The time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma elimination half-life is preferably at least 10 hours, more preferably at least 20 hours, still more preferably at least 30 hours, even more preferably at least 40 hours, and most preferably at least 50 hours. Alternatively, the plasma elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans before meals, immediately after meals or after meals at an ω3 PUFA or EPA dose per individual of 7000 mg to 8500 mg (for example, 8000 mg), the maximum plasma ω3 PUFA concentration is preferably at least 100 µg/mL, more preferably at least 200 µg/mL, still more preferably at least 300 µg/mL, even more preferably at least 350 µg/mL, and most preferably at least 400 µg/mL, as calculated with correction by subtraction of the plasma ω3 PUFA concentration before the administration of the composition. Alternatively, the maximum plasma ω3 PUFA concentration is preferably 100 to 1000 µg/mL, more preferably 200 to 800 µg/mL, still more preferably 300 to 600 µg/mL, even more preferably 300 to 500 µg/mL, and most preferably 350 to 500 µg/mL. The plasma ω3 PUFA concentration 24 hours after the administration is preferably 10 to 100 µg/mL, more preferably 30 to 90 µg/mL, still more preferably 50 to 85 µg/mL, still more preferably 55 to 85 µg/mL, and most preferably 65 to 80 µg/mL. The area under the plasma ω3 PUFA concentration vs time curve from zero to 72 hours after the administration is preferably at least 1000 µg·hr/mL, more preferably at least 2000 µg hr/mL, still more preferably at least 3000 µg·hr/mL, even more preferably at least 4000 µg·hr/mL, and most preferably at least 5000 µg·hr/mL. Alternatively, the area under the plasma ω3 PUFA concentration vs time curve as above is preferably 1000 to 10000 µg hr/mL, more preferably 2000 to 8000 µg·hr/mL, still more preferably 3000 to 7000 µg·hr/mL, even more preferably 3500 to 6500 µg·hr/mL, and most preferably 4000 to 6500 µg·hr/mL. The time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans under fasting, before meals, immediately after meals or after meals at an ω3 PUFA or EPA dose per individual of 1800 mg, the maximum plasma ω3 PUFA concentration is preferably at least 50 µg/mL, more preferably at least 100 µg/mL, still more preferably at least 150 µg/mL, even more preferably at least 200 µg/mL, and most preferably at least 300 µg/mL, as calculated with correction by subtraction of the plasma ω3 PUFA concentration before the administration of the composition. Alternatively, the maximum plasma ω3 PUFA concentration is preferably 10 to 1000 µg/mL, more preferably 20 to 500 µg/mL, still more preferably 40 to 300 µg/mL, even more preferably 50 to 150 µg/mL, and most preferably 50 to 100 µg/mL. Alternatively, the maximum plasma ω3 PUFA concentration is preferably at least 50 µg/mL, more preferably at least 60 µg/mL, still more preferably at least 65 µg/mL, even more preferably at least 80 µg/mL, and most preferably at least 100 µg/mL. Alternatively, the maximum plasma ω3 PUFA concentration is preferably 10 to 1000 µg/mL, more preferably 20 to 500 µg/mL, still more preferably 40 to 300 µg/mL, even more preferably 50 to 150 µg/mL, and most preferably 60 to 120 µg/mL. The plasma ω3 PUFA concentration 24 hours after the administration is preferably 5 to 70 µg/mL, more preferably 10 to 60 µg/mL, still more preferably 13 to 50 µg/mL, still more preferably 15 to 40 µg/mL and most preferably 18 to 30 µg/mL. The area under the plasma ω3 PUFA concentration vs time curve from zero to 72 hours after the administration is preferably at least 500 µg·hr/mL, more preferably at least 1000 µg·hr/mL, still more preferably at least 1500 µg·hr/mL, even more preferably at least 2000 µg·hr/mL, and most preferably at least 3000 µg·hr/mL. Alternatively, the area under the plasma ω3 PUFA concentration vs time curve as above is preferably 500 to 4500 µg·hr/mL, more preferably 600 to 3000 µg·hr/mL, still more preferably 700 to 2500 µg·hr/mL, even more preferably 800 to 2000 µg·hr/mL, and most preferably 1000 to 1500 µg·hr/mL. Alternatively, the area under the plasma ω3 PUFA concentration vs time curve from zero to 72 hours after the administration is preferably at least 500 µg·hr/mL, more preferably at least 800 µg·hr/mL, still more preferably at least 1000 µg·hr/mL, even more preferably at least 1500 µg·hr/mL, and most preferably at least 1800 µg hr/mL. Alternatively, the area under the plasma ω3 PUFA concentration vs time curve as above is preferably 500 to 4500 µg·hr/mL, more preferably 600 to 3000 µg·hr/mL, still more preferably 700 to 2500 µg·hr/mL, even more preferably 800 to 2200 µg·hr/mL, and most preferably 1000 to 2100 µg·hr/mL. The time until the maximum plasma ω3 PUFA concentration is attained is preferably up to 6 hours, more preferably up to 5 hours, still more preferably up to 3 hours, even more preferably up to 1 hour, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 5 hours, and most preferably 2.5 to 4 hours. Alternatively, the time until the maximum plasma ω3 PUFA concentration is attained is preferably up to 6 hours, more preferably up to 5.5 hours, still more preferably up to 5 hours, even more preferably up to 4 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 7 hours, and most preferably 3 to 6 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In a pharmacokinetic study conducted by orally administering the self-emulsifying composition to humans at such a timing as under fasting, before meals, immediately after meals or after meals at an ω3 PUFA or EPA dose of 3600 mg, the maximum plasma ω3 PUFA concentration is preferably at least 50 µg/mL, more preferably at least 100 µg/mL, still more preferably at least 150 µg/mL, even more preferably at least 200 µg/mL, and most preferably at least 300 g/mL, as calculated with correction by subtraction of the plasma ω3 PUFA concentration before the administration of the composition. Alternatively, the maximum plasma ω3 PUFA concentration is preferably at least 50 µg/mL, more preferably at least 100 µg/mL, still more preferably at least 150 µg/mL, even more preferably at least 160 µg/mL, and most preferably at least 180 µg/mL. Alternatively, the maximum plasma ω3 PUFA concentration is preferably 10 to 1000 µg/mL, more preferably 20 to 500 µg/mL, still more preferably 50 to 400 µg/mL, even more preferably 100 to 300

μg/mL, and most preferably 150 to 200 μg/mL. The plasma ω3 PUFA concentration 24 hours after the administration is preferably 10 to 80 μg/mL, more preferably 20 to 60 μg/mL, still more preferably 25 to 50 μg/mL, still more preferably 30 to 45 μg/mL, and most preferably 35 to 40 μg/mL. The area under the plasma ω3 PUFA concentration vs time curve from zero to 72 hours after the administration is preferably at least 500 μg·hr/mL, more preferably at least 1000 μg·hr/mL, still more preferably at least 1500 μg·hr/mL, even more preferably at least 2000 μg·hr/mL, and most preferably at least 2500 or 3000 μg hr/mL. Alternatively, the area under the plasma ω3 PUFA concentration vs time curve as above is preferably 500 to 5000 μg·hr/mL, more preferably 1000 to 4700 g·hr/mL, still more preferably 1500 to 4500 μg·hr/mL, even more preferably 2000 to 4000 μg hr/mL, and most preferably 2500 to 3500 μg hr/mL. The time until the maximum plasma ω3 PUFA concentration is attained is preferably up to 6 hours, more preferably up to 5 hours, still more preferably up to 3 hours, even more preferably up to 1 hour, and most preferably less than one hour. Alternatively, the time until the maximum plasma ω3 PUFA concentration is attained is preferably up to 6 hours, more preferably up to 5.5 hours, still more preferably up to 5 hours, even more preferably up to 4.5 hours, and most preferably less than one hour. Alternatively, the time until the maximum plasma ω3 PUFA concentration is attained is preferably 0.5 to 10 hours, more preferably 1 to 8 hours, still more preferably 1.5 to 7 hours, even more preferably 2 to 6 hours, and most preferably 3.5 to 5.5 hours or 3 to 5 hours. The plasma ω3 PUFA elimination half-life is preferably at least 10 hours, more preferably at least 20 hours, still more preferably at least 30 hours, even more preferably at least 40 hours, and most preferably at least 50 hours. Alternatively, the plasma ω3 PUFA elimination half-life is preferably 0 to 150 hours, more preferably 10 to 120 hours, still more preferably 30 to 100 hours, even more preferably 25 to 75 hours, and most preferably 25 to 50 hours.

In the case of a pharmacokinetic study with humans, the above-mentioned numerical ranges may also be replaced by those mentioned below. To be more specific: In a study conducted by orally administering the self-emulsifying composition at such a timing as under fasting, before meals, immediately after meals or after meals and at an ω3 PUFA or EPA dose per individual of 1800 mg, the maximum plasma ω3 PUFA concentration as calculated with correction by subtraction of the plasma ω3 PUFA concentration before the administration of the composition is not particularly limited, while it may be specified to be: 10 to 150, 20 to 160, 30 to 170, 40 to 180, 50 to 190, 60 to 200, 10 to 50, 50 to 100, 100 to 150, 150 to 200, 200 to 250, 250 to 300, 300 to 350, 350 to 400, 400 to 450, 450 to 500, 500 to 600, 600 to 700, 700 to 800, 800 to 900, 900 to 1000, 10 to 30, 20 to 40, 30 to 50, 40 to 60, 50 to 70, 60 to 80, 70 to 90, 80 to 100, 90 to 110, 100 to 120, 110 to 130, 120 to 140, 130 to 150, 140 to 160, 150 to 170, 160 to 180, 170 to 190, 180 to 200, 190 to 210, 200 to 220, 220 to 240, 240 to 260, 260 to 280, 280 to 300, 10 to 20, 15 to 25, 20 to 30, 25 to 35, 30 to 40, 35 to 45, 40 to 50, 45 to 55, 50 to 55, 53 to 58, 55 to 60, 58 to 63, 60 to 65, 63 to 68, 65 to 70, 68 to 73, 70 to 75, 73 to 78, 75 to 80, 78 to 83, 80 to 85, 83 to 88, 85 to 90, 88 to 93, 90 to 95, 93 to 98, 95 to 100, 98 to 103, 100 to 105, 103 to 108, 105 to 110, 108 to 113, 110 to 115, 113 to 118, 115 to 120, 118 to 123, 120 to 125, 123 to 128, 125 to 130, 128 to 133, 130 to 135, 133 to 138, 135 to 140, 138 to 143, 140 to 145, 143 to 148, 145 to 150, 150 to 160, 155 to 165, 160 to 170, 165 to 175, 170 to 180, 175 to 185, 180 to 190, 185 to 195, 190 to 200, 195 to 205, 200 to 210, 205 to 215, 210 to 220, 215 to 225, 220 to 230, 225 to 235, 230 to 240, 235 to 245, or 240 to 250 μg/ml. In a study conducted by administering the self-emulsifying composition at such a timing as under fasting, before meals, immediately after meals or after meals and at an ω3 PUFA or EPA dose per individual of 3600 mg, the maximum plasma ω3 PUFA concentration may be specified to be: 10 to 200, 30 to 220, 50 to 240, 70 to 260, 90 to 280, 110 to 300, 130 to 320, 150 to 350, 10 to 50, 50 to 100, 100 to 150, 150 to 200, 200 to 250, 250 to 300, 300 to 350, 350 to 400, 400 to 450, 450 to 500, 500 to 600, 600 to 700, 700 to 800, 800 to 900, 900 to 1000, 10 to 30, 20 to 40, 30 to 50.40 to 60, 50 to 70, 60 to 80, 70 to 90, 80 to 100, 90 to 110, 100 to 120, 110 to 130, 120 to 140, 130 to 150, 140 to 160, 150 to 170, 160 to 180, 170 to 190, 180 to 200, 190 to 210, 200 to 220, 220 to 240, 240 to 260, 260 to 280, 280 to 300, 10 to 20, 15 to 25, 20 to 30, 25 to 35, 30 to 40, 35 to 45, 40 to 50, 45 to 55, 50 to 55, 53 to 58, 55 to 60, 58 to 63, 60 to 65, 63 to 68, 65 to 70, 68 to 73, 70 to 75, 73 to 78, 75 to 80, 78 to 83, 80 to 85, 83 to 88, 85 to 90, 88 to 93, 90 to 95, 93 to 98, 95 to 100, 98 to 103, 100 to 105, 103 to 108, 105 to 110, 108 to 113, 110 to 115, 113 to 118, 115 to 120, 118 to 123, 120 to 125, 123 to 128, 125 to 130, 128 to 133, 130 to 135, 133 to 138, 135 to 140, 138 to 143, 140 to 145, 143 to 148, 145 to 150, 150 to 160, 155 to 165, 160 to 170, 165 to 175, 170 to 180, 175 to 185, 180 to 190, 185 to 195, 190 to 200, 195 to 205, 200 to 210, 205 to 215, 210 to 220, 215 to 225, 220 to 230, 225 to 235, 230 to 240, 235 to 245, or 240 to 250 μg/ml.

The area under the plasma ω3 PUFA concentration vs time curve from zero to 72 hours after the administration in a study conducted by administering the self-emulsifying composition at such a timing as under fasting, before meals, immediately after meals or after meals and at an ω3 PUFA or EPA dose per individual of 1800 mg may be specified to be: 500 to 2000, 700 to 2200, 900 to 2400, 1100 to 2600, 500 to 1500, 1000 to 2000, 1500 to 2500, 2000 to 3000, 2500 to 3500, 3000 to 4000, 500 to 1000, 750 to 1250, 1000 to 1500, 1250 to 1750, 1500 to 2000, 1750 to 2250, 2000 to 2500, 2250 to 2750, 2500 to 3000, 2750 to 3250, 3000 to 3500, 3250 to 3750, 3500 to 4000, 3750 to 4250, 4000 to 4500, 4250 to 4750, 4500 to 5000, 500 to 700, 600 to 800, 700 to 900, 800 to 1000, 900 to 1100, 1000 to 1200, 1100 to 1300, 1200 to 1400, 1300 to 1500, 1400 to 1600, 1500 to 1700, 1600 to 1800, 1700 to 1900, 1800 to 2000, 1900 to 2100, 2000 to 2200, 2100 to 2300, 2200 to 2400, 2300 to 2500, 2400 to 2600, 2500 to 2700, 2600 to 2800, 2700 to 2900, 2800 to 3000, 2900 to 3100, 3000 to 3200, 3100 to 3300, 3200 to 3400, 3300 to 3500, 3400 to 3600, 3500 to 3700, 3600 to 3800, 3700 to 3900, 3800 to 4000, 3900 to 4100, 4000 to 4200, 4100 to 4300, 4200 to 4400, 4300 to 4500, 500 to 600, 550 to 650, 600 to 700, 650 to 750, 700 to 800, 750 to 850, 800 to 900, 850 to 950, 900 to 1000, 950 to 1050, 1000 to 1100, 1050 to 1150, 1100 to 1200, 1150 to 1250, 1200 to 1300, 1250 to 1350, 1300 to 1400, 1350 to 1450, 1400 to 1500, 1450 to 1550, 150 to 1600, 1550 to 1650, 160 to 1700, 1650 to 1750, 1700 to 1800, 1750 to 1850, 1800 to 1900, 1850 to 1950, 1900 to 2000, 1950 to 2050, 2000 to 2100, 2050 to 2150, 2100 to 2200, 2150 to 2250, 2200 to 2300, 2250 to 2350, 2300 to 2400, 2350 to 2450, 2400 to 2500, 2450 to 2550, 2500 to 2600, 2550 to 2650, 2600 to 2700, 2650 to 2750, 2700 to 2800, 2750 to 2850, 2800 to 2900, 2850 to 2950, 2900 to 3000, 2950 to 3050, 3000 to 3100, 3150 to 3250, 3200 to 3300, 3250 to 3350, 3300 to 3400, 3350 to 3450, 3400 to 3500, 3500 to 3600, 3600 to 3700, 3700 to 3800, 3800 to 3900, 3900 to 4000, 4000 to 4100, 4100 to 4200, 4200 to 4300, 4300 to 4400, or 4400 to 4500 μg·hr/mL. In a study conducted by administering the self-emulsifying composition at such a timing as under fasting, before meals, immediately after meals or after meals and at an ω3 PUFA or EPA dose per individual of 3600 mg, the area under the plasma ω3 PUFA concentration vs time curve as above may be specified to be: 1500 to 3000, 1800 to 3300, 2100 to 3600, 2400 to 3900, 500 to 1500, 1000 to 2000, 1500 to 2500, 2000 to 3000, 2500 to 3500, 3000 to 4000, 500 to 1000, 750 to 1250, 1000 to 1500, 1250 to 1750, 1500 to 2000, 1750 to 2250, 2000 to 2500, 2250 to 2750, 2500 to 3000, 2750 to 3250, 3000 to 3500, 3250 to 3750, 3500 to 4000, 3750 to 4250, 4000 to 4500, 4250 to 4750, 4500 to 5000, 500 to 70, 600 to 800, 700 to 900, 800 to 1000, 900 to 1100, 1000 to 1200, 1100 to 1300, 1200 to 1400, 1300 to 1500, 1400 to 1600, 1500 to 1700, 1600 to 1800, 1700 to 1900, 1800 to 2000, 1900 to 2100, 2000 to 2200, 2100 to 2300, 2200 to 2400, 2300 to 2500, 2400 to 2600, 2500 to 2700, 2600 to 2800, 2700 to 2900, 2800 to 3000, 2900 to 3100, 3000 to 3200, 3100 to 3300, 3200 to 3400, 3300 to 3500, 3400 to 3600, 3500 to 3700, 3600 to 3800, 3700 to 3900, 3800 to 4000, 3900 to 4100, 4000 to 4200, 4100 to 4300, 4200 to 4400, 4300 to 4500, 500 to 600, 550 to 650, 60 to 700, 650 to 750, 700 to 800, 750 to 850, 800 to 900, 850 to 950, 900 to 1000, 950 to 1050, 1000 to 1100, 1050 to 1150, 1100 to 1200, 1150 to 1250, 1200 to 1300, 1250 to 1350, 1300 to 1400, 1350 to 1450, 1400 to 1500, 1450 to 1550, 1500 to 1600, 1550 to 1650, 1600 to 1700, 1650 to 1750, 1700 to 1800, 1750 to 1850, 1800 to 1900, 1850 to 1950, 1900 to 2000, 1950 to 2050, 2000 to 2100, 2050 to 2150, 2100 to 2200, 2150 to 2250, 2200 to 2300, 2250 to 2350, 2300 to 2400, 2350 to 2450, 2400 to 2500, 2450 to 2550, 250 to 2600, 2550 to 2650, 2600 to 2700, 2650 to 2750, 2700 to 2800, 2750 to 2850, 2800 to 2900, 2850 to 2950, 2900 to 3000, 2950 to 3050, 3000 to 3100, 3150 to 3250, 3200 to 3300, 3250 to 3350, 3300 to 3400, 3350 to 3450, 3400 to 3500, 3500 to 3600, 3600 to 3700, 3700 to 3800, 3800 to 3900, 3900 to 4000, 4000 to 4100, 4100 to 4200, 420 to 4300, 4300 to 4400, or 4400 to 4500 μg hr/mL.

The time until the maximum plasma ω3 PUFA concentration is attained in a study conducted by administering the self-emulsifying composition at such a timing as under fasting, before meals, immediately after meals or after meals and at an ω3 PUFA or EPA dose per individual of 1800 mg to 3600 mg or of 1800 mg to 4000 mg may be specified to be: 0 to 5.5, 1 to 6, 1.5 to 6.5, 2 to 7, 0 to 2, 1 to 3, 2 to 4, 3 to 5, 4 to 6, 5 to 7, 6 to 8, 7 to 9, 8 to 10, 0 to 1, 0.5 to 1.5, 1 to 2, 1.5 to 2.5, 2 to 3, 2.5 to 3.5, 3 to 4, 3.5 to 4.5, 4 to 5, 4.5 to 5.5, 5 to 6, 5.5 to 6.5, 6 to 7, 6.5 to 7.5, 7 to 8, 7.5 to 8.5, 8 to 9, 8.5 to 9.5, 9 to 10, 0 to 0.5, 0.3 to 0.8, 0.5 to 1, 0.8 to 1.3, 1 to 1.5, 1.3 to 1.8, 1.5 to 2, 1.8 to 2.3, 2 to 2.5, 2.3 to 2.8, 2.5 to 3, 2.8 to 3.3, 3 to 3.5, 3.3 to 3.8, 3.5 to 4, 3.8 to 4.3, 4 to 4.5, 4.3 to 4.8, 4.5 to 5, 4.8 to 5.3, 5 to 5.5, 5.3 to 5.8, 5.5 to 6, 5.8 to 6.3, 6 to 6.5, 6.3 to 6.8, 6.5 to 7, 6.8 to 7.3, 7 to 7.5, 7.3 to 7.8, 7.5 to 8, 7.8 to 8.3, 8 to 8.5, 8.3 to 8.8, 8.5 to 9, 8.8 to 9.3, 9 to 9.5, 9.3 to 9.8, or 9.5 to 10 hours.

The plasma ω3 PUFA elimination half-life in a study conducted by administering the self-emulsifying composition at such a timing as under fasting, before meals, immediately after meals or after meals and at an ω3 PUFA or EPA dose per individual of 1800 mg to 3600 mg or of 1800 mg to 4000 mg may be specified to be: 0 to 70, 10 to 80, 20 to 90, 30 to 100, 40 to 110, 0 to 50, 25 to 75, 50 to 100, 75 to 125, 100 to 150, 125 to 175, 150 to 200, 0 to 20, 10 to 30, 20 to 40, 30 to 50, 40 to 60, 50 to 70, 60 to 80, 70 to 90, 80 to 100, 90 to 110, 100 to 120, 110 to 130, 120 to 140, 130 to 150, 0 to 10, 5 to 15, 10 to 20, 15 to 25, 20 to 30, 25 to 35, 30 to 40, 35 to 45, 40 to 50, 45 to 55, 50 to 60, 55 to 65, 60 to 70, 65 to 75, 70 to 80, 75 to 85, 80 to 90, 85 to 95, 90 to 100, 95 to 105, 100 to 110, 105 to 115, or 110 to 120 hours.

In a pharmacokinetic study conducted by orally administering the self-emulsifying composition to humans at such a timing as under fasting, before meals, immediately after meals or after meals and at an ω3 PUFA or EPA dose of 1800 mg or 2000 mg, the maximum plasma ω3 PUFA concentration in steady state (Css max) is preferably at least 50 μg/mL, more preferably at least 100 μg/mL, still more preferably at least 150 g/mL, still more preferably at least 200 μg/mL, and most preferably at least 300 μg/mL, as calculated with correction by subtraction of the plasma ω3 PUFA concentration before the administration of the composition. Alternatively, the Css max is preferably 10 to 1000 μg/mL, more preferably 20 to 500 μg/mL, still more preferably 50 to 400 μg/mL, still more preferably 100 to 300 μg/mL, and most preferably 150 to 200 μg/mL. The minimum plasma ω3 PUFA concentration at steady state (Css min) is preferably at least 10 μg/mL, more preferably at least 20 μg/mL, still more preferably at least 30 μg/mL, still more preferably at least 40 μg/mL, and most preferably at least 50 μg/mL. Alternatively, the Css min is preferably 10 to 500 μg/mL, more preferably 20 to 250 μg/mL, still more preferably 40 to 200 μg/mL, still more preferably 60 to 150 μg/mL, and most preferably 75 to 95 μg/mL. The average plasma ω3 PUFA concentration at steady state (Css ave) is preferably at least 30 μg/mL, more preferably at least 60 g/mL, still more preferably at least 90 μg/mL, still more preferably at least 120 μg/mL, and most preferably at least 150 μg/mL. Alternatively, the Css ave is preferably 10 to 700 μg/mL, more preferably 20 to 500 μg/mL, still more preferably 50 to 300 μg/mL, still more preferably 100 to 200 μg/mL, and most preferably 130 to 150 μg/mL.

In a pharmacokinetic study conducted by orally administering the self-emulsifying composition to humans at such a timing as under fasting, before meals, immediately after meals or after meals and at an ω3 PUFA or EPA dose of 3600 mg or 4000 mg, the maximum plasma ω3 PUFA concentration in steady state (Css max) is preferably at least 100 μg/mL, more preferably at least 200 μg/mL, still more preferably at least 250 μg/mL, still more preferably at least 300 μg/mL, and most preferably at least 350 μg/mL, as calculated with correction by subtraction of the plasma ω3 PUFA concentration before the administration of the composition. Alternatively, the Css max is preferably 10 to 1000 μg/mL, more preferably 100 to 800 μg/mL, still more preferably 200 to 600 μg/mL, still more preferably 250 to 500 μg/mL, and most preferably 350 to 400 μg/mL. The minimum plasma ω3 PUFA concentration at steady state (Css min) is preferably at least 50 μg/mL, more preferably at least 100 μg/mL, still more preferably at least 150 μg/mL, still more preferably at least 170 μg/mL, and most preferably at least 200 μg/mL. Alternatively, the Css min is preferably 10 to 500 μg/mL, more preferably 20 to 250 μg/mL, still more preferably 40 to 200 μg/mL, still more preferably 60 to 150 μg/mL, and most preferably 75 to 95 μg/mL. The average plasma ω3 PUFA concentration at steady state (Css ave) is preferably at least 30 μg/mL, more preferably at least 60 μg/mL, still more preferably at least 90 μg/mL, still more preferably at least 120 μg/mL, and most preferably at least 5150 g/mL. Alternatively, the Css ave is preferably 10 to 700 μg/mL, more preferably 20 to 500 μg/mL, still more preferably 50 to 300 μg/mL, still more preferably 100 to 200 μg/mL, and most preferably 130 to 150 μg/mL.

In a pharmacokinetic study conducted by orally administering the self-emulsifying composition to humans at such a timing as under fasting, before meals, immediately after meals or after meals and at an ω3 PUFA or EPA dose per individual of 500 mg, 1000 mg, 1800 mg, 2000 mg, 3600 mg, 4000 mg, 6000 mg or 8000 mg, the maximum plasma ω3 PUFA concentration in steady state (Css max), the minimum plasma ω3 PUFA concentration in steady state (Css min) and the average plasma ω3 PUFA concentration in steady state (Css ave) as calculated with correction by subtraction of the plasma ω3 PUFA concentration before the administration of the composition are not particularly limited, while each of them may be specified to be: 10 to 110, 20 to 120, 30 to 130, 40 to 140, 50 to 150, 60 to 160, 70 to 170, 80 to 180, 90 to 190, 100 to 200, 110 to 210, 120 to 220, 130 to 230, 140 to 240, 150 to 250, 160 to 260, 170 to 270, 180 to 280, 190 to 290, 200 to 300, 210 to 310, 220 to 320, 230 to 330, 240 to 340, 250 to 350, 260 to 360, 270 to 370, 280 to 380, 290 to 390, 300 to 400, 310 to 410, 320 to 420, 330 to 430, 340 to 440, 350 to 450, 360 to 460, 370 to 470, 380 to 480, 390 to 490, 400 to 500, 410 to 510, 420 to 520, 430 to 530, 440 to 540, 450 to 550, 460 to 560, 470 to 570, 480 to 580, 490 to 590, 500 to 600, 510 to 610, 520 to 620, 530 to 630, 540 to 640, 550 to 650, 560 to 660, 570 to 670, 580 to 680, 590 to 690, 600 to 700, 610 to 710, 620 to 720, 630 to 730, 640 to 740, 650 to 750, 660 to 760, 670 to 770, 680 to 780, 690 to 790, 700 to 800, 810 to 910, 820 to 920, 830 to 930, 840 to 940, 850 to 950, 860 to 960, 870 to 970, 880 to 980, 890 to 990, 900 to 100), 10 to 30, 20 to 40, 30 to 50, 40 to 60, 50 to 70, 60 to 80, 70 to 90, 80 to 100, 90 to 110, 100 to 120, 110 to 130, 120 to 140, 130 to 150, 140 to 160, 150 to 170, 160 to 180, 170 to 190, 180 to 200, 190 to 210, 200 to 220, 210 to 230, 220 to 240, 230 to 250, 240 to 260, 250 to 270, 260 to 280, 270 to 290, 280 to 300, 290 to 310, 300 to 320, 310 to 330, 320 to 340, 330 to 350, 340 to 360, 350 to 370, 360 to 380, 370 to 390, 380 to 400, 390 to 410, 400 to 420, 410 to 430, 420 to 440, 430 to 450, 440 to 460, 450 to 470, 460 to 480, 470 to 490, 480 to 500, 490 to 510, 500 to 520, 510 to 530, 520 to 540, 530 to 550, 540 to 560, 550 to 570, 560 to 580, 570 to 590, 580 to 600, 590 to 610, 600 to 620, 610 to 630, 620 to 640, 630 to 650, 640 to 660, 650 to 670, 660 to 680, 670 to 690, 680 to 700, 690 to 710, 700 to 720, 710 to 730, 720 to 740, 730 to 750, 740 to 760, 750 to 770, 760 to 780, 770 to 790, 780 to 800, 790 to 810, 800 to 820, 810 to 830, 820 to 840, 830 to 850, 840 to 860, 850 to 870, 860 to 880, 870 to 890, 880 to 900, 890 to 910, 900 to 920, 910 to 930, 920 to 940, 930 to 950, 940 to 960, 950 to 970, 960 to 980, 970 to 990, 980 to 1000, 990 to 1010, 1000 to 1020, 1010 to 1030, 1020 to 1040, 1030 to 1050, 1040 to 1060, 1050 to 1070, 1060 to 1080, 1070 to 1090, 1080 to 1100, 1090 to 1110, 1100 to 1120, 1110 to 1130, 1120 to 1140, 1130 to 1150, 1140 to 1160, 1150 to 1170, 1160 to 1180, 1170 to 1190, or 1180 to 1200.

The present invention may be defined by a combination of two or more selected from among the maximum plasma ω3 PUFA concentration, the plasma ω3 PUFA concentration 24 hours after the administration, the area under the plasma ω3 PUFA concentration vs time curve from zero to 72 hours after the administration, the time until the maximum plasma ω3 PUFA concentration is attained, and the plasma ω3 PUFA elimination half-life.

By administration, the self-emulsifying composition of the present invention is preferably capable of improving (reducing) at least one parameter selected from TG, T-cho, LDL-C, non-HDL-C, VLDL-C, VLDL-TG, oxidized LDL, small dense LDL, remnant-like lipoprotein cholesterol, ApoB, ApoCIII, lipoprotein (a), Lp-PLA2, CETP activity, hs-CRP, plasma phospholipid, free fatty acid, fasting blood glucose, HbA1c, HOMA-IR, intercellular adhesion molecule-, IL-6, PAI-1, creatinine, AST, ALT, uric acid, 8-isoprostane, TXA2 and LTB2 and the metabolites thereof (hydroxy eicosatetraenoic acid, HETE), and the like. The self-emulsifying composition of the present invention is also preferably capable of improving (increasing) at least one parameter selected from HDL-C, apoA-I, apoA-I/ApoB ratio, EPA in the plasma or serum, EPA in the erythrocyte membrane or platelet membrane, and the like. The self-emulsifying composition of the present invention is also preferably capable of reducing the number of LDL particles, increasing LDL particle size, and improving at least one parameter selected from ApoE genotype abnormality, hemoglobin abnormality, hematocrit abnormality, thrombocyte abnormality, and the like.

Particularly preferred is improvement (reduction) of at least one parameter selected from small dense LDL, 8-isoprostane, and TXA2 and LTB2 and metabolites thereof (HETE).

Preferably, the amount of ω3 PUFA absorbed upon the administration of the self-emulsifying composition of the present invention is not saturated by the high dose administration, and the maximum plasma ω3 PUFA concentration, the plasma ω3PUFA concentration 24 hours after the administration, or the area under the plasma ω3 PUFA concentration vs time curve preferably increases in dose dependent manner. When the composition is administered before, immediately after or after meals at a doubled EPA dose per individual within the range of 500 to 10000 mg (for example, 3600 mg for a dose of 1800 mg, 4000 mg for a dose of 2000 mg, 8000 mg for a dose of 4000 mg, or the like), the value of the maximum plasma ω3 PUFA concentration, the plasma ω3 PUFA concentration 24 hours after the administration, or the area under the plasma ω3 PUFA concentration vs time curve becomes 1.2 times, preferably 1.5 times, more preferably 1.8 times, and most preferably 2.0 times higher.

When the ω3 PUFA is administered at a high dose, (for example, at a daily individual dose of 4000 mg) in order to realize the high therapeutic effects, the excessive amount that could not be absorbed by human remains in the intestinal tract and this invites side effects of lower gastrointestinal tract or the like. In contrast, in the case of the self-emulsifying composition of the present invention, excellent absorption is realized even in the case of the high dose administration as described above, and the ω3 PUFA remaining in the intestinal tract will be reduced or eliminated. The side effects are thereby reduced.

Examples of the side effects which can be reduced or eliminated include side effects of lower gastrointestinal tract, nausea, abdominal discomfort, diarrhea, abdominal pain, heartburn, vomiting, anorexia, constipation, stomatitis, thirst, bloating, flatulence, etc.

When the self-emulsifying composition of the present invention is administered at the timing other than during, after or immediately after meals, that is to say, at such a timing as under fasting (at least 8 hours, and preferably at least 10 hours after the last meal), before meals, immediately before meals, between meals or at bedtime, or to a patient suffering from reduced absorption ability of the intestinal tract (elderly, patient with an intestinal disease, patient after the intestinal surgery, terminal cancer patient, patient taking a lipase inhibitor), the results of the administration are preferably the same as other occasions.

For example, when the self-emulsifying composition is administered at a timing other than immediately after meals (for example, before meals) and at an EPA dose per individual of 1500 to 4200 mg (for example, 1800 mg, 2000 mg, 3000 mg, 3600 mg or 4000 mg), the maximum plasma ω3 PUFA concentration, the plasma ω3 PUFA concentration 24 hours after the administration or the area under the plasma ω3 PUFA concentration vs time curve as calculated with correction by subtraction of the plasma ω3 PUFA concentration before the administration of the composition is preferably 50 to 150%, more preferably 60 to 140%, still more preferably 70 to 130%, even more preferably 80 to 120%, and most preferably 90 to 110% of the maximum plasma ω3 PUFA concentration, the plasma ω3 PUFA concentration 24 hours after the administration or the area under the plasma ω3 PUFA concentration vs time curve in the case of the administration immediately after meals.

The self-emulsifying composition of the present invention may also contain additives such as an emulsification aid, stabilizer, antiseptic, surfactant, and antioxidant. Exemplary emulsification aids include fatty acids containing 12 to 22 carbon atoms such as stearic acid, oleic acid, linoleic acid, palmitic acid, linolenic acid, and myristic acid and their salts. Exemplary stabilizers include phosphatidic acid, ascorbic acid, glycerin, and cetanols, and exemplary antiseptics include ethyl paraoxybenzoate and propyl paraoxybenzoate. Exemplary surfactants include sucrose fatty acid esters, sorbitan fatty acid esters, glycerin fatty acid esters, polyoxyethylene sorbitan fatty acid esters, polyoxyethylene alkyl ethers, polyoxyethylene fatty acid esters, polyoxyethylene alkyl phenyl ethers, and polyoxyethylene polyoxypropylene alkyl ethers. Exemplary antioxidants include oil-soluble antioxidants such as butylated hydroxy toluene, butylated hydroxy anisole, propyl gallate, propyl gallate, pharmaceutically acceptable quinone, astaxanthin, and α-tocopherol.

In addition, an adequate carrier or vehicle, a colorant, a flavor, and optionally, a vegetable oil and an additive such as non-toxic organic solvent or non-toxic solubilizing agent, emulsifier, suspending agent (for example, Tween 80 and gum arabic solution), isotonic agent, pH adjusting agent, stabilizer, corrective, flavoring agent, preservative, antioxidant, or absorption promoter commonly used in the art may be adequately combined with the inventive composition to prepare an appropriate pharmaceutical preparation.

More specifically, since the ω3 PUFA is highly unsaturated, effective amount of an oil-soluble antioxidant, for example, at least one member selected from butylated hydroxytoluene, butylated hydroxyanisole, propyl gallate, propyl gallate, pharmaceutically acceptable quinone, astaxanthin, and α-tocopherol is preferably incorporated in the composition.

Since the self-emulsifying composition of the present invention is also used for pharmaceutical application, it preferably has good appearance, self-emulsifying property, composition dispersibility, emulsion stability, and storage stability. The appearance of the self-emulsifying composition is such that the composition is not separated, clouded, solidified, or precipitated, but transparent. The composition having poor appearance may be pharmaceutically unsuitable, and such composition may be insufficient in required performance such as self-emulsifying property.

With regard to the storage temperature, the self-emulsifying composition and the preparation prepared by encapsulating such composition is preferably transparent at both low temperature and high temperature in view of its use in cold district or hot environment.

In the case of the self-emulsifying composition having good self-emulsifying property, good dispersibility of the composition, and high emulsion stability, the composition rapidly disperses upon contact with water to form a microemulsion having adequate emulsion droplet diameter. Absorbability of an oil such as EPA-E is related to the size of the emulsion droplet diameter, and degree of the absorbability upon administration to the animal can be estimated by measuring the emulsion droplet diameter.

In the present invention, the "mean droplet diameter" is the value of volume mean diameter among droplets of the emulsified composition measured by using a particle size analyzer (for example, Nanotorac manufactured by Nikkiso Co., Ltd.) with water being used for the dispersion medium according to standard measurement method (for example, set zero time of 30 seconds, measurement time of 30 seconds, average of three measurements). The mean droplet diameter when the self-emulsifying composition of the present invention is dispersed in water or the like is not particularly limited as long as it is up to 2 μm, and the product has good emulsion dispersibility, good emulsion stability, or good absorbability, and the mean droplet diameter is typically up to 1.5 μm, more preferably up to 1.0 μm, still more preferably up to 0.5 μm, and most preferably up to 0.3 μm.

The self-emulsifying composition of the present invention may be used by combining with a second effective component. The second effective component may be any component adequately selected depending on the intended type and severity of the disease as long as it does not adversely affect the merits of the ω3 PUFAs. Exemplary such second effective components include therapeutic agents for hyperlipidemia, antihypertensives, antidiabetics, antioxidants, blood flow improving agents, bile acid derivatives, therapeutic agents for NAFLD and NASH, as well as progression suppressants and therapeutic agents for cognitive impairment.

Examples of a favorable second effective component include such therapeutic agents for hyperlipidemia as polyene phosphatidyl choline, unsaponifiable matter in soybean oil (soysterol), gamma orizanol, riboflavin butyrate, dextran sulfate sodium sulfur 18, pantethine, and elastase. Also included are statins such as pravastatin, simbastatin, atorvastatin, fluvastatin, pitavastatin, rosuvastatin and cerivastatin; fibrates such as simfibrate, clofibrate, clinofibrate, bezafibrate and fenofibrate; lipolytic enzyme inhibitors such as orlistat and cetilistat; resins such as cholestyramine and cholestyramide; and ezetimibe.

Exemplary antihypertensives include: angiotensin II receptor antagonists such as irbesartan, olmesartan medoxomil, candesartan cilexetil, telmisartan, valsartan, and losartan potassium; angiotensin converting enzyme inhibitors such as alacepril, imidapril hydrochloride, enalapril maleate, captopril, quinapril hydrochloride, cilazapril hydrate, temocapril hydrochloride, delapril hydrochloride, trandolapril, benazepril hydrochloride, perindopril, and lisinopril hydrate; calcium antagonists such as azelnidipine, amlodipine besylate, aranidipine, efonidipine hydrochloride, cilnidipine, nicardipine hydrochloride, nifedipine, nimodipine, nitrendipine, nilvadipine, barnidipine hydrochloride, felodipine, benidipine, and manidipin; α-receptor blockers such as tolazoline and phentolamine; β-receptor blockers such as atenolol, metoprolol, acebutolol, propranolol, pindolol, carvedilol, and labetalol hydrochloride; α-receptor stimulants such as clonidine and methyldopa; and diuretics such as eplerenone, hydrochlorothiazide and furosemide.

Exemplary antidiabetics include: α-glucosidase inhibitors such as acarbose, voglibose and miglitol; sulfonylurea hypoglycemic agents such as gliclazide, glibenclamide, glimepiride and tolbutamide; short-acting insulin secretagogues such as nateglinide and mitiglinide; biguanide hypoglycemic agents such as metformin hydrochloride and buformin hydrochloride; dipeptidyl phosphatase-4 inhibitors such as sitagliptin, vildagliptin, alogliptin, linagliptin, teneligliptin, anagliptin and saxagliptin; thiazolidines such as pioglitazone hydrochloride and rosiglitazone maleate; glucagon-like peptide 1 derivatives such as exenatide and liraglutide; and sodium-glucose cotransporter 2 inhibitors such as ipragliflozin, dapagliflozin, luseogliflozin, tofogliflozin, canagliflozin and empagliflozin.

Exemplary antioxidants include such vitamins as ascorbic acid (vitamin C), tocopherol (vitamin E) and tocopherol nicotinate ester, N-acetylcysteine, and probucol.

Exemplary blood flow improving agents include cilostazol, ticlopidine hydrochloride, alprostadil, limaprost, beraprost sodium, sarpogrelate hydrochloride, argatroban, naftidrofuryl, isoxsuprine hydrochloride, batroxobin, dihydroergotoxine mesylate, tolazoline hydrochloride, heproni cate, and shimotsuto extract.

Exemplary bile acid derivatives include ursodeoxycholic acid, chenodeoxycholic acid, bile powder, deoxycholic acid, cholic acid, bile extract, bear bile, oriental bezoar, and dehydrocholic acid. Favorable examples are biotin (vitamin B7), cyanocobalamin (vitamin B12), pantothenic acid (vitamin B5), folic acid (vitamin B9), thiamine (vitamin B1), vitamin A, vitamin D, vitamin K, tyrosine, pyridoxine (vitamin B6), branched amino acids such as leucine, isoleucine and valine, calcium, iron, zinc, copper, magnesium, and the like. Also favorable are such ingredients of foods for specified health use and foods with nutrient function claims as soybean proteins, chitosan, low molecular-weight sodium alginate, dietary fiber derived from psyllium seed husks, soybean peptides bound to phospholipids, plant sterol esters, plant stanol esters, diacylglycerol, globin proteolysis products, and tea catechin.

Exemplary therapeutic agents for NAFLD and NASH include the statins such as pravastatin, simbastatin, atorvastatin, fluvastatin, pitavastatin, rosuvastatin and cerivastatin; the angiotensin II receptor antagonists such as irbesartan, olmesartan medoxomil, candesartan lexetil, telmisartan, valsartan, and losartan potassium; the biguanide hypoglycemic agents such as metformin hydrochloride and buformin hydrochloride; and the thiazolidines such as pioglizone hydrochloride and rosiglitazone maleate as mentioned above, as well as aspirin and farnesoid X receptor (hereafter abbreviated as FXR) ligands such as ursodeoxycholic acid, chenodeoxycholic acid and obeticholic acid.

Exemplary progression suppressants and therapeutic agents for cognitive impairment include acetylcholineesterase inhibitors such as donepezil hydrochloride and galantamine hydrobromide; NMDA receptor inhibitors such as memantine hydrochloride; antiplatelets such as aspirin, clopidogrel sulfate, cilostazol, and ticlopidine hydrochloride; and factor Xa inhibitors such as rivaroxaban and apixaban. In addition, the therapeutic agents for hyperlipidemia, antihypertensives, antidiabetics, antioxidants and blood flow improving agents as mentioned above are also usable as progression suppressants and therapeutic agents for cognitive impairment.

To realize pharmacological actions of the ω3 PUFA, the self-emulsifying composition of the present invention preferably has at least one merit selected from good appearance, good self-emulsifying property, high composition dispersibility, high emulsion stability, high storage stability (including the stability at low and high temperatures), high absorbability, in particular high absorbability and high absorption speed under fasting conditions, absorbability independent of diet, convenience to patients taking the composition, reduction in side effects, and a preparation of easy compliance.

The self-emulsifying composition of the present invention is well adapted for use as a therapeutic agent for treating various diseases of animals, mammals in particular, that is to say, is usable as, for instance, therapeutic agent for dyslipidemia (hypercholesterolemia, LDL hypercholesterolemia, non-HDL hypercholesterolemia, VLDL hypercholesterolemia, HDL hypocholesterolemia, hypertriglyceridemia, apo B hyperlipoproteinemia, apo A-I hypolipoproteinemia, increased LDL particle number-emia, small LDL particle size-emia, hyper-oxidized LDL-emia, hyper-small dense LDL-emia, hyper-RLP-C-emia, hypo-apoA-I/ApoB ratio-emia, hyper-ApoCIII-emia, dys-ApoE genotype-emia, hyper-lipoprotein (a)-emia, hyper-Lp-PLA2-emia, hyper-CETP activity-emia, hyper-hs-CRP-emia, hypo-EPA-emia (the state wherein EPA value in plasma, serum, erythrocyte membrane, platelet membrane is low), hyper-free fatty acidemia), hyper-fasting glucose-emia, hyper-HbA1c-emia, hyper-HOMA-IR-emia, hyper-intercellular adhesion molecule-1-emia, hyper-IL-6-emia, hyper-PAI-1-emia, hyper-creatininemia, hyper-AST-emia, hyper-ALT-emia, hyper-uric acidemia, hyper-8-isoprostane-emia, hyper-TXA2-emia, hyper-LTB2-emia, and so forth), therapeutic agent for postprandial hypertriglyceridemia, anti-arteriosclerotic, platelet aggregation suppressant, therapeutic agent for peripheral circulatory insufficiency, prophylactic agent for cardiovascular events, therapeutic agent for inflammatory disease (NAFLD, NASH, and so forth), progression suppressant and therapeutic agent for cognitive impairment (dementia of the Alzheimer's type, cerebrovascular dementia, mixed type of dementia, and so forth), anticancer agent, and therapeutic agent for central disease (depression, depressive condition, obsessive-compulsive disorder, social anxiety disorder, panic disorder, and so forth). In the treatment of the diseases as above, the inventive self-emulsifying composition is not particularly limited in frequency of administration per day, and is preferably administered one time a day at the entire daily dose or two or three times a day at divided doses, with one or two time administration per day being more preferable and one time administration per day most preferable.

The self-emulsifying composition of the present invention is particularly effective for the amelioration or treatment of dyslipidemia and postprandial hypertriglyceridemia, and the prevention of their recurrence or progression to metabolic syndrome, cardiocerebrovascular events, and ulcer or gangrene at a limb distal end. Exemplary mammals include human, domestic animals such as cattle, horse, and pig, and companion animals such as dog, cat, rabbit, rat, and mouse, and the preferred is human. More specifically, the self-emulsifying composition of the present invention is anticipated to show ameliorating or therapeutic effects for dyslipidemia and postprandial hypertriglyceridemia in patients with dyslipidemia suffering from increase in the blood lipid, exhibiting insulin resistance or suffering from increase in the blood pressure, such as metabolic syndrome patients.

EXAMPLES

Next, the present invention is described in further detail by referring to the following Examples and Comparative Examples which by no means limit the scope of the invention.

Example 1

0.09 g of water, 0.53 g of polyoxyethylene (20) sorbitan oleate, 0.39 g of soybean lecithin, and 4.0 g of EPA-E were weighed, sealed, and mixed while heating to about 70° C. to thereby prepare the self-emulsifying composition. The self-emulsifying composition was sealed after purging with nitrogen, and stored at room temperature until the evaluation was conducted. Formulation of the self-emulsifying composition is shown in Table 1.

Examples 2 to 11 and Comparative Examples 1 and 2

The self-emulsifying compositions of Examples 2 to 8 and the compositions of Comparative Examples 1 and 2 were prepared and stored by repeating the method of Example 1 so that the compositional ratios were as shown in Table 1. Formulations of the self-emulsifying compositions and the compositions are shown in Table 1.

Comparative Examples 3 and 4

The compositions of Comparative Examples 3 and 4 were prepared and stored by repeating the method of Example 1 so that the compositional ratios were as shown in Table 1. Formulations of the compositions are shown in Table 1.

The self-emulsifying compositions and the compositions of Comparative Examples as produced by the method as described above were each encapsulated in the capsule containing gelatin as its main component.

Test Example 1 <Evaluation of Appearance>

The self-emulsifying compositions and the compositions of Comparative Examples as produced by the above production method were allowed to stand, and after about 1 hour, their appearance was evaluated. When the composition was homogeneous due to the good compatibility, the composition was evaluated as "transparent." The composition was evaluated as "separated" when the separation was observed, and as "cloudy" when opacity was observed.

The results are shown in Table 1.

Test Example 2 <Evaluation of Self-Emulsifying Property>

The self-emulsifying compositions and the compositions of Comparative Examples as produced by the above production method were evaluated for self-emulsifying property by adding 10 μL of each composition dropwise to 5 mL of purified water or first fluid for dissolution test of Japanese Pharmacopeia at 37° C. in the test tube. The composition which spontaneously emulsified just by the dropwise addition was evaluated as "good," and the case which did not become an emulsion just by the dropwise addition was evaluated as "poor." The composition was then lightly stirred under consistent condition, and examined for other properties. With regard to the dispersibility of the composition, the composition was evaluated as "good" when dispersed and as "poor" when the composition was partly left undispersed as a mass. With regard to the emulsion stability, the composition was evaluated as "good" when no oil separation was observed, and as "poor" when oil separation was observed. It is to be noted that the compositions which were not evaluated as "transparent" in the appearance evaluation were not evaluated in such properties since inhomogeneous compositions were conceived to be inadequate for property evaluation.

The results are shown in Table 1.

Test Example 3 <Evaluation of Emulsion Droplet Diameter>

Using about 1.5 mL of the emulsified composition as obtained in Test Example 2, the mean droplet diameter (volume mean diameter) was measured by a particle size analyzer (Nanotorac, manufactured by Nikkiso Co., Ltd.) using water as a dispersion medium.

Test Example 4 <Evaluation of the Appearance after Storage Under Severe Conditions>

The compositions which were evaluated as "transparent" or "cloudy" in Test Example 1 were allowed to stand and stored overnight (for about 12 hours) at 5° C. or 40° C. before their appearance was evaluated. When the composition was homogeneous due to its good compatibility, the composition was evaluated as "transparent." The composition was evaluated as "separated" when the separation was observed, and as "cloudy" when opacity was observed.

The results are shown in Table 1.

Test Example 5 <Pharmacokinetics in Beagles>

The produced compositions or capsules (Examples 1, 3 and 5) were each orally administered to 6 male beagles (at the age of 2 to 6 years with the body weight of 8 to 13 kg, 3 Marshall beagles and 3 Nosan beagles) under fasting conditions, and blood EPA concentration was evaluated. The test animals had been fasted since 18 hours or more before the administration, and each animal was administered with the composition in an amount corresponding to 600 mg of the EPA-E. Blood was collected before the administration, and 0.5, 1, 1.5, 2, 3, 4, 6, 8, and 24 hours after the administration, and plasma was separated to measure plasma EPA concentration by LC/MS/MS (method in which a sample is isolated by liquid chromatography, then subjected to mass spectrometry to conduct separation and measurement thereon). The control group was administered with the EPA-E stock solution encapsulated in a capsule.

Table 1 shows the maximum plasma ω3 PUFA concentration (Cmax), the area under the plasma ω3 PUFA concentration vs time curve from zero to two hours ($AUC_{0-2}$) and the area under the plasma ω3 PUFA concentration vs time curve from zero to 24 hours ($AUC_{0-24}$) as calculated from the test results. In the calculation of each parameter, correction was made by subtracting the blood EPA concentration before the administration from the measured blood concentration.

Test Example 6 <Pharmacokinetics in Crab-Eating Macaques>

The produced compositions or capsules are orally administered to 6 crab-eating macaques (at the age of 2 to 5 years with the body weight of 2.70 to 4.65 kg; Hamuri) under fasting conditions, and blood EPA concentration is evaluated. The test animals are fasted for 12 hours or more before the administration, and each animal is administered with the self-emulsifying composition in an amount corresponding to 45 mg/kg body weight of the EPA-E. The control group is administered with the EPA-E stock solution encapsulated in a capsule. Blood is collected before the administration, and 1, 2, 4, 6, 8, 10, 12, 24, 48 and 72 hours after the administration, and plasma is separated to measure EPA in plasma by LC/MS/MS. From the test results, the maximum plasma ω3 PUFA concentration (Cmax), the area under the plasma ω3 PUFA concentration vs time curve from zero to 12 hours ($AUC_{0-12}$), and the area under the plasma ω3 PUFA concentration vs time curve from zero to 72 hours ($AUC_{0-72}$) are calculated. In the calculation of each parameter, correction is made by subtracting the blood EPA concentration before the administration from the measured blood concentration.

In the animals having the compositions administered thereto, values of blood concentration parameters, such as the Cmax and the $AUC_{0-12}$, are increased as compared with the control group. More specifically, it is confirmed that, when the self-emulsifying composition of the present invention is administered, amount of the EPA absorbed is increased, and also, EPA absorption is rapid after the oral administration.

Test Example 6-2 <Pharmacokinetics in Humans (Single Dose Administration Test, Administration of 1800 mg)>

The capsule having the self-emulsifying composition of the present invention containing 80% by weight of EPA-E as its content was orally administered to human (12 cases, healthy adult males of 20 to 40 years old with a body weight of 55.0 to 77.0 kg and a BMI of 18.5 or more but less than 25.0) under fasting conditions to evaluate the change of blood EPA concentration. The self-emulsifying composition in an amount corresponding to 1800 mg of EPA-E was orally administered in single dose to each human who had been fasted since 10 hours or more before the administration by using 200 mL of water in the morning under fasting. The blood was collected 0.5, 1, 1.5, 2, 3, 4, 5, 6, 7, 8, 9, 10, 12, 15, 18, 24, 48 and 72 hours after the administration. Immediately after the collection, the blood was cooled on ice, and centrifuged at 2000×g at 4° C. for 10 minutes to separately collect the plasma. After having stored the resulting plasma at a temperature not higher than −20° C. in frozen state, concentration of the EPA in the plasma was measured by LC/MS/MS (method in which a sample is isolated by liquid chromatography, then subjected to mass spectrometry to conduct separation and measurement thereon).

The capsule having the self-emulsifying composition of the present invention containing 80% by weight of EPA-E as its content was also orally administered to human immediately after meals, and the measurement was conducted by repeating the procedure as described above.

For the control group, the EPA-E stock solution (high purity EPA-E (at least 96.5% by weight) containing no emulsifier or the like and used with the same EPA-E amount as that of the self-emulsifying composition of the present invention; the same applying hereafter) filled in the capsule was orally administered to human (12 cases, healthy adult males of 20 to 40 years old with a body weight of 55.0 to 77.0 kg and a BMI of 18.5 or more but less than 25.0) under fasting conditions (fasting since at least 10 hours before the administration), and the measurement was conducted by repeating the procedure as described above.

Table 2 shows the maximum plasma concentration (Cmax), the plasma ω3 PUFA concentration 24 hours after the administration (C), the area under the plasma ω3 PUFA concentration vs time curve from zero to 72 hours ($AUC_{0-72}$), the time until the maximum plasma ω3 PUFA concentration is attained (Tmax), and the plasma ω3 PUFA elimination half-life ($t_{1/2}$) as calculated from the test results. In the calculation of each parameter, correction was made by subtracting the blood EPA concentration before the administration from the measured blood concentration.

Test Example 6-3 <Pharmacokinetics in Humans (Single Dose Administration Test, Administration of 3600 mg)>

The test procedure of the Test Example 6-2 was repeated except that the dose per individual was 3600 mg. This test was conducted on 6 humans. Table 3 shows the maximum plasma ω3 PUFA concentration (Cmax) the plasma ω3 PUFA concentration 24 hours after the administration ($C_{24}$), the area under the plasma ω3 PUFA concentration vs time curve from zero to 72 hours ($AUC_{0-72}$), the time until the maximum plasma ω3 PUFA concentration is attained (Tmax), and the plasma ω3 PUFA elimination half-life ($t_{1/2}$) as calculated from the test results. In the calculation of each parameter, correction was made by subtracting the blood EPA concentration before the administration from the measured blood concentration.

Test Example 6-4 <Pharmacokinetics in Humans (Continuous Administration Test)>

The capsule having the self-emulsifying composition of the present invention containing 80% by weight of EPA-E as its content is orally administered to human (healthy adult males of 20 to 40 years old with a body weight of 55.0 to 77.0 kg and a BMI of 18.5 or more but less than 25.0) once a day immediately after morning meals for 11 days to evaluate the change of blood EPA concentration. The self-emulsifying composition in an amount corresponding to 500, 1000, 2000, 40000, 6000 or 8000 g of EPA-E is orally administered to each human by using 200 mL of water. Three meals are to be taken daily. The blood is collected 1, 2, 3, 4, 5, 6, 8, 10, 12, 18 and 24 hours after the administration at days 1 and 11 of administration ("24 hours after the administration" refers to "just before the administration on the next day"), and 24 hours after the administration at days 2 to 10. Immediately after the collection, the blood is cooled on ice, and centrifuged at 2000×g at 4° C. for 10 minutes to separately collect the plasma. After storing the resulting plasma at a temperature not higher than −20° C. in frozen state, concentration of the EPA in the plasma is measured by LC/MS/MS.

For the control group, a capsule having the EPA-E stock solution filled in the capsule is orally administered to human (healthy adult males of 20 to 40 years old with a body weight of 55.0 to 77.0 kg and a BMI of 18.5 or more but less than 25.0) in an amount corresponding to 1800 mg of the EPA-E once a day immediately after morning meals for 11 days, and change in the blood EPA concentration is evaluated by repeating the procedure as described above.

The capsule having the self-emulsifying composition of the present invention containing 80% by weight of EPA-E as its content is also orally administered to human under fasting conditions, and the measurement is conducted by repeating the procedure as described above.

From the test results, the maximum plasma ω3 PUFA concentration (Cmax), the area under the plasma ω3 PUFA concentration vs time curve from zero to 24 hours ($AUC_{0-24}$), the time until the maximum plasma ω3 PUFA concentration is attained (Tmax) and the plasma ω3 PUFA elimination half-life ($t_{1/2}$) at day 1 of administration and the plasma ω3 PUFA concentration 24 hours after the administration ($C_{24}$) at days 1 to 11 are calculated. The maximum plasma ω3 PUFA concentration in steady state (Css max), the minimum plasma ω3 PUFA concentration in steady state (Css min) and the average plasma ω3 PUFA concentration in steady state (Css ave) are also calculated. In the calculation of each parameter, correction is made by subtracting the blood EPA concentration before the administration from the measured blood concentration.

Test Example 7 <Appearance of the Capsule>

The soft capsules obtained in the Examples were visually inspected for the color and shape of the capsule and the property of the capsule content after the completion of filling and drying.

The capsules with change in the "color", distortion, depression, or the like in the "shape", and cloudiness, separation, or the like in the "property of the capsule content" were evaluated as "poor," and the capsules without such problems were evaluated as "normal."

The test results are shown in Table 1. In the Table below, "-" means that the corresponding component was not added or that the corresponding item was not measured.

TABLE 1

| Component | | Ex. 1 | Ex. 2 | Ex. 3 | Ex. 4 | Ex. 5 | Ex. 6 | Ex. 7 | Ex. 8 |
|---|---|---|---|---|---|---|---|---|---|
| Filled in capsule | | Yes | Yes | Yes | — | Yes | Yes | — | — |
| Ethyl eicosapentaenoate | | 80.0 | 75.0 | 80.0 | 80.0 | 80.0 | 83.0 | 80.0 | 80.0 |
| Purified water | | 1.7 | 1.1 | 1.2 | 1.2 | 2.0 | 1.0 | 1.2 | 1.2 |
| Polyoxyethylene (20) sorbitan oleate | | 10.5 | 10.8 | 7.2 | 6.5 | 5.8 | 8.5 | 11.1 | 13.1 |
| Polyoxyethylene sorbitan trioleate | | — | — | — | — | — | — | — | — |
| Polyoxyl 35 castor oil | | — | 10.8 | 7.2 | 7.9 | 5.8 | 4.5 | 3.3 | 1.3 |
| Polyoxyethylene (60) hydrogenated castor oil | | — | — | — | — | — | — | — | — |
| Soybean lecithin | | 7.8 | 2.4 | 4.4 | 4.4 | 6.4 | 3.0 | 4.4 | 4.4 |
| Propylene glycol | | — | — | — | — | — | — | — | — |
| Total | | 100.0 | 100.0 | 100.0 | 100.0 | 100.0 | 100.0 | 100.0 | 100.0 |
| Test. Ex. 1 | Appearance | Transparent | Transparent | Transparent | Transparent | Transparent | Transparent | Transparent | Transparent |
| Test. Ex. 2 | Self-emulsifying property | Good | Good | Good | Good | — | Good | Good | Good |
| | Composition dispersibility | Good | Good | Good | Good | — | Good | Good | Good |
| | Emulsion stability | Good | Good | Good | Good | — | Good | Good | Good |
| Test. Ex. 3 Emulsion droplet diam. | Purified water at 37° C. (μm) | 0.44 | 0.34 | 0.27 | — | 0.35 | 0.25 | — | — |
| | Japanese Pharmacopeia, 1st fluid, 37° C. (μm) | 0.36 | 0.29 | 0.22 | — | 0.57 | 0.29 | — | — |
| Test. Ex. 4 Appearance | Stored at 5° C. | Transparent | Transparent | Transparent | Transparent | Transparent | Transparent | Transparent | Transparent |
| | Stored at 40° C. | Transparent | Transparent | Transparent | Transparent | Transparent | Transparent | Transparent | Transparent |
| Test Ex. 5 | Cmax | 104.7 | — | 128.7 | — | 80.0 | — | — | — |
| | $AUC_{0-2}$ | 94.0 | — | 97.8 | — | 60.7 | — | — | — |
| | $AUC_{0-24}$ | 617.8 | — | 1036.3 | — | 566.6 | — | — | — |
| Test Ex. 6 | Capsule appearance | Normal | Normal | Normal | — | Normal | Normal | — | — |

| Component | | Ex. 9 | Ex. 10 | Ex. 11 | Comp. Ex. 1 | Comp. Ex. 2 | Comp. Ex. 3 | Comp. Ex. 4 | Comp. Ex. 5 EPA-E stock solution (Fasted control) |
|---|---|---|---|---|---|---|---|---|---|
| Filled in capsule | | — | — | — | — | — | — | — | — |
| Ethyl eicosapentaenoate | | 80.0 | 80.0 | 83.0 | 80.0 | 80.0 | 75.2 | 80.0 | |
| Purified water | | 4.0 | 2.0 | 2.0 | — | 8.0 | — | 1.2 | |
| Polyoxyethylene (20) sorbitan oleate | | 5.1 | — | 8.0 | 7.2 | 3.8 | 5.8 | — | |
| Polyoxyethylene sorbitan trioleate | | — | 5.8 | — | — | — | — | — | |
| Polyoxyl 35 castor oil | | 5.1 | 5.8 | — | 7.2 | 3.8 | 5.8 | 14.4 | |
| Polyoxyethylene (60) hydrogenated castor oil | | — | — | 4.0 | — | — | — | — | |
| Soybean lecithin | | 5.8 | 6.4 | 3.0 | 5.6 | 4.4 | 6.5 | 4.4 | |
| Propylene glycol | | — | — | — | — | — | 6.7 | — | |
| Total | | 100.0 | 100.0 | 100.0 | 100.0 | 100.0 | 100.0 | 100.0 | |
| Test. Ex. 1 | Appearance | Transparent | Transparent | Transparent | Separated | Separated | Transparent | Cloudy | |
| Test. Ex. 2 | Self-emulsifying property | Good | Good | Good | Not evaluated | Not evaluated | Good | Good | |
| | Composition dispersibility | Good | Good | Good | | | Good | Good | |
| | Emulsion stability | Good | Good | Good | | | Good | Good | |
| Test. Ex. 3 Emulsion droplet diam. | Purified water at 37° C. (μm) | 0.28 | — | — | | | 0.15 | — | |
| | Japanese Pharmacopeia, 1st fluid, 37° C. (μm) | 0.32 | — | — | | | 0.18 | — | |

TABLE 1-continued

| | | | | | | | |
|---|---|---|---|---|---|---|---|
| Test. Ex. 4 | Stored at 5° C. | Transparent | Transparent | Transparent | Transparent | Cloudy | |
| Appearance | Stored at 40° C. | Transparent | Transparent | Transparent | Separated | Cloudy | |
| Test Ex. 5 | Cmax | — | — | — | — | — | 18.4 |
| | $AUC_{0-2}$ | — | — | — | — | — | 11.3 |
| | $AUC_{0-24}$ | — | — | — | — | — | 76.6 |
| Test Ex. 6 | Capsule appearance | — | — | — | — | — | — |

TABLE 2

| Test Example 6-2 | Capsule preparation of Test Example 6-2 (Dose, 1800 mg) | Capsule preparation of Test Example 6-2 (Dose, 1800 mg) | Control group, EPA-E stock solution |
|---|---|---|---|
| Meal | No | Yes | No |
| Cmax (μg/mL) | 65.1 | 111.3 | 4.6 |
| C24 hr (μg/mL) | 19.5 | 28.6 | 2.4 |
| AUC0-72 hr (μg · hr/mL) | 1266.0 | 1932.1 | 113.1 |
| Tmax (hr) | 5.2 | 3.3 | 10.8 |
| t½ (hr) | 31.2 | 42.6 | 71.7 |

TABLE 3

| Test Example 6-3 | Capsule preparation of Test Example 6-2 (Dose, 3600 mg) | Capsule preparation of Test Example 6-2 (Dose, 3600 mg) | Control group, EPA-E stock solution |
|---|---|---|---|
| Meal | No | Yes | No |
| Cmax (μg/mL) | 174.2 | 184.5 | 3.6 |
| C24 hr (μg/mL) | 36.4 | 37.7 | 1.2 |
| AUC0-72 hr (μg · hr/mL) | 2845.5 | 2615.9 | 113.7 |
| Tmax (hr) | 5.2 | 4.3 | 21.8 |
| t½ (hr) | 58.7 | 42.4 | 22.8 |

Example 1 is the composition containing poly oxy ethylene sorbitan fatty acid ester as the only emulsifier together with certain amounts of lecithin and water, and as shown in Table 1, this composition had good appearance as well as excellent self-emulsifying property. This result indicates that the merits of the present invention are realized by the composition containing lecithin wherein the polyoxyethylene sorbitan fatty acid ester is the only emulsifier.

Examples 2 to 10 are compositions containing polyoxyethylene castor oil as an additional emulsifier. These compositions also exhibited good appearance as well as excellent self-emulsifying property as shown in Table 1.

Example 11 is a composition containing polyoxyethylene hydrogenated castor oil as an additional emulsifier. This composition also exhibited good appearance as well as excellent self-emulsifying property as shown in Table 1.

Comparative Example 1 is a composition not containing the water, and this composition became separated. Comparative Example 2 is a composition containing 8% by weight of water, and this composition also became separated.

In the present invention, water was used instead of adding the ethanol or the polyhydric alcohol to thereby improve the compatibility of the composition. The composition became separated due to inadequate compatibility when no water was used, while the composition still separated even with the use of water when the amount of water was too much in relation to the amount of the composition. In the meanwhile, the separation did not occur in Examples 1 to 6 containing 1 to 4% by weight of water. These results indicate that presence of a certain amount (approximately 0.5 to 6% by weight) of water is important for the good appearance.

Comparative Example 3 is a composition not containing water but containing polyhydric alcohol. As in the case of Example 1, this composition had good appearance as well as good self-emulsifying property.

However, the composition of Comparative Example 3 separated after overnight storage at 40° C., and this demonstrates importance of adding a particular amount (approximately 0.5 to 6% by weight) of water to the composition in view of improving the appearance and the like.

Comparative Example 4 is a composition containing polyoxyethylene castor oil for the emulsifier and not containing the polyoxyethylene sorbitan fatty acid ester, and in the case of this composition, the composition had cloudy appearance.

This demonstrates the importance of the incorporation of the polyoxyethylene sorbitan fatty acid ester as the emulsifier for the good appearance.

Examples 1, 3, and 5 show the kinetics when the self-emulsifying composition was added to fasted animals.

In the animals having these self-emulsifying compositions administered thereto, Cmax and $AUC_{0-2}$ values which are the parameters of the absorption speed were significantly higher than those in the control group animals (under fasting) administered with the EPA-E stock solution as a control. More specifically, it was confirmed that, when the self-emulsifying compositions of the Examples were administered, amount of the EPA absorbed until 24 hours after the oral administration increased, and also, EPA absorption was rapid especially after the oral administration compared to the control group.

Test Example 6-2 shows parameters when the self-emulsifying composition of the present invention containing 80% by weight of the EPA-E in an amount corresponding to 1800 mg of EPA-E and 1800 mg of EPA-E were respectively administered to human. Under the fasting conditions, all of the parameters Cmax, $C_{24}$ and $AUC_{0-72}$ were about 10 times higher in the case of the composition of the Example (Cmax was 14.2 times higher, $C_{24}$ was 8.1 times higher, and $AUC_{0-72}$ was 11.2 times higher), and rapid absorption of the EPA after the oral administration was confirmed. Test Example 6-3 shows the parameters when the inventive self-emulsifying composition in an amount corresponding to 3600 mg of EPA-E and 3600 mg of EPA-E were respectively administered, and the parameters were several tens times higher (Cmax was 48.4 times higher, $C_{24}$ was 30.3 times higher, and $AUC_{0-72}$ was 25.0 times higher), confirming similar rapid absorption. It was also confirmed that the self-emulsifying composition of the present invention was less likely to be affected by the meal, and that it exhibits high EPA absorption irrespective of whether it is taken before or after meals.

Accordingly, the self-emulsifying composition of the present invention would be a candidate for the self-emulsifying preparation capable of rapidly and markedly increasing the blood EPA concentration with rapid and effective pharmacological action even if taken under fasting conditions, that is to say, taken before meals, at bedtime or the like.

Self-Emulsifying Capsule Preparations of Examples 2-1 and 2-2 and Capsule Preparation of Comparative Example 2-3

The self-emulsifying compositions and the composition of Comparative Example 2-3 were prepared and stored by repeating the procedure of Example 1 so that the compositional ratios were as shown in Table 4. The formulations of the self-emulsifying compositions are shown in Table 4.

375 mg of the self-emulsifying composition was filled in the capsule in Examples 2-1 and 2-2, and 441 mg of the self-emulsifying composition was filled in the capsule in Comparative Example 2-3 (300 mg of EPA-E in both cases). In each case, the soft gelatin capsule having the content filled therein was produced by rotary method. Deformation of the capsule film was not noticed for the self-emulsifying capsule preparations prepared by this method.

The compositional ratios of the encapsulated contents are shown in Table 4.

Test Example 8 <Hardness of the Capsule>

The capsule preparations of Examples 2-1 and 2-2 and Comparative Example 2-3 were measured in hardness. The preparations after storage at 40° C. and a relative humidity of 75% for 1, 2, and 4 weeks were also measured in hardness.

The results at the initial stage and the results after the storage at 40° C. for 1, 2, and 4 weeks are shown in Table 4. The preparation at the initial stage refers to the preparation which has been stored at room temperature after its production until the evaluation of the hardness. Since having been stored at 40° C. as sealed in aluminum packages, the preparations were not affected by the moisture.

TABLE 4

| Component | | Ex. 2-1 wt % | Ex. 2-2 wt % | Comp. Ex. 2-3 wt % |
|---|---|---|---|---|
| Ethyl eicosapentaenoate | | 80.0 | 80.0 | 68.0 |
| Purified water | | 2.0 | 1.8 | — |
| Polyoxyethylene (20) sorbitan oleate | | 5.8 | 5.8 | 7.1 |
| Polyoxyl 35 castor oil | | 5.8 | 5.8 | 7.1 |
| Soybean lecithin | | 6.4 | 6.4 | 9.5 |
| Zymolytic lecithin | | — | 0.2 | — |
| Tocopherol | | — | — | — |
| Sodium erythorbate | | ^ | — | — |
| Propylene glycol | | — | — | 8.3 |
| Total | | 100.0 | 100.0 | 100.0 |
| Test Ex. 7 Hardness (kgf) | Initial stage | 28.9 | 24.7 | 15.7 |
| | 40° C., 1 week | 25.5 | 22.3 | 9.1 |
| | 40° C., 2 weeks | 24.5 | 20.5 | 8.9 |
| | 40° C., 4 weeks | 27.4 | 22.3 | 8.1 |

Examples 2-1 and 2-2 are preparations produced by encapsulating the self-emulsifying composition of the present invention. These capsules had a hardness of 20 kgf or higher. On the other hand, the composition of Comparative Example 2-3 contains a larger amount (8.3% by weight) of propylene glycol (a polyhydric alcohol), and the hardness of the capsule preparation was already inferior compared to Examples at the initial stage. When the hardness was evaluated after storing in sealed environment at 40° C. for 1 to 4 weeks, substantially no change was noticed in Examples 2-1 and 2-2, while, in Comparative Example 2-3, the hardness declined to 57% of the initial hardness in 1 week, and further declined with time.

INDUSTRIAL APPLICABILITY

The self-emulsifying composition of the present invention is excellent in at least one out of the compatibility (appearance), the self-emulsifying property, the composition dispersibility, the emulsion stability and the absorbability, and it, as being absorbed rapidly even if taken before meals, suppresses increase of serum TG after the meal. The self-emulsifying composition of the present invention is useful for incorporating in various foods, or as food for special dietary uses, food with health claims (food for specified health use and food with nutrient function claims), health food (supplement), or a pharmaceutical product.

The self-emulsifying composition of the present invention has no or low content of the polyhydric alcohol, and therefore, the composition is free from the problem of softening and deformation of the capsule during the distribution or storage caused by the polyhydric alcohol. In other words, the self-emulsifying composition of the present invention is associated with reduced risk of quality change.

The self-emulsifying composition of the present invention has the quality as a pharmaceutical product capable of being stored in a cold or hot location since the composition does not become cloudy or separated even if stored in low or high temperature environment.

The invention claimed is:

1. A self-emulsifying preparation containing a self-emulsifying composition encapsulated in a capsule, the self-emulsifying composition comprising, when total amount of the self-emulsifying composition is 100% by weight,
    (a) 50 to 95% by weight of at least one compound selected from the group consisting of eicosapentaenoic acid (EPA) and pharmaceutically acceptable salts and esters thereof,
    (b) 0.5 to 6% by weight of water,
    (c) 1 to 29% by weight of an emulsifier which is a nonionic surfactant,
    (d) a content of polyhydric alcohol is up to 4% by weight of total amount of the composition,
    (e) a content of ethanol is up to 4% by weight of total amount of the composition, and
    (f) 3 to 40 parts by weight of lecithin in relation to 100 parts by weight of the at least one compound selected from the group consisting of EPA and pharmaceutically acceptable salts and esters thereof,
    which upon administration to human satisfies at least one selected from among following (g) to (k) calculated by conducting a correction by subtracting plasma EPA concentration before the administration:
    (g) maximum plasma EPA concentration is at least 50 μg/mL;
    (h) plasma EPA concentration 2 hours after the administration is at least 20 μg/mL;
    (i) time required to reach the maximum plasma EPA concentration (Tmax) is up to 6 hours;
    (j) area under the curve of the plasma EPA concentration at 0 to 72 hours after the administration is at least 500 μg·hr/mL; and
    (k) blood EPA concentration 24 hours after the administration is 5 to 100 μg/mL.

2. The self-emulsifying preparation according to claim 1, wherein the amount of the at least one compound selected from the group consisting of EPA and pharmaceutically acceptable salts and esters thereof in the composition when administered to a human is 1000 mg to 10000 mg.

3. The self-emulsifying preparation according to claim 1, wherein the EPA and pharmaceutically acceptable salts and esters thereof are an ethyl ester of EPA.

4. The self-emulsifying preparation according to claim 1, wherein the composition contains a polyoxyethylene sorbitan fatty acid ester as the nonionic surfactant.

5. The self-emulsifying preparation according to claim 1, wherein the composition contains a polyoxyethylene castor oil as the nonionic surfactant.

6. A self-emulsifying composition comprising, when the total composition is 100% by weight,
  a) 50 to 95% by weight of at least one compound selected from the group consisting of eicosapentaenoic acid (EPA) and pharmaceutically acceptable salts and esters thereof,
  b) 0.5 to 6% by weight of water,
  c) 1 to 29% by weight of an emulsifier which is a nonionic surfactant,
  d) a content of polyhydric alcohol is up to 4% by weight of total amount of the composition,
  e) a content of ethanol is up to 4% by weight of total amount of the composition, and
  f) 3 to 40 parts by weight of lecithin in relation to 100 parts by weight of the at least one compound selected from the group consisting of EPA and pharmaceutically acceptable salts and esters thereof,
  which upon administration to human satisfies at least one selected from among following (g) to (k) calculated by conducting a correction by subtracting plasma EPA concentration before the administration:
  (g) maximum plasma EPA concentration is at least 50 µg/mL;
  (h) plasma EPA concentration 2 hours after the administration is at least 20 µg/mL;
  (i) time required to reach the maximum plasma EPA concentration (Tmax) is up to 6 hours;
  (j) area under the curve of the plasma EPA concentration at 0 to 72 hours after the administration is at least 500 µg·hr/mL; and
  (k) blood EPA concentration 24 hours after the administration is 5 to 100 µg/mL.

7. The self-emulsifying composition according to claim 6, wherein the amount of the at least one compound selected from the group consisting of EPA and pharmaceutically acceptable salts and esters thereof in the composition when administered to a human is 1000 mg to 10000 mg.

8. The self-emulsifying composition according to claim 6, wherein the EPA and its pharmaceutically acceptable salts and esters are an ethyl ester of EPA.

9. The self-emulsifying composition according to claim 8, wherein when the composition is administered, the maximum plasma EPA concentration calculated by conducting a correction by subtracting the plasma EPA concentration before the administration is at least 50 µg/mL, and the area under the curve of the plasma EPA concentration at 0 to 72 hours after the administration is at least 500 µg·hr/mL.

10. The self-emulsifying composition according to claim 8, wherein, when the composition is administered under fasting, the maximum plasma EPA concentration calculated by conducting a correction by subtracting the plasma EPA concentration before the administration is at least three times as high as the maximum plasma EPA concentration immediately after the meal, or the area under the curve of the plasma EPA concentration at 0 to 72 hours after the administration is at least twice as large as the area under the curve of the plasma EPA concentration immediately after the meal.

11. The self-emulsifying composition according to claim 6, wherein the composition contains a polyoxyethylene sorbitan fatty acid ester as the nonionic surfactant.

12. The self-emulsifying composition according to claim 6, wherein the composition contains a polyoxyethylene castor oil as the nonionic surfactant.

* * * * *